United States Patent
Albed Alhnan

(10) Patent No.: US 12,318,488 B2
(45) Date of Patent: Jun. 3, 2025

(54) SOLID DOSAGE FORM PRODUCTION

(71) Applicant: University of Central Lancashire, Preston (GB)

(72) Inventor: Mohamed Albed Alhnan, London (GB)

(73) Assignee: University of Central Lancashire, Preston (GB)

( * ) Notice: Subject to any disclaimer, the term of this patent is extended or adjusted under 35 U.S.C. 154(b) by 906 days.

(21) Appl. No.: 17/268,378

(22) PCT Filed: Aug. 13, 2019

(86) PCT No.: PCT/GB2019/052279
§ 371 (c)(1),
(2) Date: Feb. 12, 2021

(87) PCT Pub. No.: WO2020/035680
PCT Pub. Date: Feb. 20, 2020

(65) Prior Publication Data
US 2021/0169809 A1    Jun. 10, 2021

(30) Foreign Application Priority Data

Aug. 13, 2018 (GB) ..................... 1813186

(51) Int. Cl.
| | |
|---|---|
| A61K 9/20 | (2006.01) |
| A61K 9/00 | (2006.01) |
| B33Y 10/00 | (2015.01) |
| B33Y 30/00 | (2015.01) |
| B33Y 70/00 | (2020.01) |
| B33Y 80/00 | (2015.01) |

(52) U.S. Cl.
CPC .......... *A61K 9/2095* (2013.01); *A61K 9/0053* (2013.01); *A61K 9/2072* (2013.01); *B33Y 10/00* (2014.12); *B33Y 30/00* (2014.12); *B33Y 70/00* (2014.12); *B33Y 80/00* (2014.12)

(58) Field of Classification Search
None
See application file for complete search history.

(56) References Cited

U.S. PATENT DOCUMENTS

2015/0140036 A1* 5/2015 Mannick ............ A61K 31/4745
435/5

FOREIGN PATENT DOCUMENTS

| CN | 105687151 A | 6/2016 |
|---|---|---|
| CN | 110075080 A | 8/2019 |
| WO | 95/11007 A1 | 4/1995 |

(Continued)

OTHER PUBLICATIONS

International Search Report and Written Opinion dated Feb. 20, 2020, for International Patent Application No. PCT/GB2019/052279.

(Continued)

*Primary Examiner* — Kyung S Chang
(74) *Attorney, Agent, or Firm* — ArentFox Schiff LLP; Shawn P. Foley

(57) ABSTRACT

The present invention provides methods of preparing solid dosage form, particularly pharmaceutical dosage forms, using extrusion and 3D-printing, as well as the solid dosage form itself, the compositions used to make said items, uses of the solid dosage forms, and containers used in their preparation.

11 Claims, 13 Drawing Sheets

(56) References Cited

FOREIGN PATENT DOCUMENTS

| WO | 03/092633 A2 | 11/2003 |
|---|---|---|
| WO | 2007/106182 A2 | 9/2007 |
| WO | 2016/038356 A1 | 3/2016 |
| WO | 2017/134418 A1 | 8/2017 |
| WO | 2018/035511 A1 | 2/2018 |
| WO | 2018137686 A1 | 8/2018 |
| WO | 2019/025857 A2 | 2/2019 |
| WO | 2019137200 A1 | 7/2019 |
| WO | 2020/148442 A1 | 7/2020 |

OTHER PUBLICATIONS

GB Search Report dated Feb. 15, 2019, for GB Patent Application No. 1813186.2.
Schmitt et al. Low temperature melt extrusion of pharmaceutical formulation in poly (ethylene oxide). Proceed. Intl. Symp. Control. Rel. Bioact. Mater. 2000. 27: 1252-3.
Pereira et al. 'Temporary Plasticiser': A novel solution to fabricate 3D printed patient-centred cardiovascular 'Polypill' architectures. Eur J Pharm Biopharm. Feb. 2019;135:94-103. doi: 10.1016/j.ejpb.2018.12.009. Epub Dec. 21, 2018.
Goyanes et al. Fused-filament 3D printing (3DP) for fabrication of tablets. Int J Pharm. Dec. 10, 2014;476(1-2):88-92. doi: 10.1016/j.ijpharm.2014.09.044. Epub Sep. 30, 2014.
Skowyra et al. Fabrication of extended-release patient-tailored prednisolone tablets via fused deposition modelling (FDM) 3D printing. Eur J Pharm Sci. Feb. 20, 2015;68:11-7. doi: 10.1016/j.ejps.2014.11.009. Epub Nov. 25, 2014.
Okwuosa et al., "A Lower Temperature FDM 3D Printing for the Manufacture of Patient-Specific Immediate Release Tablets," Pharm Res. Nov. 2016;33(11):2704-12. doi: 10.1007/s11095-016-1995-0. Epub Aug. 9, 2016 (9 pages).
Goyanes et al., "3D Printing of Medicines: Engineering Novel Oral Devices with Unique Design and Drug Release Characteristics," Mol Pharm. Nov. 2, 2015;12(11):4077-84. doi: 10.1021/acs.molpharmaceut.5b00510. Epub Oct. 16, 2015 (8 pages).
Khaled et al., "3D extrusion printing of high drug loading immediate release paracetamol tablets," Int. J. Pharmaceutics, vol. 538, Issues 1-2, Mar. 1, 2018, pp. 223-230 (8 pages).
International Preliminary Report on Patentability for International Patent Application No. PCT/GB2019/052279, dated Feb. 16, 2021. (13 pages).
Pietrzak K, Isreb A, Alhnan MA. A flexible-dose dispenser for immediate and extended release 3D printed tablets. Eur J Pharm Biopharm. Oct. 2015;96:380-7. doi: 10.1016/j.ejpb.2015.07.027.
Alhnan et al., "Emergence of 3D Printed Dosage Forms: Opportunities and Challenges", Pharmaceutical Research, XP036002018, ISSN: 0724-8741, vol. 33, No. 8, May 18, 2016, pp. 1817-1832.
Extended European Search Report and Search Opinion received for European Application No. 24210401.6, mailed on Feb. 10, 2025, 6 pages.
Liu et al., "A large-scale double-stage-screw 3D printer for fused deposition of plastic pellets", Journal of Applied Polymer Science, Available online at: <https://onlinelibrary.wiley.com/doi/full/10.1002/app.45147>, XP093238873, US ISSN: 0021-8995, vol. 134, No. 31, Apr. 6, 2017, pp. 1-9.
Whyman et al., "Design and development of an extrusion system for 3D printing biopolymer pellets", The International Journal of Advanced Manufacturing Technology, vol. 96, No. 9, XP036509346, Mar. 6, 2018, pp. 3417-3428.

* cited by examiner

SOLID DOSAGE FORM PRODUCTION

CROSS-REFERENCE TO RELATED APPLICATIONS

This application is a U.S. National Stage application under 35 U.S.C. § 371 of co-pending International Application No. PCT/GB2019/052279, which was filed on Aug. 13, 2019, which in term claims priority to UK Patent Application No. 1813186.2, which was filed on Aug. 13, 2018, both of which are incorporated herein by reference in their entirety.

INTRODUCTION

The present invention relates methods for the production of solid dosage forms (and in some cases, solid items more generally), specifically using extrusion and/or deposition. The present invention also relates to the solid dosage forms (or solid items) themselves, precursor compositions used to prepare the solid dosage forms, as well as apparatuses for use in the production of solid dosage forms and methods for the operation thereof. The present invention also relates to solid dosage forms obtainable by such methods and apparatus, a solid dosage form package, relevant materials and compositions used to prepare the solid dosage forms (and processes for their manufacture), a computer for controlling the relevant preparation process (and software and computer-implemented methods connected therewith), and a system for collecting data relating to the solid dosage form production process (and databases associated therewith).

BACKGROUND

The production and consumption of medicines, nutraceuticals, and food supplements (collectively referred to herein as "healthcare dosage forms"), in solid dosage form (e.g. tablets, implants, etc.) is ever increasing, not least due to an increased reliance on such products by national health services and the like in an increasingly health-conscious society. Where possible, solid dosage forms tend to be most preferred, relative to other formulations (e.g. injectable liquid formulations), due to their ease of administration (i.e. usually orally) which gives rise to better patient compliance, storability and transportability (low space requirements and ease of packaging), high stability (longer lifetimes—less degradation). However, despite the significant advantages of solid dosage forms over other dosage forms, they are often more onerous to manufacture (in terms of the number of both ingredients and processing steps) and are generally only cost effective to produce on large scale, meaning large manufacturing facilities with sophisticated equipment is usually required. These manufacturing limitations have a detrimental impact on consumer choice and/or the customisability of healthcare dosage forms since, for example, it is impractical and non-cost effective to mass produce a wide variety of different dosages for a given medicament via conventional manufacturing techniques. Consumers (e.g. patients) and healthcare professionals (e.g. doctors, pharmacists) must therefore make the best of the limited variety of dosages available, as dictated by the suppliers rather than a consumer's need.

Since the advent of 3-dimensional (3D) printing in the early 1980s, a number of researchers have attempted to make viable use of 3D printing technology to fabricate healthcare solid dosage forms. For instance, for well over a decade, MIT and Therics, Inc. have collaborated in the development of viable pill printing machines which utilise 3D printers to print solid pharmaceutical dosage forms in situ. The technology forms pills via a multi-layered 3D printing process involving precise printing of doses of a liquid drug solution onto thin layers of fine powder before further layers are then applied (e.g. further powder, binder, etc.). Examples of such processes are disclosed in earlier publications, such as WO95/11007 (MASSACHUSETTS INSTITUTE OF TECHNOLOGY) and WO03/092633 (THERICS, INC.), which describe inter alia the production of solid dosage forms having various structures and drug release profiles. However, regulatory approval (e.g. by the FDA or MHRA) for such 3D drug printing systems still remains elusive, and for the time being they are suitable only for low dose drug products, partly owing to the limited solubility of many drugs within the relevant ink solutions. As such, patient choice would still be very limited, as would the options of a doctor or pharmacist in providing specially-tailored treatments. Furthermore, resolution and shape of the solid dosage form still remains an issue. A particular issue with prior art 3D printing systems is the use of elevated temperatures in printing the solid dosage item itself and/or in the preparation of filaments used in the printing process. The use of elevated temperatures in the manufacture of printed solid dosage forms can lead to some of the components of the solid dosage form to thermally degrade. Thus, printing processes which utilise elevated temperatures are not suited for use with thermally sensitive components, for example thermally sensitive active ingredients, and/or high loading levels of the thermally sensitive component. This can severely limit the applications of 3D printing solid dosage forms, as only thermally stable components may be used, and/or only low dosage forms may be prepared. Biological active ingredients, such as mono-clonal antibodies, are particularly prone to thermal degradation.

The Applicants previous work outlined in WO2016/038356 (University of Central Lancashire), which primarily focused on the use in 3D printing of drug-containing FDM filaments, aims to solve one or more of the aforesaid problems. However, there remains a need for alternative solutions. For instance, though WO2016/038356 provides various innovative options for reducing the melting/softening temperatures of the drug-containing filaments, for some drugs (especially those with low decomposition temperatures) the filament printing temperatures can still be too high, and decomposition can occur during printing. Such drug decomposition can also occur during preparation of the filaments themselves, especially for filaments produced via hot-melt extrusion involving batch-wise heating of pre-extruded compositions prior to extrusion. Furthermore, the technology described in WO2016/038356 deploys significant proportions of thermoplastics in the formation of dosage forms, which can be undesirable and limit maximum drug-loadings. It is desirable to extend the scope of applicability of the 3D-printing technology described in WO2016/038356, for instance by allowing for a broader range of input materials. For example, the 3D printing of solid dosage forms containing polypeptides, proteins and other biopharmaceuticals is seen as desirable, notwithstanding the stability challenges these inherit. It is furthermore desirable to be able to provide such solid dosage forms with immediate, enteric, and/or extended release properties.

It is therefore an object of the invention to provide improved and/or alternative methods of producing solid dosage forms, and to suitably solve at least one problem inherent in the prior art.

SUMMARY OF THE INVENTION

According to a first aspect of the present invention, there is provided a method of preparing an extruded item, the method comprising:
i. providing an extrudable composition comprising an extrudable carrier; and
ii. extruding the extrudable composition into a desired form optionally in association with one or more supplementary elements (e.g. a shell, coating, core);
wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

In one aspect, there is provided a method of preparing a pharmaceutical, nutraceutical, or food supplement solid dosage form, the method comprising:
i) providing an extrudable composition comprising an extrudable carrier; and
ii) extruding the extrudable composition a desired form optionally in association with one or more supplementary elements (e.g. a shell, coating, core);
wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure, e.g. 100 kPa); and the method further comprises removing or partially removing the temporary plasticizer, via vaporisation.

According to a further aspect of the present invention, there is provided a method of preparing an extruded item, the method comprising:
i. Extruding an extrudable composition into a desired form, wherein the extrudable composition is as defined herein.

According to a further aspect of the present invention, there is provided a method of preparing an extruded item, the method comprising:
i. Providing an extrudable composition as herein defined;
ii. Optionally further processing the mixture from step i. to form:
a. an extrudable fluid;
b. an extrudable compressed form; or
c. an extrudable element; and
iii. Extruding the extrudable composition of step i (or of step ii. where applicable) into a desired form.

According to a further aspect of the present invention, there is provided a method of preparing an extruded item, the method comprising:
i. Mixing an extrudable carrier and a temporary plasticiser together; and
ii. Optionally further processing the mixture from step i. to form:
a. an extrudable fluid;
b. an extrudable compressed form; or
c. an extrudable element.
iii. Extruding the extrudable composition obtained from step i (or step ii. if applicable) into a desired form.

According to a further aspect of the present invention, there is provided an extruded item obtainable by, obtained by, or directly obtained by the methods of preparing an extruded item as defined herein.

According to a further aspect of the present invention, there is provided an extruded item comprising:
i. An extrudable carrier; and
ii. Optionally a temporary plasticiser.

According to a further aspect of the present invention, there is provided an extruded item for use in therapy (or for use in the manufacture of a medicament), suitably as defined herein.

According to a further aspect of the present invention, there is provided a use of the extruded item, suitably as defined herein.

In another aspect, there is provided a method of preparing an extrudable composition, the method comprising:
i. Mixing an extrudable carrier and a temporary plasticiser together; and
ii. Optionally further processing the mixture from step i. to form:
a. an extrudable fluid;
b. an extrudable compressed form; or
c. an extrudable element.

According to a further aspect of the present invention, there is provided an extrudable composition obtainable by, obtained by, or directly obtained by the method of preparing an extrudable composition as defined herein.

According to a further aspect of the present invention, there is provided an extrudable composition comprising:
i. An extrudable carrier; and optionally ii. A temporary plasticiser.
As indicated above, the extrudable composition may be provided in a variety of forms, optionally as an extrudable fluid, optionally as an extrudable compressed form, and/or optionally as an extrudable element (e.g. a 3D-printable filament). Though any form of the extrudable composition may be transformed into another form, the resulting product may still be considered an extrudable composition.

According to a further aspect of the present invention, there is provided a method of processing an extrudable composition to produce an extrudable fluid, the method comprising melting or softening (suitably through heating) the extrudable composition.

According to a further aspect of the present invention, there is provided a method of processing an extrudable composition to produce an extrudable compressed form, the method comprising compressing the extrudable composition.

According to a further aspect of the present invention, there is provided a method of processing an extrudable composition to produce an extrudable element, the method comprising extruding or moulding the extrudable composition into an extrudable element.

According to a further aspect of the present invention, there is provided a method of converting an extrudable fluid to an extrudable compressed form.

According to a further aspect of the present invention, there is provided a method of converting an extrudable fluid to an extrudable element.

According to a further aspect of the present invention, there is provided a method of converting an extrudable compressed form to an extrudable fluid.

According to a further aspect of the present invention, there is provided a method of converting an extrudable compressed form to an extrudable element.

According to a further aspect of the present invention, there is provided a method of converting an extrudable element to an extrudable compressed form.

According to a further aspect of the present invention, there is provided a method of converting an extrudable element to an extrudable fluid.

According to a further aspect of the present invention, there is provided an extrusion apparatus comprising an extruder and suitably also comprising an extrudable composition as defined herein.

According to a further aspect of the present invention, there is provided a method of producing an extruded item package, the method comprising packaging one or more extruded items as defined herein, wherein the one or more extruded items are optionally the same or different.

According to a further aspect of the invention, there is provided an extruded item package, obtainable by, obtained by, or directly obtained by the method of producing an extruded item package as defined herein.

According to a further aspect of the invention, there is provided an extruded item package, comprising one or more extruded items, as defined herein, wherein the one or more extruded items are optionally the same or different, within a packaging.

According to a further aspect of the present invention, there is provided a method of producing an extrudable composition package, the method comprising packaging one or more extrudable compositions as defined herein, wherein the one or more extrudable compositions are optionally the same or different.

According to a further aspect of the present invention, there is provided an extrudable composition package, obtainable by, obtained by, or directly obtained by the method of producing an extrudable composition package as defined herein.

According to a further aspect of the present invention, there is provided an extrudable composition package comprising:
  i. An extrudable composition as herein defined; and
  ii. A container (e.g. cartridge or syringe), wherein the container contains the extrudable composition.

According to a further aspect of the present invention, there is provided an extrudable composition package, comprising one or more extrudable compositions, as defined herein, wherein the one or more extrudable compositions are optionally the same or different, within a packaging.

Methods, and judicious variations thereof, of using an extrusion apparatus may be applied (as appropriate) to any of the extrusion apparatuses defined herein, and in addition, aspects of operating the extrusion apparatus may be applied to the method of the invention as defined herein.

In another aspect of the present invention, there is provided a method of preparing an embedded item, the method comprising:
  i. Providing a solidifiable body substance in a fluid or a semi-fluid form;
  ii. Embedding within the solidifiable body substance an embeddable substance;
  iii. Solidifying the solidifiable body substance with the embeddable substance therein.

In another aspect of the present invention, there is provided an embedded item obtainable by, obtained by, or directly obtained by the method of preparing an embedded item as defined herein.

According to a further aspect of the present invention, there is provided an embedded item comprising an embeddable substance within a solidifiable body substance.

According to a further aspect of the present invention, there is provided an embedded item for use in therapy (or for use in the manufacture of a medicament), suitably as defined herein.

According to a further aspect of the present invention, there is provided a use of the embedded item, suitably as defined herein.

According to a further aspect of the present invention, there is provided an embedding apparatus comprising an embedder and suitably also comprising an embeddable substance and a solidifiable body substance.

According to a further aspect of the present invention, there is provided a method of producing an embedded item package, the method comprising packaging one or more embedded items as defined herein, wherein the one or more embedded items are optionally the same or different.

According to a further aspect of the present invention, there is provided an embedded item package, obtainable by, obtained by, or directly obtained by the method of producing an embedded item package as defined herein.

According to a further aspect of the present invention, there is provided an embedded item package, comprising one or more embedded items, as defined herein, wherein the one or more embedded items are optionally the same or different, within a packaging.

According to a further aspect of the present invention, there is provided a solidifiable body substance kit comprising a cartridge filled with the solidifiable body substance as herein defined.

According to a further aspect of the present invention, there is provided an embeddable substance kit comprising a cartridge filled with the embeddable substance as herein defined.

According to a further aspect of the present invention, there is provided an embeddable and solidifiable body substance kit comprising a cartridge filled with the embeddable substance and the solidifiable body substance as herein defined.

According to a further aspect of the present invention, there is provided an embeddable and solidifiable body substance kit comprising a cartridge filled with the embeddable substance as herein defined and a cartridge filled with the solidifiable body substance as herein defined.

Methods, and judicious variations thereof, of using an embedding apparatus may be applied (as appropriate) to any of the embedding apparatuses defined herein, and in addition, aspects of operating the embedding apparatus may be applied to the method of the invention as defined herein.

Any features, including optional, suitable, and preferred features, described in relation to any particular aspect of the invention may also be features, including optional, suitable and preferred features, of any other aspect of the present invention.

BRIEF DESCRIPTION OF THE DRAWINGS

For a better understanding of the invention, and to show how embodiments of the same are put into effect, reference is now made, by way of example, to the following diagrammatic drawings, in which.

DETAILED DESCRIPTION OF THE INVENTION

Definitions

Figure 1:
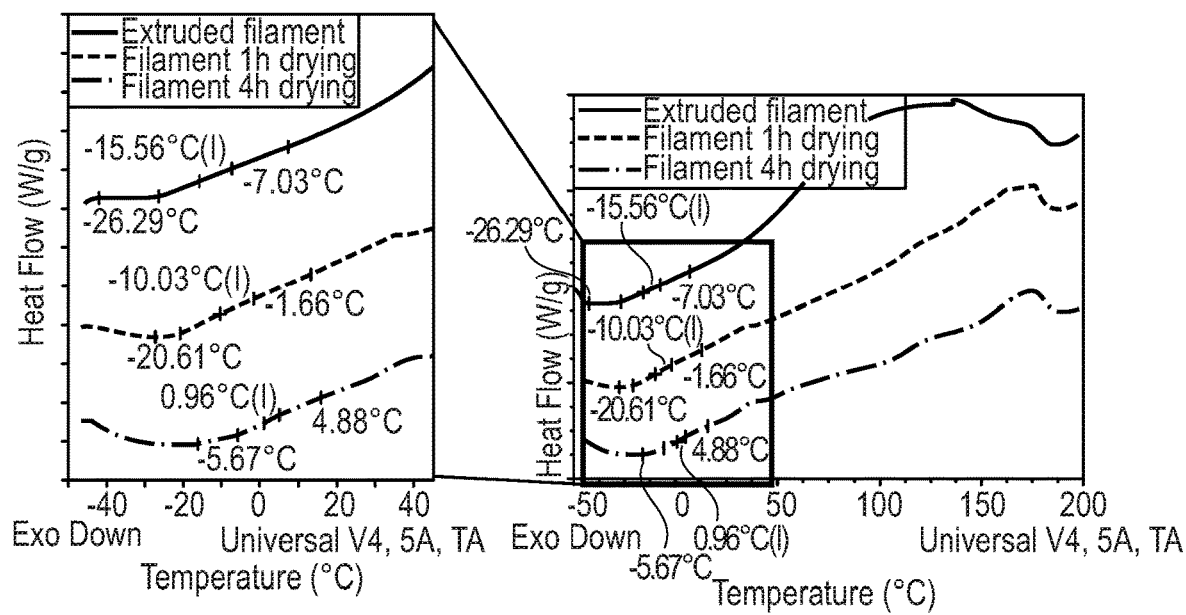
FIG. 1: DSC thermograms of an extruded filament, a 3D printable filament (dried for 1 hour) and a 3D printable filament (dried for 4 hours)

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents that are filed concurrently with or previous to this specification in connection with this application and which are open to public inspection with this specification, and the contents of all such papers and documents are incorporated herein by reference.

For the avoidance of doubt, it is hereby stated that the information disclosed earlier in this specification under the heading "Background" is relevant to the invention and is to be read as part of the disclosure of the invention.

Unless stated otherwise, any reference herein to the term "melt" (or its derivatives), especially in the context of melting the extrudable composition (e.g. filaments, mini-tablets, blend), suitably includes a glass transition or softening of a given material, suitably to allow extrusions thereof (e.g. through a nozzle). However, the term "melt" in the context of a defined "melting point" of a substance is as defined as per the art—a phase transition from solid to liquid.

Herein, references to "glass transition temperature" or "$T_g$" suitably refers to the temperature at which a material softens (e.g. to allow extrusion thereof). Suitably, glass transition temperatures (Tg) of materials described herein may be determined by a standard test method, suitably using dynamic mechanical analysis—a suitable test includes the testing protocol defined by ASTM E1640. Differential Scanning calorimetry (DSC) may also be utilised. For instance, glass transition temperatures may be discerned using the protocols set forth in ASTM E1356 and ASTM D7426. It will be understood by those skilled in the art that references herein to a particular material's glass transition temperature falling within a certain temperature range is intended to mean that at least one glass transition temperature of said material (which may or may not have multiple glass transition temperatures) falls within said temperature range. Suitably unqualified references to a "glass transition temperature" means at least one, suitably means the lowest glass transition temperature, and may suitably mean the glass transition temperature which absorbs the most thermal energy (or is most endothermic). The key, which is selfevident to those skilled in the art, is that sufficient softening of said material occurs under a particular set of circumstances (e.g. at the printing nozzle, where a filament needs to be softened in order to be extruded during the printing process, after which resolidification or rehardening may take place).

Unless stated otherwise, the term "viscosity" as used herein refers to a viscosity determined by means of a Brookfield viscometer (UL adapter/30 rpm/20° C.) in accordance with testing protocols defined by Ph. Eur. 2.2.10 or USP <912> method II.

Unless stated otherwise, any reference herein to an "average" value is intended to relate to the mean value.

Where a composition/item is said to comprise a plurality of stipulated ingredients (optionally in stipulated amounts of concentrations), said composition/item may optionally include additional ingredients other than those stipulated. However, in certain embodiments, a composition/item said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Where the quantity or concentration of a particular component of a given composition is specified as a weight percentage (% weight, wt % or % w/w), said weight percentage refers to the percentage of said component by weight relative to the total weight of the composition as a whole. It will be understood by those skilled in the art that the sum of weight percentages of all components of a composition will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essentially but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is $x_1:y_1:z_1$ respectively, or a range $x_1-x_2:y_1-y_2:z_1-z_2$). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the compositions (i.e., solid dosage forms such as the extruded items/embedded items and/or mixtures used to prepare said solid dosage forms such as the extrudable composition/embeddable substance/solidifiable body substance) of the invention. Where a composition comprises multiple ingredients is described in terms of parts by weight alone (i.e. to indicate only relative ratios of ingredients), it is not necessary to stipulate the absolute amounts or concentrations of said ingredients (whether in total or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

The term "mole percent" (i.e. mol %) is well understood by those skilled in the art, and the mol % of a particular constituent means the amount of the particular constituent (expressed in moles) divided by the total amount of all constituents (including the particular constituent) converted into a percentage (i.e. by multiplying by 100). The concept of mol % is directly related to mole fraction.

The term "substantially free", when used in relation to a given component of a composition (e.g. "a liquid pharmaceutical composition substantially free of compound X"), refers to a composition to which essentially none of said component is present. When a composition is "substantially free" of a given component, said composition suitably comprises no more than 0.001 wt % of said component, suitably no more than 0.0001 wt % of said component, suitably no more than 0.00001 wt %, suitably no more than 0.000001 wt %, suitably no more than 0.0000001 wt % thereof, most suitably no more than 0.0001 parts per billion (by weight).

The term "entirely free", when used in relation to a given component of a composition (e.g. "a liquid pharmaceutical composition entirely free of compound X"), refers to a composition containing none of said component.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm).

Suitably, unless stated otherwise, where reference is made to a boiling point, a melting point, or a glass transition (softening) temperature of a component, such reference refers to said parameter being measured at standard ambient pressure. Standard ambient pressure is an absolute pressure of 100 kPa (14.504 psi, 0.978 atm).

General Points and Advantages Relating to the Invention

The present invention uses a temporary plasticiser in an extrudable composition. Said extrudable composition is used to prepare an extruded item, and/or to produce another form of the extrudable composition. The temporary plasticiser reduces (temporarily) the temperature required to extrude the extrudable composition compared to if no (or less) temporary plasticiser is present. Advantageously, the use of a temporary plasticiser is particularly well suited for components of the extrudable composition which are thermally sensitive, for example active ingredients, such as pharmaceutical, nutraceutical, and/or food supplement active ingredients which are prone to degradation upon heating. Consequently, it is possible to have higher loadings of thermally sensitive ingredients in the extrudable composition and the corresponding extruded item.

The use of the temporary plasticiser allows the extrudable composition to be extruded at a lower temperature compared to the equivalent composition containing none (or lower levels) of the temporary plasticiser. Post extrusion, the temporary plasticiser can be removed (or partially removed) so that the extruded item's composition (or alternative form of the extrudable composition, e.g. 3D-printable filament) is akin to the extruded equivalent composition although as a result of being able to use a lower extrusion temperatures lower levels of thermal degradation may be observed in the extruded item.

Advantageously, the temporary plasticiser lowers the glass transition (or softening) temperature of the extrudable composition. In addition, post or during extrusion, the temporary plasticiser is removed or partially removed. This results in the glass transition (or softening) temperature of the resulting product to be increased thereby changing the physical properties of the resulting product. For example, reducing the flexibility of the extruded item.

The present invention deploys extrusion to produce extruded items, in particular pharmaceutical dosage forms, though the skilled person will readily appreciate that the principles of the invention are readily applicable to nutraceuticals and food supplements. Types of extrusion include 3D-printer, which includes Fused Filament Fabrication (FFF) 3D-printing.

Standard extrusion components may include extrusion nozzles (for example nozzle such as those used in 3D printing, such as fused FFF 3D-printing, along with any relevant conveying and/or heating means that allows the extrudable composition to be printed onto a surface, typically in a sequential-layered fashion.

The methods of the invention overcome many of the shortcomings of extrusion processes. For example, a commonly used extrudable carrier, polyvinyl alcohol (PVA), can only be extruded at temperatures greater than 180° C. The use of permanent plasticisers, such as sorbitol, can lower the extrusion temperature of PVA to about 140° C. However, using water as a temporary plasticiser can further reduce the extrusion temperature of the PVA and sorbitol mixture to about 90° C. Advantageously the temporary plasticiser can be removed or partially removed after or during extrusion of the extruded product (e.g. extruded item and/or extrudable element). This means the levels of the temporary plasticiser can be reduced to a level suitable for the intended use of the extruded item, for example levels which are suitable for use in pharmaceutical, nutraceutical or food supplement products. Alternatively, and/or additionally, the level of the temporary plasticiser can be removed or partially removed in the extruded product (e.g. extruded item and/or extrudable element) thereby reducing the possibility that any components of the extruded product will react with the temporary plasticiser. Finally, the removal or partial removal of the temporary plasticiser alters the physical properties of the extruded product (e.g. extruded item and/or extrudable element), for instance, increasing the glass transition (softening) temperature of said item. This results in physical properties being altered, such as the brittleness/flexibility of the extruded product. Thus, the extruded product's physical and chemical properties can be optimised depending on said item's intended use (i.e., for use as medicament (e.g. extruded item) or as use in the preparation of an extruded item (e.g., extrudable element)).

The invention broadens the applicability of extrusion (including 3D printing) to a wider range of physical forms, allowing components (including extrudable carrier and/or active ingredient) to be extruded with minimal thermal degradation of said components.

Though chemical and physical compatibilities between the temporary plasticiser and the other components of the extrudable composition (for example the extrudable carrier, if present the active ingredient, if present a permanent plasticiser and if present other components) must be considered when developing extruded items.

The present invention embeds an embeddable substance within a solidifiable body substance. Advantageously, the method to prepare the embedded item is performed at ambient temperature or requires heating to relatively low temperatures, such as to 40° C. As such, the method to prepare embedded items is particularly well suited for use with components which are thermally sensitive, for example, with thermally sensitive active ingredients such as biologic active ingredients (i.e., proteins, amino acids, peptides etc). Advantageously, the embeddable substance may be in a liquid like state (e.g. a liquid, a solution, a semi-solid (suitably a gel or gellable substance), an emulsion, a solid, or a suspension) within the solidifiable body substance. This may result in the embedded item having broad applicability with a number of active ingredients.

Suitably, the embedding step of each portion of the embeddable substance is digitally controlled, i.e., by a computer. Advantageously, embedding the embeddable substance in portions results in less variation during the embedding process of the amount of the embeddable substance dispensed, therefore resulting in a more accurate dose of the embeddable substance within the embedded item.

The present invention deploys embedding (suitably using a 3D printer) to produce embedded items, in particular pharmaceutical dosage forms, though the skilled person will readily appreciate that the principles of the invention are readily applicable to nutraceuticals and food supplements.

Extruded items and embedded items of the invention can be produced "on-demand", and in an individualised and customised manner to suit the needs of particular consumers (i.e., patients), thereby avoiding certain undesirable medical compromises (e.g. patients receiving imperfect dosages due to the limited range of sizes of mass-produced dosage forms on offer).

It is expected that the present invention will make a significant contribution to the art in terms of the production, dispensing, and consumption of pharmaceutical products, and this will have positive health impacts for all concerned.

It will be appreciated that, though the technology of the present invention is described herein in relation to solid dosage forms (especially pharmaceutical dosage forms), the technology is applicable more generally and can be effectively deployed to produce a range of solid items, be them extruded items or embedded items, of a variety of shapes and sizes. Moreover, the technology may be exploited beyond the confines of 3D-printing and/or hot-melt extrusions, and may be used on an industrial scale, for instance in large scale manufacturing facilitates, whether in batch production, continuous flow production, or a combination thereof.

It will be appreciated that the term solid dosage form includes dosage forms which may be filled with a fluid-like substance (i.e., a liquid, a solution, an emulsion, a suspension, or a semi-solid such as a gel) within the body of the dosage form and the body of the dosage form provides the structure of the dosage form. For example, an embedded item comprising a liquid embeddable substance is to be recognised as a solid dosage form.

It is to be understood, that the term solid dosage form also includes semi-solid dosage forms, for example, an embedded item comprising gelatine as the solidifiable body substance.

Method of Preparing an Extrudable Composition

The present invention provides a method of preparing an extrudable composition, suitably as defined herein.

The method suitably comprises:
 i. Mixing an extrudable carrier and a temporary plasticiser together; and
 ii. Optionally further processing the mixture from step i. to form:
   a. an extrudable fluid;
   b. an extrudable compressed form; or
   c. an extrudable element.

Suitably, there is provided a method of preparing an extrudable composition, the method comprising:
i. Mixing an extrudable carrier and a temporary plasticiser together; and
ii. Optionally further processing the mixture from step i. to form:
a. an extrudable fluid;
b. an extrudable compressed form; or
c. an extrudable element;
wherein the temporary plasticiser is a vaporisable substance (or combination of vaporisable substances) capable of being vaporised at a temperature at or below 150° C. (suitably at standard ambient pressure, e.g. 100 kPa).

Suitably mixing the extrudable carrier and the temporary plasticiser together is by shear mixing.

Suitably the mixing of the extrudable carrier and the temporary plasticizer together is performed at a mixing rate of greater than or equal to 10 rpm, 25 rpm, 50 rpm, 75 rpm, 100 rpm, 125 rpm, 150 rpm, 175 rpm, 200 rpm, 250 rpm, 300 rpm, 400 rpm, or 500 rpm. Suitably, the mixing of the extrudable carrier and the temporary plasticiser together is performed at a mixing rate of less than or equal to 500 rpm, 400 rpm, 300 rpm, 200 rpm, or 100 rpm. Suitably the mixing of the extrudable carrier and the temporary plasticiser together is performed at a mixing rate of 10 to 500 rpm.

Suitably the mixing of the extrudable carrier and the temporary plasticiser together is performed at room temperature. Suitably the mixing of the extrudable carrier and the temporary plasticiser together is performed at a temperature greater than or equal to 10° C., 20° C., 25° C., 30° C., 40° C., 50° C., 60° C., 70° C., 80° C., 90° C., or 100° C. Suitably the mixing of the extrudable carrier and the temporary plasticiser is performed at a temperature less than or equal to 100° C., 90° C., 80° C., 70° C., 60° C., 50° C., 40° C., 30° C., 25° C., 20° C., or 10° C. Suitably the mixing of the extrudable carrier and the temporary plasticiser is performed at a temperature of 10-100° C.

Suitably the mixing of the extrudable carrier and the temporary plasticiser together is performed at a temperature less than the boiling point of the temporary plasticiser. Suitably the mixing of the extrudable carrier and the temporary plasticiser together is performed at a temperature greater than the melting point of the temporary plasticiser. Suitably the mixing of the extrudable carrier and the temporary plasticiser together is performed at a temperature which is between the boiling point and the melting point of the temporary plasticiser.

Suitably the method further comprises spraying the temporary plasticiser on to the extrudable carrier during the mixing step.

Suitably the method further comprises further processing of the mixture from step i. to form an extrudable fluid. Suitably the extrudable fluid is an extrudable semi-fluid. Suitably the extrudable fluid is a molten extrudable composition. Suitably the extrudable fluid has properties suitable for direct use in extrusion. Advantageously, the extrudable fluid can be used in the process to prepare an extruded item without further processing of the extrudable composition, i.e., the extrudable fluid can be extruded without the need to manipulate the physical properties of the extrudable composition, for example, by (further) heating of the extrudable composition.

Suitably the extrudable fluid is obtained by heating the mixture from step i. to a temperature greater than or equal to the melting point or the glass transition (softening) temperature of the mixture, suitably greater than or equal to 20° C., 30° C., 40° C., 50° C., 60° C., 70° C., 80° C., 90° C., 100° C., 110° C., or 120° C. Suitably the extrudable fluid is obtained by heating the mixture from step i. to a temperature less than or equal to 200° C., 180° C., 160° C., 150° C., 140° C., 130° C., 120° C., 110° C., or 100° C. Suitably the extrudable fluid is obtained by heating the mixture from step i. to a temperature of 20 to 200° C.

Advantageously, a container, such as a syringe or a cartridge, can be filled with the extrudable composition. Suitably the method further comprises filling a container, such as a syringe or a cartridge, with the extrudable composition. Suitably, the method further comprises filling a container, such as a syringe or a cartridge, with the mixture from step i, optionally followed by further processing of the mixture from step i. to form the extrudable fluid in the container, for example by heating of the container. Suitably, the method comprises heating the container (e.g. a syringe) to a temperature greater than the glass transition (softening) temperature of the mixture formed in step i. Suitably, the method comprises heating the container (e.g. a syringe) to a temperature greater than or equal to 25° C., 30° C., 40° C., 50° C., 60° C., 70° C., 80° C., 90° C., or 100° C. Suitably, the method comprises heating the container (e.g. a syringe) to a temperature of 25-100° C. Suitably, the method further comprises filling a container with the extrudable fluid, for example suitably filling a syringe with the extrudable fluid. Suitably the extrudable fluid is optimised for syringe delivery, for example, the viscosity of the extrudable fluid allows the fluid to flow from the syringe when pressure is applied to the syringe. Advantageously, the syringe can be used to extrude the extrudable composition. In an embodiment, the container is a metal syringe, Suitably the method further comprises further processing of the mixture from step i. to form an extrudable compressed form, such as a tablet or a plurality of tablets, for example a mini-tablet(s). Suitably the extrudable compressed form is formed by compressing the mixture from step i. Suitably the compressing step utilises a punch tool. Suitably the punch tool has diameter of 1 to 10 mm, 2 to 8 mm, 4 to 7 mm, 5 to 7 mm, or about 6 mm. Suitably the punch tool is circular, oval, square or rectangular.

Suitably each extrudable compressed form is formed by compressing 10 to 100 mg, 20 to 80 mg, 30 to 70 mg, 40 to 60 mg, or about 50 mg of the mixture from step i per extrudable compressed form.

Suitably each extrudable compressed form has a weight of 10 to 100 mg, 20 to 80 mg, 30 to 70 mg, 40 to 60 mg, or about 50 mg.

Suitably the method further comprises further processing of the mixture from step i. to form an extrudable element. Suitably the extrudable element is a filament. Suitably the method comprises extruding the mixture from step i. to form an extrudable element. Suitably the extrusion temperature is greater than or equal to the glass transition (softening) temperature of the mixture from step i., for example, suitably greater than or equal to −50° C., −30° C., −10° C., 0° C., 10° C., 20° C., 30° C., 40° C., 50° C., 60° C., 70° C., 80° C., 90° C., 100° C., 110° C., or 120° C. Suitably the extrusion temperature is less than or equal to 200° C., 180° C., 160° C., 140° C., 130° C., 120° C., 110° C., 100° C., or 90° C. Suitably the extrusion temperature is between −50° C. and 200° C., 60° C. and 100° C., 65° C. and 95° C., or 70° C. and 90° C.

Suitably the extrusion step uses a hot melt extruder. Suitably the hot melt extruder comprises an extrusion nozzle. Suitably the extrusion nozzle comprises an output opening. The output opening is suitably dimensioned for the properties of the corresponding extrudable composition to allow molten extrudable composition to be deposited therefrom (e.g. onto a build platform). Suitably the output opening has a diameter of 50 to 2000 μm, 100 to 1500 μm, 200 to 1500 μm, 500 to 1500 μm, 750 to 1250 μm, or about 1000 μm. In an embodiment, the nozzle has an output opening with a diameter between 750 and 1250 μm.

Suitably the extrudable element (e.g. filament) has a thickness (i.e. diameter or maximum thickness) of between 0.1 mm and 5 mm, 0.5 mm and 2 mm, 0.5 mm and 1.5 mm, or 0.8 mm and 1.2 mm. In a particular embodiment, the filament has a thickness of about 1 mm. However, the thickness may be adjusted to suit the extrusion nozzles (in particular the size/diameter of the respective openings thereof) through which they are to be extruded.

Suitable the mixture from step i. is mixed at a mixing rate of greater than or equal to 10 rpm, 25 rpm, 35 rpm, 50 rpm, 75 rpm, 100 rpm, 125 rpm, 150 rpm, 175 rpm, 200 rpm, 250 rpm, 300 rpm, 400 rpm, or 500 rpm during the extruding step. Suitably, the mixture from step i. is mixed at a mixing rate of less than or equal to 500 rpm, 400 rpm, 300 rpm, 200 rpm, or 100 rpm. Suitably, the mixture from step i. is mixed at a mixing rate of 10 to 500 rpm during the extruding step.

Suitably the method further comprises coating the extrudable element with a lubricant and/or glidant. Suitable lubricants may include silica; fats, e.g. vegetable stearin; magnesium stearate or stearic acid; and/or talc. Suitable glidants may include fumed silica, talc, magnesium carbonate, and/or colloidal silica. The lubricant facilitates flow of the extrudable element through the extruder during the preparation of the extruded item.

Suitably the extruding step to form the extrudable element can optionally further comprises a step removing or partially removing the temporary plasticiser via vaporisation. Suitably the temporary plasticiser is removed or partially removed by heating the extrudable element and/or holding the extrudable element under a vacuum. Suitably the extrudable element is heated and/or held under vacuum until the properties (e.g. flexibility) of the extrudable element is suitable for use in the method to prepare the extruded item (e.g. solid dosage form). Suitably the extrudable element is heated and/or held under vacuum until the glass transition (softening) temperature of the extrudable element is between −50° C. and 100° C., −40° C. and 80° C., −40° C. and 75° C., −40° C. and 60° C., −40° C. and 50° C., −40° C. and 30° C., −20° C. and 50° C., −35° C. and 25° C., −30° C. and 25° C., −25° C. and 25° C., −20° C. and 25° C., −20° C. and 20° C., −20° C. and 15° C., −20° C. and 10° C., −20° C. and 5° C., −20° C. and 0° C., −20° C. and −5° C., −15° C. and −5° C., −15° C. and −10° C., or −12° C. and −8° C. Suitably the extrudable element is heated and/or held under vacuum until the glass transition (softening) temperature of the extrudable element is less than or equal to 70° C., 60° C., 50° C., 40° C., 30° C., 20° C., 10° C., 5° C., 0° C., −5° C., −10° C., −15° C., or −20° C. Suitably the extrudable element is heated and/or held under vacuum until the glass transition (softening) temperature of the extrudable element is about −10° C., or about 15° C.

Suitably the extrudable element is heated and/or held under vacuum until there is less than or equal to 20%, 16% weight, 14% weight, 12% weight, 10% weight, 8% weight, 6% weight, 5% weight, 4% weight, 3% weight, 2% weight, 1%, 0.5%, 0.1%, or 0.05% weight of the temporary plasticiser or until substantially free of the temporary plasticiser. Suitably the extrudable element is heated and/or held under vacuum until there is between 0-20% weight of the temporary plasticiser.

Suitably the extrudable element is heated and/or held under vacuum until the temporary plasticiser content of the extrudable composition has reduced by at least 10%, 20%, 30%, 40%, 50%, 60%, 70%, 80%, or 90%.

Suitably the extrudable element is heated and/or held under vacuum for greater than or equal to 10 minutes, 20 minutes, 30 minutes, 40 minutes, 50 minutes, 60 minutes, 90 minutes, or 120 minutes. Suitably the extrudable element is heated and/or held under vacuum for less than or equal to 120 minutes, 100 minutes, 80 minutes, or 60 minutes. Suitably the extrudable element is heated and/or held under vacuum for 10-120 minutes Suitably the extrudable element is heated. Suitably the extrudable element is heated to a temperature less than the melting point of the extrudable element. Suitably the extrudable element is heated to a temperature of greater than or equal 30° C., suitably greater than or equal to 40° C., 50° C., 60° C., 70° C., 80° C., 90° C., or 100° C. Suitably the extrudable element is heated to a temperature of less than or equal to 200° C., suitably less than or equal to 180° C., 160° C., 140° C., 130° C., 120° C., 110° C., 100° C., 90° C., or 80° C. Suitably the extrudable element is heated to a temperature of 30-200° C.

Suitably the extrudable element is held under reduced pressure, suitably a vacuum. Suitably the vacuum has a pressure less than atmospheric pressure, suitably less than or equal to 90 kPa, 10 kPa, 5 kPa, 1 kPa, 0.5 kPa, 0.1 kPa, 0.05 kPa, 0.01 kPa, or 0.005 kPa. Suitably the vacuum has a pressure of 0.005-90 kPa.

Suitably the temporary plasticiser is removed or partially removed by exposing the extrudable element to a relative humidity less than ambient relative humidity (RH), suitably less than or equal to 60% RH, 50% RH, 40% RH, 30% RH, 20% RH, 10% RH, or about 0% RH. Suitably the temporary plasticiser is removed or partially removed by exposing the extrudable element to a relative humidity of 0 to 60% RH.

Suitably, there is provided a method of processing an extrudable composition to produce an extrudable fluid, the method comprising melting or softening (suitably through heating) the extrudable composition.

Suitably, there is provided a method of processing an extrudable composition to produce an extrudable compressed form, the method comprising compressing the extrudable composition.

Suitably, there is provided a method of processing an extrudable composition to produce an extrudable element, the method comprising extruding or moulding the extrudable composition into an extrudable element.

Suitably, there is provided a method of converting an extrudable fluid to an extrudable compressed form.

Suitably, there is provided a method of converting an extrudable fluid to an extrudable element.

Suitably, there is provided a method of converting an extrudable compressed form to an extrudable fluid.

Suitably, there is provided a method of converting an extrudable compressed form to an extrudable element.

Suitably, there is provided a method of converting an extrudable element to an extrudable compressed form.

Suitably, there is provided a method of converting an extrudable element to an extrudable fluid.

Suitably the further processing step comprises converting the extrudable fluid to the extrudable compressed form. Suitably the further processing step comprises converting the extrudable fluid to the extrudable element. Suitably the further processing step comprises converting the extrudable compressed form to the extrudable fluid. Suitably the further processing step comprises converting the extrudable compressed form to the extrudable element. Suitably the further processing step comprises converting the extrudable element to the extrudable compressed form. Suitably the further processing step comprises converting the extrudable element to the extrudable fluid.

Suitably the further processing step comprises converting the extrudable fluid to the extrudable compressed form followed by converting the extrudable compressed form to the extrudable element. Suitably the further processing step comprises converting the extrudable fluid to the extrudable element followed by converting the extrudable element to the extrudable compressed form. Suitably the further processing step comprises converting the extrudable compressed form to the extrudable fluid followed by conversion of the extrudable fluid to the extrudable element. Suitably the further processing step comprises converting the extrudable compressed form to the extrudable element followed by conversion of the extrudable element to the extrudable fluid. Suitably the further processing step comprises converting the extrudable element to the extrudable compressed form followed by conversion of the extrudable compressed form to the extrudable fluid. Suitably the further processing step comprises converting the extrudable element to the extrudable fluid followed by conversion of the extrudable fluid to the extrudable compressed form.

Suitably the converting step comprises heating, compressing, dry-compressing, wet-compressing, moulding and/or extruding. Suitably, the extrudable composition is transformed into the form of an extrudable fluid by heating. Suitably, the extrudable composition is transformed into the form of an extrudable element by extruding. Suitably, the extrudable composition is transformed into the form of an extrudable compressed form by compressing, dry compressing, and/or wet-compressing.

Suitably, the extrudable compressed form of the extrudable composition is transformed into the form of an extrudable fluid, suitably via heating.

Suitably the extrudable compressed form of the extrudable composition is transformed into the form of an extrudable element, such as a filament for 3D printing, suitably via extrusion.

Suitably the further processing step comprises converting the extrudable compressed form (e.g. a tablet) to the extrudable element (e.g. a filament for 3D printing) by extruding the extrudable compressed form.

Suitably the further processing step comprises converting the extrudable compressed form (e.g. a tablet) to the extrudable fluid by heating the extrudable compressed form.

Suitably the further processing step comprises converting the extrudable fluid to the extrudable element (e.g. a filament for 3D printing) by extruding the extrudable fluid.

Suitably the further processing step comprises converting the extrudable element (e.g. a filament for 3D printing) to the extrudable fluid by heating the extrudable element.

Suitably the method comprises compressing the extrudable composition to form an extrudable compressed form.

Suitably the method comprises mixing followed by compressing the components of the extrudable composition together to form an extrudable compressed form.

Suitably the method comprises compressing the components of the extrudable composition together to form an extrudable compressed form followed by extruding the compressed form to form an extrudable element (e.g. a filament for 3D printing).

Suitably the method comprises mixing followed by compressing the components of the extrudable composition together to form an extrudable compressed form followed by extruding the compressed form to form an extrudable element.

It will be understood that any of the aforesaid aspects and embodiments may be achieved with or without the inclusion of (or mixing together with) a temporary plasticizer, and such aspect and embodiments are also considered within the scope of the present invention. For instance, the present invention provides a method of preparing an extrudable composition, the method comprising:
  i. Providing an extrudable carrier, optionally mixed with a drug substance or active; and
  ii. Optionally further processing the mixture from step i. to form:
    a. an extrudable fluid;
    b. an extrudable compressed form; or
    c. an extrudable element.

In such aspects, step ii may for instance comprise softening, melting, or otherwise mobilising an initial extrudable composition (which is suitably initially in a solid form), for instance an extrudable powder, extrudable granules, extrudable compressed forms (be it monolithic or a plurality of compressed forms, such as minitablets), to produce an extrudable fluid. Such mobilising of the initial extrudable composition may comprise heating said composition, suitably in situ within a dispenser (e.g. a syringe, suitably a metal syringe with a heating jacket), such that said composition may then be extruded into an extrudable element (e.g. filament) or directly into an extruded item (e.g. tablet, suitably via direct ink 3D printing).

Alternatively, in such aspects, step ii may for instance comprise compressing an initial extrudable composition (suitably a granular or powder composition) to form an extrudable compressed form. Said extrudable compressed form may be fed back into said method to produce an extrudable fluid, an extrudable element, or even an extrudable item (e.g. by direct ink 3D printing), with or without being supplemented or mixed with a temporary plasticizer.

Alternatively, in such aspects, step ii may for instance comprise extruding an initial extrudable composition (which may be in the form of an extrudable powder, extrudable granules, extrudable compressed form(s)) into an extrudable element.

Suitably, whenever the invention is performed without using a temporary plasticizer, suitably any extrusions are performed at a temperature between 40 and 120° C., suitably at a temperature between 60 and 100° C.

All optional features described above and hereinafter in relation to aspects or embodiments involving the use of a temporary plasticizer, apply equally to aspect or embodiments without a temporary plasticizer unless incompatible in the given context.

Method of Preparing an Extruded Item

The present invention provides a method of preparing an extruded item, suitably as defined herein.

The method suitably comprises:
  i. providing an extrudable composition comprising an extrudable carrier; and
  ii. extruding an extrudable composition into a desired form optionally in association with one or more supplementary elements (e.g. a shell, coating, core);
  wherein:
  the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

The method suitably comprises:

i. providing an extrudable composition comprising an extrudable carrier; and ii. extruding an extrudable composition into a desired form optionally in association with one or more supplementary elements (e.g. a shell, coating, core);

wherein:

the extrudable composition initially comprises greater than or equal to 5% weight of a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

Suitably, the method suitably comprises:

i. providing an extrudable composition comprising an extrudable carrier; and ii. 3D-printing an extrudable composition into a desired form optionally in association with one or more supplementary elements (e.g. a shell, coating, core);

wherein:

the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

Suitably the desired form is a solid dosage form, suitably a solid oral dosage form. Suitably the extruded item is a pharmaceutical, nutraceutical, or food supplement solid dosage form. Suitably, the extruded item comprises at least one active ingredient, suitably at least one pharmaceutically, nutraceutically, or food supplement active ingredient. Most suitably the active ingredient is a pharmaceutically active ingredient.

There is provided a method of preparing a pharmaceutical, nutraceutical, or food supplement solid dosage form, the method comprising:

i) providing an extrudable composition comprising an extrudable carrier; and ii) extruding the extrudable composition into a desired form optionally in association with one or more supplementary elements (e.g. a shell, coating, core);

wherein:

the extrudable composition initially comprises a temporary plasticiser, the temporary plasticiser being a vaporisable substance (or combination of vaporisable substances) capable of being vaporised at a temperature at or below 150° C. (suitably at standard ambient pressure, e.g. 100 kPa); and the method further comprises removing or partially removing the temporary plasticizer, via vaporisation.

Suitably, there is provided a method of preparing a pharmaceutical, nutraceutical, or food supplement solid dosage form, the method comprising:

i) providing an extrudable composition comprising an extrudable carrier; and ii) extruding the extrudable composition into a desired form optionally in association with one or more supplementary elements (e.g. a shell, coating, core);

wherein:

the extrudable composition initially comprises a temporary plasticiser, the temporary plasticiser being a vaporisable substance (or combination of vaporisable substances) capable of being vaporised at a temperature at or below 150° C. (suitably at standard ambient pressure, e.g. 100 kPa); and the method further comprises removing or partially removing the temporary plasticizer, via vaporisation.

Suitably, there is provided a method of preparing a pharmaceutical, nutraceutical, or food supplement solid dosage form, the method comprising:

i) providing an extrudable composition comprising an extrudable carrier; and ii) extruding the extrudable composition, via 3D printing, into a desired form optionally in association with one or more supplementary elements (e.g. a shell, coating, core);

wherein:

the extrudable composition initially comprises a temporary plasticiser, the temporary plasticiser being a vaporisable substance (or combination of vaporisable substances) capable of being vaporised at a temperature at or below 150° C. (suitably at standard ambient pressure, e.g. 100 kPa); and the method further comprises removing or partially removing the temporary plasticizer, via vaporisation.

Suitably the extrudable composition is as herein defined. Suitably the extrudable composition initially comprises at greater than or equal to 0.1%, 0.2%, 0.5%, 0.8% 1%, 2%, 3%, 4%, 5%, 6%, 7%, 8%, 9%, 10%, 12%, 15%, 18%, 20%, 25% or 30% weight of a temporary plasticiser. Suitably the extrudable composition initially comprises 0.1 to 25% weight of a temporary plasticiser.

The method suitably comprises operating the extrusion apparatus to produce an extruded item, suitably upon the build platform, through the extrusion of the extruded item thereinto. Suitably, such production is performed via a computer-implemented process (i.e. where extrusion is controlled and suitably initiated by a computer that is connected or connectable to or within the apparatus, be it in a wired or wireless fashion).

Suitably the extrusion apparatus comprises a container for containing the extrudable composition prior to the extruding step, and a nozzle for dispensing the extrudable composition during the extruding step, wherein the container is heated at a temperature to maintain the extrudable composition in a (substantially) fluid state.

The method suitably involves extruding an extrudable composition onto a build platform. Such extrusion suitably involves 3D printing, preferably FFF 3D-printing. As such, the extrusion may comprise extruding with one or more extrudable compositions. The extrudable composition (or precursor thereof) is suitably extruded via the extrusion nozzle of the extrusion apparatus of the invention.

The extrusion of an extrudable composition onto a build platform is suitably performed by an extruder (for example a 3D-printer), suitably with one or more extrudable compositions. Such extrudable composition(s) are suitably extruded via an extrusion nozzle as herein described.

Initially, an extrudable composition (or precursor thereof) suitably resides within the apparatus in a storage position, suitably within a cartridge such as a filament spool. The extrudable composition is suitably conveyed via one or more conveyors (e.g. rollers) to the extrusion nozzle. The extrudable composition is then extruded through the extrusion nozzle (suitably whilst extrudable composition continues to be conveyed towards the extrusion nozzle from a storage position). Extrusion through the extrusion nozzle suitably involves melting and/or softening the extrudable composition to allow it to be deposited onto the build platform, suitably in a layer-by-layer fashion. Suitably the relevant extrudable composition solidifies after being deposited onto the build platform or onto a layer that has already been extruded upon the build platform. Suitably a 3D shape is constructed in a layer-by-layer fashion through judicious depositing according to a pre-defined blueprint. Suitably after or during extrusion the temporary plasticiser is removed or partially removed. Suitably the temporary plasticiser is removed or partially removed by exposing the extruded extrudable composition to a temperature above ambient and/or to a vacuum.

The extrusion nozzle is suitably heated at an operating temperature as herein described to facilitate melting and/or softening of an extrudable composition. The nozzle suitably extrudes the extrudable composition at one or more of the operating speeds herein described.

The extrusion nozzle is suitably moved during the extrusion suitably in any or all of the X, Y, Z direction.

Once extruded, the extruded item suitably rests on the build platform, suitably resembling a solid dosage form.

Suitably, a plurality of extruded items are printed upon the build platform.

It will be understood by those skilled in the art that the, each, or any extrusion nozzle may be adapted to suit the properties a corresponding extrudable composition configured to extrude thereto. The nozzle properties/design and extrudable composition properties suitably complement one another so as to facilitate controlled extrusion of said composition (be it continuous or intermittent, e.g. where more than one extrudable composition is used in the extrusion of an extruded item), suitably without any nozzle blockages or impedance, and suitably without any unacceptable degradation of ingredients within the extrudable composition during the extrusion process.

In an embodiment, the composition of the extruded item comprises less temporary plasticiser than the extrudable composition used to prepare the extruded item.

Extruding Step

Suitably the extruding step is performed at a temperature greater than the glass transition temperature of the extrudable composition. Suitably the extruding step is performed at a temperature greater than or equal to $-50°$ C., $-30°$ C., $-10°$ C., $0°$ C., $10°$ C., $20°$ C., $30°$ C., $40°$ C., $50°$ C., $60°$ C., $70°$ C., $80°$ C., $90°$ C., $100°$ C., $110°$ C., $120°$ C., $130°$ C., $140°$ C., or $150°$ C. Suitably the extruding step is performed at a temperature less than or equal to $200°$ C., $180°$ C., $160°$ C., $150°$ C., $140°$ C., $130°$ C., $120°$ C., $110°$ C., $100°$ C., or $90°$ C. Suitably the extruding step is performed at a temperature of $-50$ to $200°$ C.

Suitably the extruding step uses an extruder. Suitably the extruder is a 3D-printer. Suitably the 3D-printer is a FFF 3D-printer. Suitably the extruding step uses direct ink printing. Suitably the extruding step uses a syringe, suitably a heated syringe. Suitably the syringe or the heated syringe contains the extrudable composition, suitably the extrudable composition is a blend or an extrudable fluid.

Suitably the extruding step comprises extruding the extrudable composition to form a first layer of the extruded item and optionally followed by extruding the extrudable composition to form subsequent layer(s). Suitably each layer has a thickness of between 10 and 1000 µm, between 20 and 800 µm, between 30 and 500 µm, between 40 and 300 µm, between 50 and 200 µm, between 100 and 200 µm, between 125 and 200 µm, between 140 and 190 µm, between 155 and 175 µm, between 250 and 350 µm, between 750 and 850 µm, about 166 µm, about 300 µm, or about 800 µm. Suitably each layer of the extruded item can have the same thickness or each layer can have a different thickness. Advantageously, having a thicker first layer (i.e., the layer which contacts the build platform) may result in greater adherence of the extruded item during its production.

Suitably the extruding step uses a 100% infill. Suitably the extruding step uses a concentric fill pattern.

The method comprises removing or partially removing the temporary plasticiser via vaporisation. Suitably, the temporary plasticiser is removed or partially removed from the extruded item prior (i.e., from the extrudable composition such as an extrudable element), during and/or after the step of extruding. Suitably, the temporary plasticiser is removed or partially removed from the extruded item during and/or after the step of extruding. Suitably, the temporary plasticiser is removed or partially removed from the extruded item after the step of extruding. Suitably at least 10%, 20%, 30%, 40%, 50%, 60%, 70%, 80%, or 90% of the temporary plasticiser is removed. Suitably between 10 to 90% of the temporary plasticiser is removed. Suitably the temporary plasticiser is removed or partially removed until there is less than or equal to 20% weight, 16% weight, 14% weight, 12% weight, 10% weight, 8% weight, 6% weight, 5% weight, 4% weight, 3% weight, 2% weight, 1% weight, 0.5% weight, or 0.1% weight of the temporary plasticiser in the extruded item. Suitably the extruded item is substantially free of the temporary plasticiser. Suitably the extruded item is entirely free of the temporary plasticiser. Suitably the temporary plasticiser is removed or partially removed until there is 0 to 20% weight of the temporary plasticiser in the extruded item Suitably the step of removing or partial removing of the temporary plasticiser comprises heating and/or holding under reduced pressure, such as a vacuum, the extrudable composition (suitably an extrudable element) and/or the extruded item (during the formation of the extruded item or after the extruded item has been formed). Suitably the extrudable composition and/or extruded item is heated to a temperature of greater than or equal $30°$ C., $40°$ C., $50°$ C., $60°$ C., $70°$ C., $80°$ C., $90°$ C., or $100°$ C. Suitably the extrudable composition and/or the extruded item is heated to a temperature of less than or equal to $200°$ C., $180°$ C., $160°$ C., $140°$ C., $130°$ C., $120°$ C., $110°$ C., $100°$ C., $90°$ C., or $80°$ C. Suitably the extrudable composition and/or the extruded item is heated to a temperature of 30 to $200°$ C. Suitably the extrudable composition and/or the extruded item is held under reduced pressure such as under a vacuum. Suitably the vacuum has a pressure less than atmospheric pressure, suitably less than or equal to 90 kPa, 10 kPa, 5 kPa, 1 kPa, 0.5 kPa, 0.1 kPa, 0.05 kPa, 0.01 kPa, or 0.005 kPa. Suitably the vacuum has a pressure of 0.005-90 kPa.

Suitably, the extrudable composition is as herein defined.

Suitably step i. further comprises extruding the extrudable composition onto a build platform. Suitably the build platform is held at a temperature which is lower than the extrusion temperature. Suitably the build platform is held at a temperature of less than or equal to $100°$ C., suitably less than or equal to $90°$ C., $80°$ C., $70°$ C., $60°$ C., $50°$ C., $40°$ C., or $30°$ C. Suitably the build platform is held at a temperature of 0 to $100°$ C., such as 30 to $100°$ C. Advantageously, having the temperature of the build platform less than the extrusion temperature helps to solidify the extruded item as it is being formed. Additionally, having the temperature of the build platform above ambient aids in the removal or partial removal of the temporary plasticiser.

Suitably the extruded item is heated by the build platform until the extruded item contains less than or equal to 20% weight, 16% weight, 14% weight, 12% weight, 10% weight, 8% weight, 6% weight, 5% weight, 4% weight, 3% weight, 2% weight, 1% weight, 0.5% weight, or 0.1% weight of the temporary plasticiser, or is substantially free of the temporary plasticiser, or is entirely free of the temporary plasticiser. Suitably the extruded item is heated by the build platform until the extruded item contains between 0 and 20% weight of the temporary plasticiser.

Suitably the extruded item is heated by the build platform until the temporary plasticiser content of the extruded item has reduced by at least 10%, 20%, 30%, 40%, 50%, 60%, 70%, 80%, or 90% relative to the temporary plasticiser content of the extrudable composition. Suitably the extruded item is heated by the build platform until the extruded item is substantially free or entirely free of the temporary plasticiser. Suitably the extruded item is heated by the build platform until the temporary plasticiser content has reduced by 10 to 100%, such as 10 to 90% relative to the temporary plasticiser content of the extrudable composition.

Suitably the extruder comprises an extrusion nozzle. Suitably the extrusion nozzle comprises an input opening (into which the extrudable composition is fed) and an output opening (out of which molten extrudable composition is deposited). The input opening is suitably dimensioned to receive the extrudable composition (e.g. an extrudable element, blend of extrudable composition components, an extrudable fluid or an extrudable compressed form) therethrough. Suitably the input opening has a diameter of 0.1 to 100 mm, 0.2 to 10 mm, 0.5 to 5 mm, 0.5 to 1.5 mm, 1.0 to 2.5 mm, 1.5 to 2.0 mm, 0.75 to 1.25 mm, about 1.75 mm, or about 1 mm. The output opening is suitably dimensioned for the properties of the corresponding extruded item to allow molten extrudable composition to be deposited therefrom (e.g. onto a build platform). Suitably the output opening has a diameter of 0.01 to 10 mm, 0.05 to 5 mm, 0.1 to 1 mm, 0.1 to 0.8 mm, 0.2 to 0.6 mm, or about 0.4 mm. In an embodiment, the nozzle has an output opening with a diameter between 0.3 and 0.5 mm.

The feeding of extrudable composition(s) to and through their respective extrusion nozzle(s) is suitably facilitated by a conveyor (or roller) as described elsewhere herein. Such a conveyor is suitably situated along a path of an extrudable composition, suitably between an extrudable composition source (e.g. a filament spool or cartridge) and an extrusion nozzle to and through which the given extrusion composition is assigned to flow.

Suitably, prior to the extruding step the extrudable composition is in the form of or is transformed into the form of:
 a. an extrudable fluid;
 b. an extrudable compressed form; or
 c. an extrudable element.

Suitably the method comprises extruding the extrudable compressed form to form an extruded item. Suitably the method comprises extruding the extrudable fluid to form an extruded item. Suitably the method comprises extruding the extrudable element to form an extruded item.

The extrudable fluid, extrudable compressed form and extrudable element are as herein defined.

Suitably, prior to the extruding step the extrudable composition is in the form of or is transformed into the form of an extrudable fluid, suitably via heating, and the extrudable composition is thereafter directly extruded in a fluid state.

Suitably prior to the extruding step the extrudable composition is in the form of or is transformed into the form of an extrudable compressed form, suitably a plurality of tablets.

Suitably prior to the extruding step the extrudable compressed form of the extrudable composition is transformed into the form of an extrudable fluid, suitably via heating, and the extrudable composition is thereafter directly extruded in a fluid state.

Suitably, prior to the extruding step the extrudable compressed form of the extrudable composition is transformed into the form of an extrudable element, such as a filament for 3D printing, suitably via extrusion, and the extrudable element is thereafter directly extruded, suitably as a filament via a 3D printing nozzle.

Extruding from Dispensers

Suitably the method comprises providing a dispenser filled with the extrudable composition followed by extruding the extrudable composition into a desired form, wherein the extrudable composition is as defined herein.

Suitably, the method comprises providing a dispenser filled with an extrudable fluid. Suitably, the method comprises providing a dispenser filled with an extrudable compressed form or a plurality of extrudable compressed forms. Suitably, the method comprises providing a dispenser filled with an extrudable element.

Suitably the method comprises conveying the extrudable composition from the dispenser and through the extruder. Suitably, from the dispenser and to (and through) the extrusion nozzles.

Suitably the dispenser is a container, for example a cartridge, suitably a 3D-printer cartridge.

Suitably the container is a filament spool loaded with a filament.

Suitably the container is a syringe. Suitably the syringe is filled with an extrudable fluid.

Suitably, the method further comprises filling a container with the extrudable fluid, suitably filling a syringe with the extrudable fluid.

Suitably the extrudable fluid is formed in situ, by heating the container (e.g. a syringe) filled with the components of the extrudable composition. Suitably, the method comprises heating the container (e.g. a syringe) to a temperature greater than or equal to 25° C., 30° C., 40° C., 50° C., 60° C., 70° C., 80° C., 90° C., or 100° C. Suitably, the method comprises heating the container (e.g. a syringe) to a temperature of 25 to 100° C.

Suitably the extrudable fluid is extruded from the syringe (i.e., the syringe is acting as an extruder). Suitably the extrudable fluid is optimised for syringe delivery, for example, the viscosity of the extrudable fluid allows the fluid to flow from the syringe when pressure is applied to the syringe. Advantageously, extrusion of the extrudable fluid is performed in a single process. For example, the components of the extrudable composition can be added to the syringe, the syringe heated to form an extrudable fluid, followed directly by extrusion to form the extruded item. This direct extrusion reduces the overall exposure of the extrudable composition to elevated temperatures, for example, in comparison when an extrudable element (e.g. a filament) is used to prepare an extruded item, the components of the extrudable composition are first exposed to elevated temperatures during the process to prepare the element, followed by exposure to elevated temperatures during the process to prepare the extruded item.

Additional Method Steps

The method may include one or more further steps before, during, and/or after any of the aforesaid steps. The external surface(s) of the extruded item may be pre- or post-treated, whether through the extrusion of an additional layer or partial layer, or through alternative coating techniques well known in the art.

Suitably the method comprises extruding the extrudable composition into a desired form in association with one or more supplementary elements. Suitably the supplementary elements comprise a shell, a coating and/or core.

Suitably the method further comprises a step of incorporating at least one further excipient and/or at least one further active ingredient into the extruded item, suitably surrounding the desired form with the at least one further excipient and/or the at least one active ingredient. Suitably the desired form is the extruded item.

An extruded item produced via methods of the invention may be subsequently treated in a variety of ways to afford a further-processed extruded item. Suitably the method further comprises coating the product obtained from the extruding step. Suitably the coating is described herein. For instance, an extruded item may be enterically coated by standard enteric coating treatments known in the art. Likewise, other release-controlling properties may be imparted to an extruded item by further processing.

Most suitably, all steps (including any further processing steps) are performed by the extrusion apparatus. Suitably all steps (including further processing steps) are suitably controlled by the same computer.

Computer-Implementation of Method

The method of preparing an extruded item is suitably a computer-implemented method, suitably as defined herein.

The method suitably involves providing an extrusion apparatus, suitably as defined herein, and operating said apparatus to extrude the extrudable composition thereby forming the extruded item. Suitably the extrusion apparatus includes or is otherwise connected to a computer. Operating the extrusion apparatus suitably involves operating a computer, which is suitably connected (be it in a wired or wireless fashion) with or within the relevant extrusion apparatus (so as to allow the computer to control and co-ordinate other parts of the extrusion apparatus, including an extruder), to cause extrusion of an extrudable composition to form an extruded item and/or an extrudable element.

A computer that is comprised of or otherwise associated with an extrusion apparatus of the invention may be suitably referred to as an extrusion control computer. The extrusion control computer may serve a different function (and may be a distinct entity) to other "computers" referred to herein, such as monitoring computers and analytical computers, though a single computer may perform the function(s) of one or more of any combination of these computers. An extrusion control computer suitably controls the extruding of an extrudable composition through an extrusion nozzle, and optionally further processing steps, for example coating of the item formed after extrusion. Wherever a different computer is used to implement each of these operations, said computers are suitably co-ordinated and may thus be considered to be a part of one overall computer.

Extruding of extrudable composition(s) to form the extruded item(s) and/or extrudable element(s) is suitably controlled by a computer, running pursuant extrusion software, suitably based on information provided to the computer by user input(s) (drug type, drug dose level), databases (e.g. patient database and/or extruded item databases), and/or data files (e.g. design and/or parameter files), as described herein. Suitably an extrusion apparatus is configured to extrude pursuant to instructions provided by the computer by: feeding extrudable composition(s) to and through their respective extrusion nozzle(s) at the appropriate intervals and/or at the appropriate rates; heating the relevant extrusion nozzle(s) at the appropriate temperature(s) for the appropriate time; and by moving the extrusion nozzle(s) and/or build platform to enable systematic layer-by-layer extruding in accordance with the relevant information obtained and calculations made by the computer.

The extrusion nozzle(s) are suitably controlled by the computer according to the "obtained information" regarding the extruded item (e.g. design and/or other parameters). Extrusion nozzles are suitably controlled to extrude a given extrudable composition upon a build platform (or upon a partially build extruded item upon the build platform) to a pattern pre-defined by the "obtained information". As such, the or each extrusion nozzle may be controlled to switch "on" and "off" in accordance with a pre-defined schedule to deliver the required pattern in the construction of the extruded item. An extrusion nozzle may be switched "on" by causing an output opening to open, by adjusting the extrusion nozzle's operating temperature (e.g. increasing it so as to cause melting of the relevant extrudable composition), by operating the conveyor to feed extrudable composition through the nozzle, or a combination of any or all of the aforementioned. Naturally, an extrusion nozzle may be switched off by causing an output opening to close, by adjusting the extrusion nozzle's operating temperature (e.g. decreasing it to a temperature which does not cause melting of the relevant extrudable composition), by operating the conveyor to restrict or cease feeding of an extrudable composition through the extrusion nozzle, or a combination of any or all of the aforementioned. The temperature of the extrusion nozzle(s) are suitably set and controlled by the computer according to the properties of the extrudable composition in question, as described elsewhere herein. Suitably, the operating temperature of an extrusion nozzle through which an extrudable composition passes is between 50 and 220° C., between 60 and 150° C., or between 70 and 120° C. However, the operating temperature of an extrusion nozzle may be lower, for example less than 50° C., especially in systems that use extrudable compositions with low glass transition temperatures. Suitably, the extrusion nozzle temperature is set to at least 65° C., more suitably at least 70° C. In a particular embodiment, the extrusion nozzle temperature is 50-130° C., 60-120° C., 70-110° C., or 80-100° C. Suitably the operating temperature of an extrusion nozzle assigned to a given extrudable composition is lower than a corresponding extrudable composition having lower levels (i.e., substantially free) of the temporary plasticiser.

The build platform is suitably controlled by the computer according to the "obtained information" regarding the extruded item (e.g. design and/or other parameters), suitably as described elsewhere herein. This may include controlling the operating temperature of the build platform, in particular the operating temperature of the surface of the build platform. Suitably, during extrusion, the operating temperature of the build platform or surface thereof is maintained substantially constant, suitably at a constant temperature+/− 5° C. Such temperature control may facilitate removal or partial removal of the temporary plasticiser, cooling, and/or hardening of post-deposited extrudable composition(s) to thereby secure the structural integrity of the extruded item as it is being extruded. Such temperature control may facilitate adhesion of the developing extruded item to the surface of the build platform during extrusion. Such temperature control may facilitate release (i.e. unsticking) of an extruded item after extrusion (e.g. the surface of the build platform may be heated or cooled, as appropriate, to reduce adhesion of the extruded item(s) thereto). During extrusion, the build platform is suitably configured or operable to maintain a surface temperature (i.e. for the surface in contact with the extruded item) of less than or equal to 100° C., suitably less than or equal to 90° C., 80° C., 70° C., 60° C., 50° C., 40° C., or 30° C. During extrusion, the build platform is suitably configured or operable to maintain a surface temperature (i.e. for the surface in contact with the extruded item) of 30-100° C.

It will be appreciated that any of the aforesaid aspects and embodiments may be achieved with or without the use or inclusion of (or mixing together with) a temporary plasticizer, and such aspect and embodiments are also considered within the scope of the present invention. For instance, the present invention provides a method of preparing an extruded item, the method comprising:
i. providing an extrudable composition comprising an extrudable carrier, and optionally a drug substance or active; and
ii. extruding an extrudable composition into a desired form optionally in association with one or more supplementary elements (e.g. a shell, coating, core).

In such aspects, providing the extrudable composition may involve providing an extrudable solid form (e.g. powder, granules, minitablets, monolith) as hereinbefore described, though preferably involves providing an extrudable fluid, an extrudable compressed form, or an extrudable element as described herein. Particularly preferred is an extrudable compressed form, suitably in the form of a plurality of compressed units (e.g. minitablets) or a compressed monolith (e.g. such as a pre-compressed solid mass).

In such aspects, extruding the extrudable composition into a desired form (e.g. an oral dosage form) suitably comprises dispensing the extrudable composition from a dispense (e.g. syringe), suitably following sufficient mobilisation (e.g. melting by heating), suitably in situ within the syringe to allow for direct ink 3D printing.

All optional features described above and hereinafter in relation to aspects or embodiments involving the use of a temporary plasticizer, apply equally to aspect or embodiments without a temporary plasticizer unless incompatible in the given context.

Method of Preparing an Extrudable Composition and an Extruded Item

According to a further aspect of the present invention, there is provided a method of preparing an extruded item, the method comprising:
i. Mixing an extrudable carrier and a temporary plasticiser together; and
ii. Optionally further processing the mixture from step i. to form:
a. an extrudable fluid;
b. an extrudable compressed form; or
c. an extrudable element;
iii. Extruding the extrudable composition obtained from step i (or step ii. if applicable) into a desired form optionally in association with one or more supplementary elements (e.g. a shell, coating, core);
wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

In one embodiment, there is provided a method of preparing an extruded item, the method comprising:
i. Mixing an extrudable carrier and a temporary plasticiser together; and
ii. Optionally further processing the mixture from step i. to form:
a. an extrudable fluid;
b. an extrudable compressed form; or
c. an extrudable element;
iii. 3D-printing the extrudable composition obtained from step i (or step ii. if applicable) into a desired form optionally in association with one or more supplementary elements (e.g. a shell, coating, core);
wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

The features of the method steps are described elsewhere herein. For instance, method steps i. and ii., and method step iii. are described separately above.

It will be appreciated that any of the aforesaid aspects and embodiments may be achieved with or without the use or inclusion of (or mixing together with) a temporary plasticizer, and such aspect and embodiments are also considered within the scope of the present invention. For instance, the present invention provides a method of preparing an extruded item, the method comprising:
i. Providing an extrudable composition comprising an extrudable carrier, and optionally a drug substance or active; and
ii. Optionally further processing the mixture from step i. to form:
a. an extrudable fluid;
b. an extrudable compressed form; or
c. an extrudable element;
iii. Extruding the extrudable composition obtained from step i (or step ii. if applicable) into a desired form optionally in association with one or more supplementary elements (e.g. a shell, coating, core).

All optional features described above and hereinafter in relation to aspects or embodiments involving the use of a temporary plasticizer, apply equally to aspect or embodiments without a temporary plasticizer unless incompatible in the given context.

Extrusion Apparatus for Preparing an Extruded Item, and Associated Equipment and Software The present invention provides an extrusion apparatus for preparing (e.g. printing) an extruded item (e.g. a solid dosage form such as a tablet), suitably as defined herein, and suitably also comprises the extrudable composition as herein defined. The extrusion apparatus is suitably operable to form an extruded item (e.g. solid dosage form) via extruding the extrudable composition (suitably layer-by-layer) to product the extruded item.

Suitably the extrusion apparatus comprises an extrudable element. Suitably the extrusion apparatus comprises an extrudable fluid. Suitably the extrusion apparatus comprises an extrudable compressed form.

The extrusion apparatus is suitable for extruding an extrudable composition to form an extruded item, wherein the extrudable composition and the extruded item comprises at least one active ingredient.

Suitably the extrusion apparatus comprises a container for containing the extrudable composition, and a nozzle for dispensing the extrudable composition, wherein the container is heatable. Suitably, the container is heatable to a temperature of 25 to 300° C., 25 to 250° C., 25 to 200° C., or 25 to 150° C.

Extruder

The extrusion apparatus suitably comprises an extruder. Suitably the extruder is a 3D-printer. Suitably the 3D printer is a fused filament fabrication (FFF) 3D-printer. Such printers are often referred to as fabrication deposition Modelling™ (FDM) 3D printers. The extrusion apparatus suitably comprises a fused filament fabrication 3-dimensional printer (an FFF 3D printer).

Conventional extruders, including 3D-printers (including FFF 3D-printers), are known in the art, and are generally suitable for use with the present invention, though they may be judiciously modified based on the principles outlined herein to optimise extrusion of the extruded item. For the skilled persons reference, the following research articles describe a viable operation of FFF 3D printers—S. H. Masood, "Application of fused deposition modelling in controlled drug delivery devices", *Assembly Automation*, 27/3 (2007), p. 215-221 and Khaled et al, "Desktop 3D printing of controlled release pharmaceutical bilayer tablets", *International Journal of Pharmaceutics*, 461 (2014), p. 105-111—describe printing with FFF 3D printers of filaments, albeit there are no active ingredients contained within the filaments being printed (drug compounds are infused at a later stage). Furthermore, PCT publication WO2016/038356 by the present application, which is hereby incorporated by reference, also describes suitable equipment for use with the present invention.

Extruders suitable for use with the invention generally comprise a heated/heatable extruder nozzle which melts/softens and deposits (suitably onto a build platform) molten extrudable composition in a layer-by-layer fashion. The deposited molten composition suitably hardens rapidly following deposition. Maintaining a build platform with a relatively low surface temperature may facilitate such cooling/hardening to improve the final structure of the solid dosage form being printed., while maintaining a build platform with a surface temperature greater than ambient temperature facilitates the removal or partial removal of the temporary plasticiser. The extruder also suitably includes one or more nozzle heaters (suitably one associated with each nozzle but optionally one serving multiple nozzles) and suitably one or more conveyors (suitably one associated with each filament and/or nozzle) as defined herein. Suitably the extruder comprises one or more filament spool zones (or filament spool attachment points) for holding the relevant filament spool(s).

Suitably in the present invention drug compounds are formulated within extrudable composition(s) and extruded directly as an extruded item.

Suitably the extruder uses filaments as herein defined. Suitably the extrusion apparatus employs pre-fabricated filament(s) that are selectively extruded and deposited in a layer-by-layer printing process to produce the extruded item.

The extrusion apparatus of the invention may comprise one or more other components, optionally extruding, printing or dispensing materials intended to form a part of the extruded item. For example, the extruded item may be coated with a coating.

Extrusion Nozzle

Suitably, the extrusion apparatus comprises at least one extrusion nozzle through and from which an extrudable composition (or part thereof) can be extruded. Suitably the or each extrusion nozzle may be a heated extrusion nozzle, suitably a heated extrusion nozzle with a variable temperature control (e.g. to allow the extrusion nozzle to be selectively heated at a desired temperature). As such, the extrusion apparatus may comprise an extrusion nozzle heating element, suitably for heating the extrusion nozzle to melt, soften, or otherwise liquidise the or part of the relevant composition. Suitably, the extrusion apparatus may comprise a plurality of the aforementioned extrusion nozzles, each of which may be assigned to one or more extrudable compositions. Suitably such an extrusion nozzle is a part of the extruder.

The temperature of the nozzle(s) are suitably computer-controlled.

Suitably, the extrusion apparatus comprises a conveyor for conveying the extrudable composition(s) to and/or through the at least one extrusion nozzle.

Suitably the conveyor feeds the extrudable composition (for example by gripping a filament) through itself towards and/or through the relevant extrusion nozzle. Suitably the conveyor is controlled to deliver the extrudable composition at a rate and/or at intervals suitable to provide the desired extruded item. The conveyor, or a part thereof (e.g. "a feeder") (preferably a part en route to the extrusion nozzle) may be heated, suitably via a heating element associated therewith, optionally a separate and/or separately controllable heating element from any heating elements associated with the extrusion nozzle. Where the extrusion apparatus comprises more than one nozzle, suitably the extrusion apparatus comprises more than one feeder, one associated with each extrusion nozzle.

The temperature of the extrusion nozzle(s) are suitably computer-controlled. Suitably, the nozzle(s) are configured to operate at temperatures between 60 and 350° C., between 80 and 300° C., 100 and 220° C., or 120 and 190° C.

Suitably, the operating temperature of an extrusion nozzle through which relevant extrudable composition(s) pass is high enough to enable extrusion but low enough to avoid unacceptable degradation of any components, for example active ingredient(s), at the relevant filament feed rate. Suitably, the operating temperature of an extrusion nozzle through which relevant extrudable composition(s) pass is between 50 and 220° C., between 60 and 150° C., or between 70 and 120° C. However, the operating temperature of an extrusion nozzle may be as lower, for example less than 50° C., especially in systems that use extrudable compositions with low glass transition temperatures. Most suitably, the extrusion nozzle temperature is set to at least 65° C., more suitably at least 70° C. In a particular embodiment, the nozzle temperature is 50 to 130° C., 60 to 120° C., 70 to 110° C., or 80 to 100° C.

Suitably each extrusion nozzle comprises an input opening (into which the extrudable composition is fed) and an output opening (out of which the molten extrudable composition is deposited). The output opening is suitably smaller than the input opening. The input opening is suitably dimensioned to receive the extrudable composition (e.g. an extrudable element, blend, an extrudable fluid or an extrudable compressed form) therethrough. Suitably the input opening has a diameter of 0.1 to 100 mm, 0.2 to 10 mm, 0.3 to 5 mm, 0.3 to 3 mm, 0.3 to 2 mm, 0.4 to 1.5 mm, 1.5 to 2.0 mm, 1.5 to 2.0 mm, 0.75 to 1.25 mm, about 1 mm, 0.2 to 0.6 mm, about 1.75 mm, or about 0.4 mm. The output opening is suitably dimensioned for the properties of the corresponding extruded item to allow molten extrudable composition to be deposited therefrom (e.g. onto a build platform). Suitably the output opening has a diameter of 0.01 to 10 mm, 0.05 to 5 mm, 0.1 to 1 mm, 0.1 to 0.8 mm, 0.2 to 0.6 mm, or about 0.4 mm. In an embodiment, the nozzle has an output opening with a diameter of 0.3 to 0.5 mm.

Suitably the or each nozzle may be movable (suitably in an automated fashion or in a manner controlled by a computer or by the extruder under instruction from the computer) to extrude the extrudable composition at different locations upon the build platform (or upon the partially formed extruded item extruded thereon). The nozzle may be moveable in any or all of the X, Y, and Z direction, though in some embodiments (e.g. where the build platform is movable in the Z direction, i.e. up and down relative to the nozzle) it is constrained to move in only X and Y directions.

Suitably the or each extrusion nozzle is operable to move at a speed of between 1 and 150 mm/s whilst extruding (i.e. when the nozzle is "on"—this may be the nozzle extrusion speed), suitably between 70 and 110 mm/s, more suitably between 80 and 100 mm/s, suitably between 1 and 10 mm/s, suitably about 4 mm/s. Suitably the or each extrusion nozzle is operable to move at a speed of between 100 and 200 mm/s when not extruding (i.e. when the nozzle is "off"—this may be the nozzle travelling speed), more suitably between 120 and 180 mm/s, more suitably between 140 and 160 mm/s.

Suitably the speed of extrusion is constant while extruding (i.e., constant material flow).

It will be understood by those skilled in the art that the, each, or any nozzle may be adapted to suit the properties of the extrudable composition (e.g. a filament) configured to extrude thereto. The nozzle properties/design and extrudable composition properties suitably complement one another so as to facilitate controlled extrusion of said composition (be it continuous or intermittent, e.g. where more than one extrudable composition is used in the extruding an extruded item), suitably without any nozzle blockages or impedance, and suitably without any unacceptable degradation of ingredients within the extrudable composition during the extruding process.

Build Platform

The extrusion apparatus suitably comprises a build platform (or built plate) upon which the extrudable composition is extrudable (i.e. upon which the extruded item may be built). The build platform suitably provides a (substantially flat) surface that supports forming and formed extruded item throughout the extruding process. In a particular embodiment, the build platform comprises a surface, tape layer (i.e. a layer of tape at the surface) or surface coating which promotes adhesion of the extruded item to the build platform during the extruding process (i.e. promoting adhesion of a first layer of the extruded item to be extruded upon the build plate, suitably after the first layer hardens upon cooling), though suitably the extruded item is (readily) removable from the build platform following its production.

Suitably, during extruding (e.g. at the relevant extruding operating temperature), the surface of the build platform adheres to the extruded item (or at least to the layer thereof in contact with the build platform) sufficiently to prevent movement of the developing item during extrusion. Suitably, however, after extrusion (e.g. optionally at a different temperature to the extruding operating temperature) the extruded item(s) may be removed from the build platform without being damaged (e.g. the build platform is non-adherent enough to allow the extruded item(s) to be removed or is selectively tunable, e.g. by changing the operating temperature, to allow the extruded item(s) to be removed therefrom). As such, the surface of the build platform may comprise a surface coating or surface tape which imparts the required surface properties (e.g. adhesive but not too adhesive that the extruded items are permanently adhered).

The build platform is suitably configured or operable to maintain a surface temperature (i.e. for the surface in contact with the extruded item) during extruding of less than or equal to 150° C., 100° C., 90° C., 80° C., 70° C., 60° C., 50° C., 40° C., or 30° C. Suitably the surface temperature is greater than or equal to 5° C., 15° C., 30° C., or 40° C. This may be achieved through selective operation of heating and/or cooling elements associated with (e.g. lying beneath) the surface of the build platform. In a particular embodiment, the build platform is operable and preferably operated to maintain a surface temperature of between 5 and 150° C., between 20 and 110° C., between 20 and 100° C., about 90° C., or about 40° C. Advantageously the build platform is suitably configured or operable to maintain a surface temperature which facilities the removal or partial removal of the temporary plasticiser. Suitably the surface temperature is about the boiling point of the temporary plasticiser, for example about 80° C. or about 100° C. Suitably the surface temperature is less than the extrusion temperature. Suitably the surface temperature is less than or equal to the boiling point of the temporary plasticiser.

The build platform may be movable (suitably in an automated fashion or in a manner controlled by a computer or by the extruder under instruction from the computer) to control the position or height of extrusion upon the build platform. The build platform may be moveable in any or all of the X, Y, and Z direction, though in some embodiments the build platform is movable in the Z direction only, i.e. up and down. Movement in the Z direction allows the gap (or height) between the nozzle and the extruding point to be kept substantially constant throughout the extruding process to maintain layer-by-layer consistency.

Dispensers

The extrusion apparatus suitably comprises a dispenser. Suitably the dispenser comprises a storage container, such a hopper. The storage container suitably comprises the extrudable composition or precursor thereof. Suitably the storage container comprises an extrudable element. Suitably the storage container comprises an extrudable fluid. Suitably the storage container comprises an extrudable compressed form. The storage container is suitably sealed. The storage container may be in the form of a container (as defined herein, for example a cartridge or a syringe) specially adapted for compatibility with the apparatus of the invention. The storage container suitably has either an outlet (such as a valve-operated tap, optionally in conjunction with a positive dispensing means, such as a pressurizer or agitator) through and from which its contents may be dispensed, or a sampling port from which contents may be extracted by an external sampling element.

The dispenser suitably comprises one or more dispensing vessels. Suitably such dispensing vessels are configured to receive a quantity of the extrudable composition (or precursor thereof) from the storage container, suitably either directly or via a conveying means. Suitably the one or more dispensing vessels may receive a pre-determined dose of extrudable composition (or precursor thereof).

The dispenser suitably comprises a quantifying component, for example, a gravimetric or volumetric component.

Such a quantifying component suitably weighs or otherwise quantifies each dose of extrudable composition (or precursor thereof) to be dispensed. Suitably the dispenser is operable to convey a quantity of the extrudable composition (or precursor thereof) from the storage container to the quantifying component or to a dispensing vessel that interacts with the quantifying component. Suitably, one or more dispensing vessels are located so that quantifying component(s) can quantify the amount of the extrudable composition received by the dispensing vessel(s). Alternatively, the quantifying component may be associated with the storage container and thereby measure a mass reduction as the extrudable composition (or precursor thereof) is dispensed therefrom. Quantification may be performed by weight and/or by volume.

The dispenser suitably comprises a flow-control component, which suitably controls and meters the distribution of the extrudable composition (or precursor thereof) from the storage container to the one or more dispensing vessels. A flow-control component may, for example, comprise a controlled feed mechanism, and may suitably comprise an Archimedes screw, a valve, an agitator (e.g. to vibrate, tap, or shake). Alternatively or additionally, the flow-control component may comprise a sampling probe operable to sample a (estimated) quantity of the extrudable composition (or precursor thereof) from the storage container.

The dispenser suitably comprises an expelling mechanism for expelling quantified amounts of extrudable composition (or precursor thereof) from either a sampling probe or dispensing vessel. Such an expelling mechanism may suitably comprise a release means (e.g. a tap, valve, vacuum release, or other such mechanism, for example, which may tip the contents out of a dispensing vessel towards a target dispensing point). Alternatively or additionally the expelling mechanism may comprise an expulsion means, for example, a pressurizer, agitator, screw, piston or plunger, which forces the extrudable composition (or precursor thereof) from the dispensing vessel(s) to thereby dispense the extrudable composition.

In one embodiment, the dispenser comprises a hopper and a moveable metering element (e.g. a shuttle plate) which is movable relative to the hopper and comprises a metered cavity/container of a fixed or adjustable size. The size of the metered cavity determines the size of each dose. The moveable metering element may be operable to receive a quantity of the extrudable composition from the hopper before encapsulating a metered quantity thereof within the cavity, moving to a dispensing point, and dispensing the extrudable composition from the metered cavity.

The skilled person will be aware of certain challenges faced in the metered dispensing of materials, especially solids such as particulate solids. Forces acting in favour of outflow (e.g. gravity, pressure, and/or screw forces such as those of an Archimedes screw) are often counterbalanced by forces acting against the flow—for example: interparticle adhesion, adhesion to parts of the dispenser (e.g. walls of dispenser and/or dispensing outlet), abrasion, friction, erratic flow (e.g. creating rathole or arch profiles during funneling), compressibility (non-compressible solids flow better), outlet restriction (e.g. the bore of the outlet), angle of repose during funneling (angles less than or equal to 35° are preferred), external pressure (an external vacuum can assist) etc. Outflow of particles is particularly influenced by the particles themselves, in terms of particle shape, particle size, particle density, chemical nature of particles, surface roughness, and moisture content. Particle flow can be improved through judicious particle engineering, including techniques such as particle enlargement (e.g. granulation), cohesion reduction, smoothing/rounding, optimisation of moisture content, co-milling (e.g. to form flow-enhancing nanocoatings), and such like. A compressibility index of between 0-25%, suitably less than or equal to 25%, preferably less than or equal to 15%, preferably 10%, is reassuring for better particle flow. Moreover, particle sizes between 10 and 200 µm, suitably greater than or equal to 10 µm, 50 µm, or 100 µm are often preferable for optimal particle flow. As such, small particle sizes, including nanoparticles (e.g. less than or equal to 100 nm), may be better dispensed in the form of suspensions, such as nanosuspensions.

Suitably the components of the dispenser are computer-controlled, and suitably any valves or pressurizers are electronically controlled.

Suitably, a clench valve may be incorporated within a dispenser to control dispensation flow of particulates, such as granules.

Suitably the dispenser may further comprise a mixer. Suitably the mixer is a shear mixing. Suitably the mixer is configurable to operate at mixing rate of greater than or equal to 10 rpm, 25 rpm, 50 rpm, 75 rpm, 100 rpm, 125 rpm, 150 rpm, 175 rpm, 200 rpm, 250 rpm, 300 rpm, 400 rpm, or 500 rpm. Suitably the mixing rate is less than or equal to 500 rpm, 400 rpm, 300 rpm, 200 rpm, or 100 rpm. Suitably the mixer is configurable to operate at mixing rate of 10 to 500 rpm.

Computer Interface and Computer

The extrusion apparatus, including the extruder (and optionally the build platform), is suitably operable via the computer, suitably a computer running pursuant to specialist extrusion software, and optionally also to one or more databases, to extrude the extrudable composition and thereby forming the extruded item upon the build platform, suitably via a process involving the extrusion of an extrudable composition.

It will be readily understood by those skilled in the art that any one or more of the build platform, extrudable compositions, and/or computer, and/or any part thereof, may suitably be integrated within or form a part of the extruder. In an embodiment, the extrusion apparatus is essentially an extruder, 3D printer (including FFF 3D-printing) or printing apparatus.

Suitably, the extrusion apparatus comprises a computer interface (whether for wired or wireless connection to a computer operable to control the extruder).

The extrusion apparatus suitably comprises a computer for controlling the extruder. The computer may optionally control the build platform (e.g. its position, height, etc.). The computer may thus be configured to operate the extruder (e.g. 3D-printer) pursuant to a pre-determined extruded item design pattern.

The extruder suitably includes or is otherwise connected to a computer. The extruder is suitably connected to the computer via an interface (suitably a digital interface), which may be wired (e.g. a port-to-port connection via an appropriate data lead, e.g. a USB lead) or wireless. The computer may be located at the site of the extruder (i.e. a local computer). However, the invention is equally applicable where the relevant computer (or computers) is located remote from the site of the relevant extruder, but both the extruder and remote computer comprise or are otherwise connected to respective communicators allowing the remote computer and extruder to communicate with one another. In this manner, a remote computer may be caused to operate the extruder. In a particular embodiment, the extruder may be connected to a network so that multiple remote computers (and/or local computers) may communicate therewith to cause the operation of the extruder.

The computer associated or otherwise connected with the extruder suitably controls extrusion of the relevant extrudable composition(s) in accordance with an extruded item design and/or extruded item parameters (e.g. relative amounts and juxtaposition of ingredients) set forth in a given extruded item data file (e.g. in a CAD or a .STL file), suitably as interpreted by relevant software pursuant to which the computer runs.

In a particular embodiment, the extrusion apparatus comprises or is connected to a local computer, and both the extrusion apparatus and the local computer are located on site at a pharmacy, most suitably in a purpose-build extrusion area or room (which may be suitably have regulatory approval).

Suitably the method and/or extrusion apparatus involves a computer running pursuant to extrusion software (and optionally one or more internal and/or external databases).

Suitably, a computer running pursuant to said to extrusion software is configured to obtain information regarding one or more parameters (optionally including physical design parameters, such as shape) pertaining to the extruded item to be extruded (e.g. be it from information inputted manually by a user or information obtained automatically from another data source). Suitably the computer pursuant to said to extrusion software is configured to request manual user input via a user interface (e.g. keyboard/screen) regarding one or more parameters pertaining to the extruded item to be extruded. For example, a user (which may be a pharmacist acting under instruction from a patient and/or doctor) may be requested to input information regarding patient name, patient reference number (e.g. healthcare number), and/or another reference name or number, following which the computer may communicate (via relevant communicators associated therewith) with one or more databases (be it local or remote, wired or wirelessly, e.g. via a network such as the internet) to automatically call further information and/or options corresponding with said name or reference (e.g. personal patient data, medication history, repeat prescriptions, data or partial data relating to the extruded item to be extruded, including extruded item data files containing designs and/or other relevant parameters). Thereafter, the user may be requested to manually input or manually select further information (e.g. drug, drug dose, release profile, etc.) and/or options to allow the computer to obtain all relevant information pertaining to the printing of the extruded item form. Alternatively or additionally, the user may be requested to manually input or call information relating to one or more specific parameters pertaining to the extruded item (e.g. drug name/reference, drug dose, drug release requirements, colour, size, shape, solubility, packaging labelling information, etc.). Suitably, any user input may be logged and/or stored for future reference or for repeat prescriptions, etc.

There are a variety of ways the computer may be configured to obtain the relevant information to allow an extruded item to be extruded, but it is likely that a variety of pre-set information may be used (e.g. certain approved formulations/filament combinations for producing a given extruded item). As such, the computer may suitably be associated with or connected/connectable with an extruded item database (suitably a central database accessible via a network, such as the internet) which provides all necessary pre-set information (e.g. data files relating to the extruded item and details of variable parameters such as drug dose levels/limits).

Suitably, an extruded item design for extrusion (and optionally parameters connected therewith) may be recorded in an extruded item data file, which may be read by a computer running pursuant to the extrusion software.

Suitably, a computer running pursuant to said to extrusion software is configured to calculate the mass and/or volume of the extruded item to be extruded based on the information obtained. Suitably once the computer has obtained all required information (be it information manually inputted by a user, information imported automatically, or a combination of both) it is configured to perform calculations to allow finalisation of extruding instructions before the computer controls extrusion. At this stage, further input may be required or requested (e.g. via a user interface), for instance dimension(s) and/or shape modifications may be optionally selected. Calculations typically relate to the mass and/or volume of a given extruded item required to provide a given active dosage per extruded item (e.g. in the case of extruded item). Though it may be possible to increase the concentration of a given active ingredient relative to other ingredients (e.g. excipients), typically formulations are optimised and relative proportions fixed/pre-set, whereas overall mass/volume may be varied whilst retaining the same relative proportions of ingredients.

Suitably, a computer running pursuant to said extrusion software is configured to control extrusion of and relative proportions of ingredients within the extruded item, suitably based on the information obtained and suitably based on the calculations performed. Suitably "controlling extrusion" includes initiating extrusion and terminating extrusion and any or all extrusion operations therebetween.

Suitably during extrusion, operational data is collected (optionally by one or more local and/or remote computers and/or databases) and suitably stored (most suitably at a central computer which may analyse such data, e.g. for quality control monitoring, monitoring of malfunctions, monitoring of batches, monitoring of dosage forms dispensed to a given patient, etc.). Suitably the extrusion apparatus comprises or is otherwise associated with one or more operational sensors (e.g. nozzle temperature sensors, extrudable composition feed rate sensors or conveyor sensors, overall temperature sensors, build platform sensors which may, for example, monitor surface temperature and/or rate of post-extrusion cooling, etc.) which feedback operational parameters/information to a computer, database, or data storage facility, relating to the operation of the extrusion apparatus and elements associated therewith during the extrusion of each extruded item. Most preferably, such operational data is collected, stored, and/or otherwise transmitted to a central computer or database to enable independent auditing of any given extrusion apparatus. This may be important in order to maintain quality control, and maintain appropriate records in order to retain regulatory approval of any given extrusion system.

Suitably, a computer running pursuant to said to extrusion software is configured to control performance of one or more further processing steps.

Software and Data Files

The computer operating the extrusion apparatus suitably runs pursuant to extrusion software (and optionally also to one or more databases). As explained herein, this software may configure the computer to obtain information and perform calculations before it then configures the computer to control extruding via an interface with the extrusion apparatus.

Once the computer has obtained the relevant information and performed the relevant calculation, suitably the software configures the computer to control extrusion of the extrudable composition thereby forming the extruded item, suitably based on a design (shape and dimensions, texture, layer structure, internal structure, porosity, colour(s), etc.) and/or parameters (relative amounts of ingredients, such as drug dose) relating to said extruded item contained within one or more extruded item data files. The extruded item data files may include a design file (e.g. containing data and/or images relating to the physical design of the extruded item, including its dimensions, shape, layered structure, core-shell structure, etc.) and/or a parameter file (e.g. containing data relating to the chemical composition of the extruded item, including drug type, excipient type(s), drug dose level, excipients to control drug release, etc.). A single extruded item data file may contain all data pertaining to the physical design and chemical composition. However, the physical design and chemical composition may be modified pursuant to information obtained following user input.

In some embodiments, the design file may be a CAD file depicting an extruded item. However, such file formats are likely to require conversion to a file format compatible with the extrusion apparatus. In particular, 3D printers generally read design files in a .STL format. As such, the design file is suitably a .STL design file depicting the extruded item (or at least the physical design thereof).

The design file may include or be linked with a parameter file containing chemical composition details, or the two may be independent. Alternatively there may be no parameter file as such and instead the relevant parameter information may be called from a database, for instance, in response to user input (e.g. patient reference, or drug reference, etc.).

The software may additionally configure the computer to collect, store, and/or transmit (e.g. to a central database) operational data fed back to the computer from the extrusion apparatus (e.g. 3D printer) during extrusion. The software may configure the computer to detect and/or respond to any (or a preset level of) deviation in expected operational data (e.g. if nozzle temperatures exceed a maximum preset temperature level), for instance alerting the user/operator or any other interested party that a malfunction has occurred and that the extruded item produced during malfunctional extrusion should be disposed or otherwise tested.

Databases

The extrusion apparatus and/or computer(s) associated therewith may be configured (e.g. by the extrusion software) to communicate with (suitably via relevant communicator(s), and suitably via a network such as the internet) one or more extruded item databases and/or patient databases to obtain information regarding one or more parameters pertaining to the extruded item to be prepared. For example, such database(s) may be consulted in response to a user input (e.g. patient reference number) to furnish the computer with the relevant information (or relevant information to be supplemented by further user input) to enable calculations and extrusion to be performed.

By way of example, a patient database comprising patient records for multiple patients (which records may include, for example, patient name, patient reference number, medical data, medical history, etc.) suitably contains information (which may merely be a cross-reference or reference number relating to information residing in another database, such as an extruded item database) regarding the extruded item to be extruded for each patient. Where the "information" is a cross-reference to an extruded item database, this extruded item database may then be consulted for further information regarding the extruded item. This information may be any of the information defined herein, though optionally the extrusion apparatus or computer(s) associate therewith may be instructed (e.g. via a user interface) to modify the information (e.g. drug dose level) prior to calculations and/or extrusion. Any of these databases may be accessible to interested parties, preferably securely accessible (to maintain confidentiality of certain data), to enable the relevant information (be it in a patient database, extruded item database, or both) to be retrieved and/or amended as required (e.g. if a patient needs an increased dose in the extruded items or a different active release profile). Suitably such database(s) may be wirelessly accessible via a network, such as the internet. Such database architectures are well known in the art.

The or each extrusion apparatus and/or computer(s) associated therewith may be configured (e.g. by the extrusion software) to communicate with (suitably via relevant communicator(s), and suitably via a network such as the internet) one or more extrusion apparatus-monitoring databases configured to transmit to and store within said database (and optionally analyse and/or report upon) operational data collected (optionally by one or more local and/or remote computers and/or databases) during each extrusion operation (i.e. each time an extrusion apparatus extrudes). As described herein, such operational data is suitably obtained/delivered by sensors associated with each given extrusion apparatus, suitably sensors associated with key parts of the extrusion apparatus that could affect the quality of the ultimate extruded item. The operational data may be transmitted to said database in real time, following extrusion, or at any suitable time (e.g. at night to avoid unnecessary overloading communication networks during work hours). Such extrusion apparatus-monitoring databases may be organised with a record for each extrusion apparatus, and may suitably maintain a log of operational data each time said extrusion apparatus is operated. Suitably each set of operational data is cross-reference to a given patient an extruded item, suitably so that if any operational data is deemed malfunctional, the relevant interested parties can be alerted. In this manner, each extrusion apparatus may be monitored (whether in real time or otherwise, whether automatically or otherwise) and data periodically submitted to satisfy regulatory requirements. Moreover, central extrusion apparatus-monitoring databases may trigger a response to any perceived malfunction of a given extrusion apparatus. Moreover, a response may be triggered which prevents the relevant malfunctional extrusion apparatus from being used until its performance can be revalidated.

Again, any of the one or more extrusion apparatus-monitoring databases may be accessible to interested parties, preferably securely accessible (to maintain confidentiality of certain data), to enable the relevant information to be retrieved and/or analysed as required (e.g. if regulatory bodies wish to check that a given extrusion apparatus has been in good order throughout a given period, or if machine maintenance professionals which to use the data to diagnose a problem in order to restore the performance of a given extrusion apparatus). Suitably such database(s) may be wirelessly accessible via a network, such as the internet. Such database architectures are well known in the art.

Extrudable Composition

The present invention provides an extrudable composition. The extrudable composition may be an extrudable composition obtainable by, obtained by, or directly obtained by the method for preparing an extrudable composition as defined herein.

The present invention provides an extrudable composition comprising:
i. An extrudable carrier; and optionally
ii. A temporary plasticiser.

The present invention provides an extrudable composition comprising:
i. An extrudable carrier; and
ii. A temporary plasticiser.

Suitably the extrudable composition is a blend of the temporary plasticiser and the extrudable carrier, the active ingredient if present, the permanent plasticiser if present, and the other components if present.

Suitably, the majority of the extrudable composition is in the molten state at the extrusion temperature. The molten state means that the extrudable composition can be extruded at the extrusion temperature; it does not necessary mean all components of the extrudable composition have to be in the molten state. For example, the mixture of the extrudable carrier and the temporary plasticiser are in the molten state at the extrusion temperature.

In one embodiment, the extrudable composition is a free-flowing blend. Advantageously, the free-flowing blend is preparing by blending the components of the extrudable composition by mixing, such as shear mixing.

In one embodiment, the extrudable composition is an extrudable compressed form (or a plurality of extrudable compressed forms), such as a tablet(s), for example a mini-tablet(s). Advantageously, compressing the extrudable composition allows the extrudable compressed form to be prepared in advance of the process to prepare the extruded item. For example, the extrudable compressed form can be prepared in advance at the same or different location to the site of the extruder, and/or stored for a period of time until it is required. Additionally, by having the extrudable composition in a compressed form physical separation of the various components of the extrudable composition over time may be prevented thereby potentially reducing any variability during the extrusion process. Also, using extrudable compressed forms, such as mini-tablets, in the extrusion process advantageously means that the process can be run continuously (i.e., by providing a continuous feed of the extrudable compressed form into the extruder) thereby allowing the process to be run more time and cost efficiently.

Suitably each extrudable compressed form has a weight of 10 to 1000 mg, 20 to 800 mg, 20 to 500 mg, 40 to 300 mg, 50 to 250 mg, 100 to 200 mg, 20 to 80 mg, 30 to 70 mg, 40 to 60 mg, or about 50 mg.

Suitably each extrudable compressed form has a diameter of 1 to 10 mm, 2 to 8 mm, 4 to 7 mm, 5 to 7 mm, or about 6 mm.

In one embodiment, the extrudable composition is an extrudable fluid, suitably an extrudable semi-fluid, for example, a molten composition. Suitably the extrudable fluid is a fluid at room temperature. Suitably the extrudable fluid is a fluid at ambient temperature, or is a fluid at a temperature greater than or equal to 30° C., 40° C., 50° C., 60° C., 70° C., 80° C., or 90° C. Suitably the extrudable composition can be extruded at a temperature of less than or equal to 200° C., 180° C., 150° C., 120° C. or 100° C. Suitably the extrudable composition can be extruded at a temperature of 30 to 200° C., suitably 30 to 150° C. It is to be understood that a fluid means that the extrudable composition can be extruded (i.e., a suitably viscosity to be extruded) at said temperature.

In one embodiment, the extrudable composition is an extrudable element. Suitably, the extrudable element is a filament. Advantageously the extrudable composition can be extruded for a first time (forming an extrudable element, such as a filament) prior to being extruded a second time during the process to prepare the extruded item. In particular, the use of filaments in 3D-printing technologies is well established, for example in fused filament fabrication (FFF) technologies. The temporary plasticiser allows the extrusion temperature in the process to form the extrudable element (e.g. the filament) to be lower than if no temporary plasticiser was present therefore making the process well suited for use with components of the extrudable composition which are thermally sensitive. Subsequent partial or full removal of the temporary plasticiser from the extrudable element can yield an extrudable composition with physical properties suited for the use in the process to prepare the extruded item. For example, the temporary plasticiser can initially be used to reduce the extrusion temperature used in forming the extrudable element by reducing the glass transition (softening) temperature of the extrudable composition used to prepare the extrudable element. Due to the lower glass transition (softening) temperature the physical properties may not be optimal for subsequent processing, for example, the resulting extrudable element may be too flexible for use in FFF 3D-printing. Partial removal of the temporary plasticiser results in the glass transition (softening) temperature of the extrudable element being increased and in doing so the extrudable composition becomes less flexible. The amount of temporary plasticiser which is removed (and thereby increasing the glass transition (softening) temperature) can be optimised to that the extrudable element has the optimal physical properties (e.g. flexibility) to be used in the process to from the extruded item.

It will be appreciated by the skilled person that the extrudable element can also be an extruded item. As such features which are applicable to the extruded item may be applicable to the extrudable element.

The process to form the extrudable element exposes the components of the extrudable element to elevated temperatures for longer than the process to form the extruded item from the extrudable element. This is due to the residence time in the extruder being longer when extruding bulk materials compared to when extruding (e.g. 3D-printing) extrudable elements (e.g. filaments). Advantageously, the levels of the temporary plasticiser result in the extrusion temperature being lower for preparing an extrudable element and/or extruded item. Advantageously, it is possible to have the first extrusion temperature (i.e., temperature used to prepare the extrudable element) being lower (i.e., when the temporary plasticiser content is at its highest) than the temperature to prepare the extruded item from the extrudable element (i.e., wherein the temporary plasticiser has been removed or partially removed from the extrudable element either during the production of the extrudable element or during the optimisation of the physical properties of said item, such as flexibility/brittleness, for use in extruding, i.e., 3D-printing, the extruded item). Thus, the extent of thermal degradation can be minimised in by reducing the extrusion temperature used in forming the extrudable element, and having a shorter residence time and/or reducing the extrusion temperature used in forming the extruded item.

Suitably the extrudable element is substantially free of the temporary plasticiser. Suitably the filament is substantially free of the temporary plasticiser. Suitably the extrudable element is entirely of the temporary plasticiser. Suitably the filament is entirely free of the temporary plasticiser.

Suitably the filament has a thickness (i.e. diameter or maximum thickness) of between 0.1 mm and 5 mm, between 0.5 mm and 2 mm, between 0.5 mm and 1.5 mm, or between 0.8 mm and 1.2 mm. In a particular embodiment, the filament has a thickness of about 1 mm. However, the filament thickness may be adjusted to suit the extrusion nozzles (in particular the size/diameter of the respective openings thereof) through which they are to be extruded.

Suitably, the filament is capable of being coiled (or spooled) around a spool, suitably a spool having a hub diameter of about 25 cm, about 20 cm, about 15 cm, about 12 cm, about 10 cm, about 8 cm, about 6 cm, about 5 cm, about 4 cm, about 2.5 cm, or about 1 cm, Suitably the hub diameter allows the filament to coiled (or spooled) around a spool without breaking and/or stretching.

The extrudable composition suitably has less than or equal to 30% weight, 25% weight, 20% weight, 18% weight, 16% weight, 14% weight, 12% weight, 10% weight, 8% weight, 6% weight, 5% weight, 4% weight, 3% weight, 2% weight, or 1% weight of the temporary plasticiser. Suitably the extrudable composition comprises greater than or equal to 5%, 10%, 15%, or 20% of the temporary plasticiser. Suitably the extrudable composition comprises 1 to 25% of the temporary plasticiser.

The extrudable composition suitably has a glass transition (softening) temperature ($T_g$) between −50° C. and 100° C., −40° C. and 80° C., −40° C. and 75° C., −40° C. and 60° C., −40° C. and 50° C., −40° C. and 30° C., −20° C. and 50° C., −35° C. and 25° C., −30° C. and 25° C., −25° C. and 25° C., −20° C. and 25° C., −20° C. and 20° C., −20° C. and 15° C., −20° C. and 10° C., −20° C. and 5° C., −20° C. and 0° C., −20° C. and −5° C., −15° C. and −5° C., −15° C. and −10° C., or −12° C. and −8° C. Suitable the extrudable composition has a glass transition temperature of about −15° C. or about −10° C. Suitably the extrudable composition has a glass transition (softening) temperature ($T_g$) of less than or equal to 70° C., 60° C., 50° C., 40° C., 30° C., 20° C., 10° C., 5° C., 0° C., −5° C., −10° C., −15° C., or −20° C.

Suitably, the extrudable composition is judiciously tailored with appropriate proportions and types of ingredients wherein the extrusion temperature used to prepare the extruded item is minimised.

Suitably the extrudable carrier, the temporary plasticiser, and if present, the permanent plasticiser, form part of, or all of, a meltable component of the extrudable composition. The extrudable composition may further comprise a non-meltable component to mitigate nozzle blockages. Suitably, the "meltable" component is a component that melts (or undergoes a glass transition to thereby soften) at the designated operating temperature of any extrusion apparatus nozzle (e.g. 3D printer) configured to process said extrudable composition, whereas the "non-meltable" component is suitably a component that does not melt (or undergo a glass transition) at the same temperature. Suitably, the "meltable" component is a mixture of components, which collectively melt or undergo glass transitions together as a mixture—e.g. extrudable carrier and temporary plasticiser. However, "non-meltable" components are more likely to be individual components with different melting points or glass transition temperatures. Suitably the meltable component has a melting point (or $T_g$) at or below 220° C., 150° C., 100° C., 80° C., or 60° C. Suitably the meltable component has a melting point (or $T_g$—i.e. at least one $T_g$) greater than or equal to 20° C., suitably greater than or equal to 30° C. Suitably the meltable component has a melting point (or $T_g$—i.e. at least one $T_g$) between 20 and 220° C., between 30 and 200° C., between 30 and 150° C., between 30 and 65° C., or between 30 and 35° C. Suitably, the non-meltable component has a melting point (or $T_g$) at or above 150° C., 200° C., 500° C., or 1000° C.

The meltable component suitably has a glass transition temperature lower than the melting point of the active ingredient, suitably at least 20° C. lower, at least 40° C. lower, or at least 50° C. lower.

As explained above, references to "meltable" and "non-meltable" components encompasses "softenable" and "non-softenable" components respectively, where instead of "melting" at a particular temperature the component "softens" thereby allowing extrusion at said temperature. As such, references in this context to a melting point may additionally or alternatively relate to a glass transition temperature. Such glass transitions are particularly applicable to thermoplastic component(s). As such, a "meltable" component may be a thermoplastic component, suitably who glass transition temperature (temperature at which the thermoplastic component softens rather than melts) is lower than the temperature to which said component is exposed (e.g. during extrusion).

Each of the various ingredients described herein are suitably either a meltable or a non-meltable component (not both). For instance, the mixture of an extrudable carrier and a temporary plasticiser is suitably a meltable component and is suitably selected to undergo melting or a glass transition during extrusion. A filler (e.g. calcium tribasic phosphate, talc, etc.), by contrast, is suitably a non-meltable component and is suitably selected so as to remain solid during extrusion. Notwithstanding the contrasting melting/glass-transition properties of the various ingredients, suitably the extrudable composition (for example a filament) itself has a characteristic glass transition temperature. Suitably this characteristic glass transition temperature is measurable using the well-known techniques described herein and elsewhere and is a consequence of the combination of ingredients. Various concentration (wt %) ratios of meltable:non-meltable components may afford viable extrudable compositions for extruding, such as 3D printing. Suitably the ratio of meltable:non-meltable components is between 1:10 and 10:1, more suitably between 3:7 and 7:3, suitably between 4:6 and 6:4, where suitably the meltable component(s) collectively include all relevant meltable components (e.g. extrudable carriers, temporary plasticisers, permanent plasticisers etc.) and the non-meltable component(s) include all relevant non-meltable components (e.g. filler(s), lubricants, etc.).

The extrudable composition (e.g. an extrudable element) is suitably sufficiently stiff to enable it to be viably fed (at a consistent rate) to and through a corresponding extrusion nozzle within the extrusion apparatus. The extrudable composition is suitably sufficiently stiff to avoid the extrudable composition (e.g. an extrudable element) becoming stretched during printing. However, the extrudable composition (e.g. an extrudable element) is suitably not so stiff that the nozzle operating temperature required to extrude the filament will degrade the contents of the ingredient (e.g. causing a change in composition of greater than or equal to 1 wt %).

In one embodiment, the extrudable composition, for example an extrudable element such as a filament, is suitably sufficiently flexible and/or soft to enable it to be extruded (at a consistent rate) from a corresponding extrusion nozzle within the extrusion apparatus. In one embodiment, the extrudable element is suitably sufficiently flexible and/or soft to allow the extrudable composition, for example an extrudable element such as a filament, to be viably spooled/coiled around a filament spool.

In general, if an extrudable composition (i.e., an extrudable element such as a filament) has a glass transition temp (Tg) that is too high, it may be too brittle (for instance, to coil onto a filament spool) for an extruder to handle (i.e. without breaking the filament), and/or may require extrusion nozzle operating temperatures that are so high that degradation of the ingredients within the extrudable composition may occur during the process to prepare an extruded item. Conversely, where an extrudable composition has a glass transition temperature that is too low, the extrudable composition (i.e., a filament) may be too soft and/or flexible for an extruder to handle, too distortable for consistent extrusion, and yields poor shape control and incoherent extruded items during the process to prepare an extruded item. The extrudable composition (e.g. a filament) is suitably neither too brittle (and breakable during printing/spooling) nor too flexible (precluding its viable conveyance through the extrusion apparatus). The dimensions of the extrudable composition (e.g. thickness of the filament) can be judiciously altered, using the principles taught in the present disclosure, to obtain an optimal structure.

Suitably, the extrudable composition comprises at least one active ingredient, suitably a pharmaceutically, nutraceutically, or food supplement active ingredient as herein defined. Most suitably the at least one active ingredient is a pharmaceutically active ingredient.

Suitably the extrudable composition comprises a permanent plasticiser as herein defined.

Suitably the extrudable composition comprises one or more other component as herein defined.

Many of the features preferred of the extrudable composition are described elsewhere herein. For instance, features described in relation to the method of producing the extrudable composition may suitably reflect a feature of the extrudable composition itself (e.g. filament diameter).

Extruded Item

The present invention provides an extruded item. The extruded item may be an extruded item obtainable by, obtained by, or directly obtained by the method for preparing an extruded item as defined herein.

The extruded item is suitably formed from the extrudable composition and thus the extruded item suitably is or comprises the extrudable composition. As such, any definitions herein relating to the extrudable composition may be equally applicable to the extruded item per se.

The present invention provides an extruded item comprising an extrudable carrier and a temporary plasticiser.

Most suitably, the composition of the extruded item comprises a lower amount (including substantially free and entirely free) of the temporary plasticiser than the extrudable composition. In one embodiment, the extruded item comprises low levels of the temporary plasticiser, for example, less than or equal to 30% weight, 20% weight, 10% weight, 8% weight, 6% weight, 5% weight, 4% weight, 3% weight, 2% weight, 1% weight, 0.5% weight, 0.2% weight, or 0.1% weight. Suitably the extruded item is substantially free of the temporary plasticiser or entirely free of the temporary plasticiser. Suitably, the extruded item comprises 0 to 30% of the temporary plasticiser. Suitably the extruded item has 10%, 20%, 30%, 40%, 50%, 60%, 70%, 80%, 90%, 95%, or 98% less temporary plasticiser than the extrudable composition used to prepared said item.

The extruded item(s) of the present invention are generally discernible by chemical and/or microscopic analysis, which will suitably reveal whether or not the extruded item has been extruded, e.g. 3D-printed, for instance by extruding the extrudable composition in a layer-by-layer fashion. Suitably the extruded item comprises a plurality of layers. Suitably each layer has a thickness of between 10 and 1000 µm, 20 and 800 µm, 30 and 500 µm, 40 and 300 µm, 50 and 200 µm, 100 and 200 µm, 125 and 200 µm, 140 and 190 µm, 155 and 175 µm, 250 and 350 µm, or 750 and 850 µm. Suitably each layer has a thickness of about 166 µm, about 300 µm, or about 800 µm. Suitably each layer of the extruded item can have the same thickness or each layer can have a different thickness. Suitably there are no gaps between layers.

The extruded item(s) of the present invention are suitably for oral administration. Examples of such extruded items are tablets, capsules, granules, powders, beads and microcapsules. Most suitably, the extruded item is a tablet or implant, most suitably a pharmaceutical tablet or medical implant (e.g., an implant which allows for sustained and/or controlled release of an active ingredient).

The extruded item(s) of the present invention are advantageously customisable in terms of the type/nature of active ingredient, the dose of active ingredient within the extruded item (be it an absolute dose per extruded item or the concentration of the active ingredient with the extruded item), the mass/volume of the extruded item (which is typically adaptable to vary the absolute dose of the active ingredient without changing the concentration of the active ingredient within the extruded item), the active ingredient release profile (which may be varied by judicious use and/or distribution of appropriate excipients), or shape and appearance (including novelty shapes, colours, and patterns, such as those that may help medical compliance for particular patients).

Suitably the extruded item is a filament.

Suitably the extruded item is a pharmaceutical, nutraceutical, or food supplement solid dosage form, for example a tablet. Suitably the extruded item is a pharmaceutical solid dosage form, for example a tablet. Suitably the extruded item is an immediate release dosage form, a delayed release dosage form (e.g., with enteric coatings or shells), or a sustained release dosage form.

Suitably, the extruded item is a solid oral dosage form, most suitably, an immediate release solid dosage form.

The immediate release solid dosage form suitably releases at least 75% of the active ingredient(s) within a 45 minute period, suitably releases at least 85% of active ingredient(s) within a 30 minute period, and may suitably release at least 85% of the active ingredient(s) with a 15 minute period. The skilled person may refer to European Pharmacopeia 8.0. Strasbourg, France: Council of Europe; European Directorate for the Quality of Medicine; 2014 for further details.

The longest dimension ($D_{max}$) of the extruded item (e.g. whether in the X, Y, or Z direction) is suitably greater than or equal to 3 mm, 5 mm, 8 mm, 10 mm, or 12 mm. The longest dimension of the extruded item is suitably less than or equal to 30 mm, 25 mm, 20 mm, or 15 mm.

The shortest dimension ($D_{min}$) of the extruded item (i.e. not necessarily the thinnest part but the maximum length of the thinnest dimension, or the shortest of the X, Y, or Z) is suitably greater than or equal to 0.1 mm, 0.5 mm, 1 mm, 3 mm, 5 mm, 8 mm, 10 mm, or 12 mm. The shortest dimension of the extruded item is suitably less than or equal to 30 mm, 25 mm, 20 mm, 15 mm, 10 mm, 8 mm, 5 mm, or 2 mm. Suitably, the shortest dimension ($D_{min}$) of the extruded item is between 0.1 and 30 mm.

The volume of the extruded item is suitably greater than or equal to 3 mm$^3$, 5 mm$^3$, 10 mm$^3$, 50 mm$^3$, 100 mm$^3$, or 200 mm$^3$. The volume of the extruded item is suitably less than or equal to 500 mm$^3$, 300 mm$^3$, 250 mm$^3$, 150 mm$^3$, or 50 mm$^3$. Suitably, the volume of the extruded item is between 3 and 500 mm$^3$.

Suitably the extruded item has a weight of greater than or equal to 1 mg, suitably greater than or equal to 5 mg, 10 mg, 50 mg, or 80 mg. Suitably the extruded item has a weight of less than or equal to 1000 mg, suitably less than or equal to 500 mg, 250 mg, or 100 mg. Suitably the extruded item has a weight of between 1 and 1000 mg.

Suitably the extruded item is a pharmaceutical, nutraceutical, or food supplement solid dosage form. Suitably, the extruded item comprises at least one active ingredient, suitably a pharmaceutically, nutraceutically, or food supplement active ingredient as herein defined. Most suitably the at least one active ingredient is a pharmaceutically active ingredient.

Suitably the extruded item comprises a permanent plasticiser as herein defined.

Suitably the extruded item comprises one or more other component as herein defined.

Many of the features preferred of the extruded item are described elsewhere herein. For instance, features described in relation to the method of producing the extruded item may suitably reflect a feature of the extruded item itself (e.g. layer height). Suitably the extruded item comprises ingredients provided by the extrudable composition(s) used in its formation and may be considered to comprise relevant extrudable compositions.

Components in the Extrudable Composition and Extruded Item

The components described below apply to methods, apparatus, packaging and applications described herein.

Extrudable Carrier

The extrudable carrier is suitably an extrudable material suitable for use in extrusion, such as 3D-printing, and especially suitable as a printable (and suitably meltable/softenable) carrier ingredient within filaments for FFF 3D-printing. Suitably, any suitable polymer(s) may be used.

The extrudable carrier(s) is suitably selected from a polymer (suitably a cationic polymer or a neutral polymer or copolymer) having a viscosity of less than or equal to 300 mPa·s, 200 mPa·s, 100 mPa·s, 80 mPa·s, 65 mPa·s, 50 mPa·s, 30 mPa·s, or 10 mPa·s, though suitably having a viscosity of at least 1 mPa·s. Suitably, the polymer has a viscosity of 1 to 300 mPa·s.

The extrudable carrier(s) suitably has or comprises one or compounds having a molecular weight of at least 2,000 g/mol, 5,000 g/mol, 10,000 g/mol, 15,000 g/mol, 20,000 g/mol, 35,000 g/mol, 45,000 g/mol, or 100,000 g/mol. Suitably, the molecular weight is 2,000 to 500,000 g/mol, or 2,000 to 100,000 g/mol. Molecular weights are suitably cited in g/mol. Suitably molecular weights are average molecular weights, especially where they may refer to polymers.

The extrudable carrier(s) suitably is or comprises one or compounds that is sparingly soluble, slightly soluble, very slightly soluble, practically insoluble, or insoluble according to the standard USP definitions (and standard tests defined therefore in the USP) as per the table below:

| Descriptive Term | Parts of Solvent Required for 1 Part of Solute |
| --- | --- |
| Very soluble | Less than 1 |
| Freely soluble | From 1 to 10 |
| Soluble | From 10 to 30 |
| Sparingly soluble | From 30 to 100 |
| Slightly soluble | From 100 to 1,000 |
| Very slightly soluble | From 1,000 to 10,000 |
| Practically insoluble, or Insoluble | Greater than or equal to 10,000 |

The extrudable carrier(s) suitably is or comprises one or compounds that is very slightly soluble, practically insoluble, or insoluble according to the standard USP definitions as per the table above. Suitably, the extrudable carrier(s) suitably is or comprises one or compounds that is practically insoluble, or insoluble according to the standard USP definitions as per the table above.

The extrudable carrier itself suitably has a melting point between 140 and 250° C., suitably between 160 and 250° C., or between 170 and 230° C.

The melting point (or glass transition temperature) of the extrudable carrier is suitably less than the active ingredient, suitably by at least 20° C., 40° C., or 50° C. The extrudable carrier suitably has a melting point between 140 and 250° C., between 150 and 200° C., or between 155 and 175° C.

The extrudable carrier itself suitably has a glass transition temperature of greater than or equal to 0° C., 10° C., 20° C., 25° C., 40° C., 50° C., 60° C., 70° C., 80° C., 90° C., 100° C., 120° C., 140° C., 160° C., 180° C., or 200° C. The extrudable carrier itself suitably has a glass transition temperature of 0° C. to 250° C., suitably 0° C. to 200° C. In some embodiments, the extrudable carrier does not have a glass transition temperature as such, though observed softening may still occur.

The extrudable carrier suitably has a glass transition temperature lower than the melting point of the active ingredient, suitably at least 20° C. lower, at least 40° C. lower, or at least 50° C. lower.

Suitably the extrudable carrier has a specific heat of between 0.1 and 1 cal/g° C., most suitably between 0.3 and 0.5.

The extrudable carrier suitably has a density between 1.1 and 1.6 g/mL, most suitably between 1.2 and 1.4.

Any suitably extrudable carrier(s) may be used. In the context of pharmaceuticals, extrudable carriers are customarily used in the compounding of solid dosage forms such as tablets and capsules.

The extrudable carrier(s), especially where an immediate release solid dosage form is desired, is suitably selected from a carrier (suitably a cationic polymer or neutral polymer or copolymer) having a viscosity of no more than 50 mPa·s, suitably no more than 30 mPa·s, suitably no more than 10 mPa·s, though suitably having a viscosity of at least 1 mPa·s—suitably a viscosity between 1 and 50 mPa·s, suitably between 1 and 25 mPa·s, suitably between 2 and 8 mPa·s. The extrudable carrier(s), especially where an immediate release solid dosage form is desired, is suitably selected from a carrier having a molecular weight of at least 20,000 g/mol, suitably at least 35,000, suitably at least 45,000, though suitably less than 1,000,000 g/mol, suitably less than 100,000 g/mol—suitably a molecular weight between 20,000 and 1,000,000 g/mol, suitably between 35,000 and 65,000 g/mol. The extrudable carrier(s), especially where an immediate release solid dosage form is desired, is suitably selected from a carrier having a glass transition temperature (Tg) of at most 100° C., suitably at most 80° C., suitably at most 50° C., though suitably at least −10° C., suitably at least 35° C.—suitably a Tg between −10 and 100° C., suitably between 30 and 60° C. In some embodiments, the extrudable carrier(s) may not have a glass transition temperature as such, though observed softening may still occur. The extrudable carrier(s), especially where an immediate release solid dosage form is desired, is suitably an (optionally alkyl-, suitably methyl- or ethyl-) acrylate, methacrylate and/or ethacrylate copolymer (suitably comprising amine-containing monomeric units) suitably having a viscosity between 2 and 8 mPa., suitably having a molecular weight between 35,000 and 65,000 g/mol, and/or suitably having a Tg between 30 and 60° C. In a particular embodiment, the relevant copolymer is poly(butyl methacrylate-co-(2-demethylaminoeethyl) methacrylate-co-methyl methacrylate), suitably in a respective monomeric molar ratio of 1:2:1 (+/−5% for each molar value of the ratio). The extrudable carrier is suitably Eudragit E.

The extrudable carrier(s), especially where an extended release solid dosage form is desired, is suitably selected from a carrier having a viscosity of no more than 30 mPa·s, 20 mPa·s, or 16 mPa·s, though suitably having a viscosity of at least 1 mPa·s—suitably a viscosity between 1 and 30 mPa·s, suitably between 1 and 15 mPa·s. The extrudable carrier(s), especially where an extended release solid dosage form is desired, is suitably selected from a carrier having a molecular weight of at least 10,000 g/mol, 250000 g/mol, or 30,000 g/mol, though suitably less than 100,000 g/mol, suitably less than 40,000 g/mol—suitably a molecular weight between 10,000 and 100,000 g/mol, suitably between 29,000 and 35,000 g/mol. The extrudable carrier(s), especially where an extended release solid dosage form is desired, is suitably selected from a carrier having a glass transition temperature (Tg) of at most 100° C., suitably at most 80° C., suitably at most 70° C., though suitably at least 40° C., more suitably at least 50° C.—suitably a Tg between 50 and 100° C., suitably between 55 and 70° C. In some embodiments, the extrudable carrier(s) may not have a glass transition temperature as such, though observed softening may still occur. The extrudable carrier(s), especially where an extended release solid dosage form is desired, is suitably an (optionally alkyl-, suitably methyl- or ethyl-) acrylate, methacrylate and/or ethacrylate copolymer (suitably comprising amine-containing monomeric units) suitably having a viscosity between 1 and 15 mPa., suitably having a molecular weight between between 29,000 and 35,000 g/mol, and/or suitably having a Tg between 55 and 70° C. In a particular embodiment, the relevant copolymer is poly(ethyl acrylate-co-methyl methacrylate-co-trimethylammonioethyl methacrylate chloride), suitably in a respective monomeric molar ratio of 1:2:0.2 (+/−5% for each molar value of the ratio). The extrudable carrier is suitably Eudragit RL.

The extrudable carrier(s), especially where a delayed release solid dosage form is desired, is suitably selected from a carrier having a viscosity of at least 20 mPa·s, suitably at least 40 mPa·s, suitably at least 50 mPa·s, though suitably having a viscosity of no more than 300 mPa·s, suitably no more than 210 mPa·s—suitably a viscosity between 20 and 300 mPa·s, suitably between 40 and 210 mPa·s. The extrudable carrier(s), especially where a delayed release solid dosage form is desired, is suitably selected from a carrier having a molecular weight of at least 10,000 g/mol, suitably at least 15,000, though suitably less than 400,000 g/mol—in a particular embodiment the molecular weight is between 10,000 and 400,000 g/mol, suitably between 10,000 and 25,000 g/mol, whereas in other embodiments the molecular weight is between 100,000 and 350,000 g/mol. The extrudable carrier(s), especially where a delayed release solid dosage form is desired, is suitably selected from a carrier having a glass transition temperature (Tg) of at least 80° C., suitably at least 90° C., suitably at least 100° C., though suitably at most 200° C., suitably at most 160° C.—suitably a Tg between 50 and 200° C., suitably between 90 and 160° C. In some embodiments, the active ingredient carrier(s) may not have a glass transition temperature as such, though observed softening may still occur. The extrudable carrier(s), especially where a delayed release solid dosage form is desired, is suitably selected from:

an (optionally alkyl-, suitably methyl- or ethyl-) acrylate, methacrylate and/or ethacrylate polymer or copolymer (suitably free of any amine-containing monomeric units), suitably with a viscosity between 90 and 210 mPa·s, suitably with a molecular weight between 100,000 and 350,000 g/mol, and/or suitably with a glass transition temperature between 90 and 140° C.; wherein the relevant polymer or copolymer is suitably selected from: poly(methacylic acid-co-ethyl acrylate), suitably in a respective monomeric molar ratio of 1:1 (+/−5% for each molar value of the ratio); poly(methacylic acid-co-methyl methacrylate), suitably in a respective monomeric molar ratio of 1:1 (+/−5% for each molar value of the ratio); poly(methacylic acid-co-methyl methacrylate), suitably in a respective monomeric molar ratio of 1:2 (+/−5% for each molar value of the ratio); or a cellulose or cellulose derivative, suitably a hydroxypropyl methylcellulose (HPMC) derivative, most suitably a hydroxypropyl methylcellulose (HPMC) acetate succinate (HPMCAS), suitably with a molecular weight between 10,000 and 25,000 g/mol and/or suitably with a glass transition temperature between 100 and 145° C. (or suitably between 100 and 165° C.); wherein the relevant HPMCAS is suitably selected from Aqoat LG, Aqoat MG, and/or Aqoat HG. Suitably HPMC derivatives may, however, also include hydroxypropylmethylcellulose phthalate (HPMCP), such as HP-50, HP-55 and HP-55S grades thereof.

In principle any suitably extrudable carrier(s) may be used, including any one or more of those selected from an (optionally alkyl-, suitably methyl- or ethyl-) acrylate, methacrylate and/or ethacrylate copolymer (suitably comprising amine-containing monomeric units); an (optionally alkyl-, suitably methyl- or ethyl-) acrylate, methacrylate and/or ethacrylate polymer or copolymer (suitably free of any amine-containing monomeric units); a cellulose or cellulose derivative; polyvinyl alcohol (PVA); poly(lactic-co-glycolic acid) (PLGA); and/or any suitable pharmaceutical acceptable carrier.

(Optionally alkyl-, suitably methyl- or ethyl-) acrylate, methacrylate and/or ethacrylate polymer or copolymers are particularly advantageous at supporting high loadings of the active ingredient.

The extrudable carrier(s) is suitably selected from Eudragit E, Eudragit NE, HPC SSL, Eudragit RS, Eudragit RL, HPC SL, HPC M, HPC H, Eudragit L100-55, Eudragit L100, Eudragit S100, Aqoat LG, Aqoat MG, Aqoat HG, and/or polyvinyl alcohol (PVA), or any combination of any of the aforementioned.

In some embodiments, especially where an active ingredient has limited solubility in a target solubilisation medium (e.g. in the body), extrudable carrier(s) such as polyvinylpyrrolidone polymers or polyvinylpyrrolidone-derived polymers may be employed. Such polymers can facilitate dissolution of an active ingredient that may otherwise exhibit limited solubility. In a particular embodiment, PVP K29-32 (a povidone) may be used. When present, suitably a PVP or PVP-based carrier is present (e.g. in an extrudable composition) at a concentration of between 20 and 80 wt %, suitably at a concentration between 40 and 60 wt %, suitably 45-55 wt %. PVP and PVP-based carrier polymers may be used alongside one or more filler(s), and optionally with other ingredients such as plasticizer(s). Mixtures of different PVP or PVP-based carriers may also or alternatively be used (e.g. PVPs of different molecular weights).

In some embodiments, polyalkyleneglycol and polyalkyleneglycol-derived polymers may be employed as a extrudable carrier. In a particular embodiment the polyalkyleneglycol or polyalkyleneglycol-derived carrier polymer is a polyethyleneglycol (PEG) or polyethyleneglycol-derived carrier polymer. Suitably, wherever a PEG or PEG-based carrier polymer is deployed, at least a portion of the PEG or PEG-based carrier polymer has a molecular weight of at least 100,000, though suitably at most 1,000,000, suitably between 100,000 and 1,000,000. However, a mixture of different polyalkyleneglycol and polyalkyleneglycol-derived polymers (e.g. PEG or PEG-based carrier polymers) may be incorporated within filaments and/or corresponding dosage forms. For instance, a high molecular weight PEG may be used alongside a relatively low molecular weight PEG to achieve an optimal balance of properties. Higher molecular weight PEG and PEG-based polymers (e.g. $M_w \geq 80,000$) can serve as carrier molecules, whereas lower molecular weight PEG and PEG-based polymers (e.g. $M_w$ 200-20000) may serve as plasticizers and/or solubility enhancers. Increasing the proportions of lower molecular weight PEGs is likely to lower the $T_g$ of the resulting filament. Moreover, increasing the proportions of lower $M_w$ PEGs also favours accelerated drug release. Suitably any PEG or PEG-based carrier polymers are used alongside one or more filler(s), though such polymers may be used with or without non-melting components.

Suitably the extrudable carrier is a pharmaceutically acceptable polymer (or GRAS approved polymer). The extrudable carrier may comprise one or more thermoplastics. The extrudable carrier may comprise one or more pharmaceutically acceptable polymers selected from the group consisting of: (optionally alkyl-) acrylate, methacrylate or ethacrylate polymer or copolymer, optionally comprising amine-containing monomeric units, silicones, polyurethanes, polyolefins (e.g. polystyrene), polyalkylene glycols, polyalkyleneglycol-derived polymer or copolymer, a polyvinylpyrrolidone or polyvinylpyrrolidone-derived polymer or co-polymer, polyvinyl alcohol, polyamides, acrylonitrile butadiene styrene (ABS), polylactic acid (PLA), polyglycolide, nylon, and/or co-polymers or mixtures thereof. The list is by no means exhaustive. Suitably the extrudable carrier is polyvinyl alcohol.

Suitably, the extrudable composition of the invention comprises greater than or equal to 10%, 20%, 30%, 40%, 50%, 60%, 70%, or 80% weight by weight of the extrudable carrier. Suitably, the extrudable composition comprises less than or equal to 99%, 95%, 90%, 80%, or 60% by weight of the extrudable carrier. Suitably, the extrudable composition comprises between 10 and 95% weight of the extrudable carrier.

Suitably, the extruded item of the invention comprises greater than or equal to 10%, 20%, 30%, 40%, 50%, 60%, 70%, or 80% by weight of the extrudable carrier. Suitably, the extruded item comprises less than or equal to 99%, 95%, 90%, 80%, or 60% by weight of the extrudable carrier. Suitably, the extruded item comprises between 10 and 95% weight of the extrudable carrier.

More than one extrudable carrier (optionally as defined herein) may be used.

Temporary Plasticiser

The temporary plasticiser allows the extrudable composition to be extruded at lower temperatures by reducing the glass transition (or softening) temperature of the extrudable composition (i.e., reducing the extrusion temperature required to form the extruded item and/or extrudable element). Advantageously, this allows thermally sensitive components and/or components to be used in the extrudable compositions and extruded items. For example, thermally sensitive active ingredients. Additionally, this allows active ingredients and/or other components to be used which have low melting points, for example having a lower melting point relative to the extrudable carrier.

Suitably the temporary plasticiser may result in the physical properties of the extruded item and/or extrudable element being altered, such as the glass transition temperature of the extrudable item and/or extrudable element being reduced. This can result in the physical properties of the extruded item and/or extrudable element not being optimal for subsequent handling, for example, if the glass transition temperature of the extruded item and/or extrudable element is too low, the extruded item and/or extrudable element can be very flexible. Advantageously, the temporary plasticiser may be removed or partially removed during the method to prepare the extruded item and/or extrudable element, for example during or after extrusion. This can result in the physical properties of the extruded item and/or extrudable element being altered depending on how much of the temporary plasticiser is removed, for example, the glass transition temperature of the extruded item and/or extrudable element being increased thereby resulting in the extruded item and/or extrudable element being less flexible. Therefore, the physical properties of the extrudable element and/or the extruded item can be controlled through altering the levels of the temporary plasticiser contained in them.

Suitably, the temporary plasticiser is a vaporisable substance (or a combination of vaporisable substances) capable of being vaporised at a temperature at or below 150° C. (suitably at standard ambient pressure, e.g. 100 kPa). Suitably the or each vaporisable substance is a liquid, suitably a solvent or water. Suitably the solvent is a pharmaceutically, nutraceutically, or food supplement acceptable grade solvent. Suitably, the temporary plasticiser has a boiling point less than or equal to 150° C., such as less than or equal to 140° C., 130° C., 120° C., 110° C., 105° C., or 100° C. (suitably at standard ambient pressure e.g., 100 kPa). Suitably, the temporary plasticiser has a boiling point of between 25 and 150° C. (suitably at standard ambient pressure e.g., 100 kPa). In one embodiment, the temporary plasticiser is a pharmaceutically acceptable grade solvent or water (e.g. distilled water). Suitably, the pharmaceutically acceptable grade solvent is an ICH Class 3 solvent (International Council for Harmonisation of Technical Requirements for Pharmaceuticals for Human Use, ICH Harmonised Guideline; Impurities: Guideline for Residual Solvents Q3C(R6)). Suitably, the temporary plasticiser is ethanol. Suitably, the temporary plasticiser is water.

The other components of the extrudable composition and/or the extruded item may contain residual levels of the temporary plasticiser, for example, residual water in the extrudable carrier. It is it be understood that the amounts defined herein of the temporary plasticiser present in the extrudable composition and the extruded item may include any contributions from the other components present.

Suitably, the extrudable composition comprises greater than or equal to 0.1%, 0.2%, 0.5%, 0.8%, 1%, 2%, 3%, 4%, 5%, 6%, 7%, 8%, 9%, 10%, 12%, 15%, 18%, 20%, 25% or 30% by weight of the temporary plasticiser. Suitably, the extrudable composition comprises less than or equal to 50%, 40%, 30%, 20%, 15%, 10%, 5%, 4%, 3%, or 2% by weight of the temporary plasticiser. Suitably, the extrudable composition comprises 0.1 to 50% of the temporary plasticiser.

Suitably, the extruded item comprises greater than or equal to 0.1%, 0.2%, 0.5%, 0.8%, 1%, 2%, 3%, 4%, 5%, 6%, 7%, 8%, 9%, 10%, 15%, 20%, 25% or 30% by weight of the temporary plasticiser. Suitably, the extruded item comprises less than or equal to 50% 40%, 30%, 20%, 15%, 10%, 5%, 4%, 3%, or 2% by weight of the temporary plasticiser. Suitably, the extruded item comprises 0.1 to 50% of the temporary plasticiser.

Suitably, the extruded item has a lower level of the temporary plasticiser than the extrudable composition used to prepare the extruded item, suitably 10%, 20%, 20%, 30%, 40%, 50%, 60%, 70%, 80%, 90%, 95%, or 99% lower.

More than one temporary plasticizer (optionally as defined herein) may be used.

In a particular embodiment, the extrudable composition may be used to form an extrudable element, such as a 3D-printable filament. Though the composition of such an extrudable element may conform to that set forth herein in relation to the extrudable composition, in some embodiments such an extrudable element may contain a lower concentration of temporary plasticiser than the extrudable composition used to produce the extrudable element, and in some embodiments may be substantially free or free of temporary plasticiser. Suitably the extrudable elements still reap the benefits of the present invention, for instance, by being formed at lower temperatures than they otherwise would be had temporary plasticiser not been present in the precursor extrudable composition used to prepare the extrudable element.

Permanent Plasticiser

In one embodiment, the extrudable composition and/or the extruded item further comprises a permanent plasticiser. A permanent plasticiser is a plasticiser which is not removed during the manufacturing process of preparing the extruded item and/or extrudable composition. The permanent plasticiser reduces the glass transition (or softening) temperature of the extrudable composition thereby resulting in a lower extrusion temperature being used in forming the extruded item or in forming an extrudable element. Use of both a permanent plasticiser and a temporary plasticiser allows an even lower extrusion temperature being utilised relative to the use of either alone. In these instances, the extrudable compositions and extruded items of the present invention can be used in conjunction with other components, such as active ingredients, which are particularly thermally sensitive.

Suitably the permanent plasticiser is a pharmaceutically acceptable plasticiser. Many pharmaceutically acceptable plasticisers are known in the art for use in the formation of pharmaceutical extruded items (i.e. solid dosage forms).

Suitably the permanent plasticiser has a melting point lower than the melting melt of the extrudable carrier. Suitably the melting point of the permanent plasticiser is less than or equal to 140° C., suitably less than or equal to 130° C., 120° C., 110° C., or 100° C. Suitably the melting point of the permanent plasticiser is between 0 and 140° C., suitably between 50 and 140° C.

Suitably the permanent plasticiser has a glass transition (softening) temperature lower than the glass transition (softening) temperature of the extrudable carrier. Suitably the glass transition (softening) temperature of the permanent plasticiser is less than or equal to 100° C., 90° C., 80° C., 70° C., 60° C., 50° C., 40° C., 30° C., 20° C., 10° C., 0° C., or −10° C. Suitably the glass transition (softening) temperature of the permanent plasticiser is −10 to 100° C.

Suitably the permanent plasticiser is a pharmaceutically, nutraceutically, or food supplement acceptable grade excipient.

Suitably the permanent plasticiser may be selected from selected from one or more of triethylcitrate (TEC), glycerol, castor oil, oleic acid, glycerol, tryacetin, polyalkylene glycols (e.g. a polyethylene glycol or polypropylene glycol, such as PEG400), and a sugar alcohol with the general formula of $HOCH_2(CHOH)_nCH_2OH$ wherein n is between 2 and 12. Suitably the sugar alcohol is selected from ethylene glycol, glycerol, erythritol, threitol, arabitol, xylitol, ribitol, mannitol, sorbitol, galactitol, fucitol, iditol, inositol, volemitol, isomalt, maltitol, and maltotritol. Suitably the permanent plasticiser is sorbitol or triethylcitrate.

Certain permanent plasticizers may be more appropriate than others, depending on the particular extrudable carrier, temporary plasticiser, active ingredient if present, and other components if present.

Suitably the extrudable composition and/or extruded item comprises at least or equal to 1% 2%, 4%, 5%, 8%, or 10% by weight of the permanent plasticiser. Suitably the extrudable composition and/or extruded item comprises 1% to 50% by weight, suitably 1% to 25%, suitably 1% to 10% of the permanent plasticiser of the total weight of the extrudable composition and/or extruded item.

More than one permanent plasticizer (optionally as defined herein) may be used.

Active Ingredient

The at least one active ingredient is suitably a pharmaceutical drug substance (which may be any suitable pharmaceutical compound or pharmaceutically acceptable salt, solvate (including hydrate), prodrug, or polymorph thereof). As such, any extrudable carriers, temporary plasticisers, permanent plasticisers, and/or other components within the extrudable composition are suitably pharmaceutically acceptable extrudable carriers, temporary plasticisers, permanent plasticisers, and/or other components.

The at least one active ingredient is suitably in the same form (and has substantially the same purity) as the active ingredient is in approved drug products.

In a particular embodiment, the at least one active ingredient is very soluble, freely soluble, or soluble in accordance with the standard USP (United States Pharmacopeia) definitions for solubility. In another embodiment, the at least one active ingredient is sparingly soluble, slightly soluble, or very slightly soluble in accordance with the standard USP definitions for solubility.

In a particular embodiment, the at least one active ingredient is very soluble in accordance with the standard USP definitions for solubility.

In a particular embodiment, the at least one active ingredient is freely soluble in accordance with the standard USP definitions for solubility.

In a particular embodiment, the at least one active ingredient is soluble in accordance with the standard USP definitions for solubility.

In a particular embodiment, the at least one active ingredient is sparingly soluble in accordance with the standard USP definitions for solubility.

In a particular embodiment, the at least one active ingredient is slightly soluble in accordance with the standard USP definitions for solubility.

In a particular embodiment, the at least one active ingredient is very slightly soluble in accordance with the standard USP definitions for solubility.

In a particular embodiment, the at least one active ingredient is practically insoluble in accordance with the standard USP definitions for solubility.

In a particular embodiment, the at least one active ingredient is thermally sensitive. In one embodiment, the at least one active ingredient is prone to thermal degradation at a temperature greater than the temperature the extrudable composition will be exposed to during the method to prepare an extruded item and/or extrudable element as defined herein. In one embodiment, the at least one active ingredient is prone to thermal degradation at a temperature greater than or equal to 90° C., 100° C., 110° C., 120° C., 130° C., 140° C., 150° C., 160° C., 180° C., or 200° C. Suitably, the at least one active ingredient is prone to thermal degradation at a temperature of 90 to 200° C. Such thermal degradation is suitably discernible by techniques known in the art, for example, DSC.

Suitably the active ingredient is a small molecule active ingredient. Suitably the active ingredient is a biologic active ingredient, such as a protein or peptide.

In a particular embodiment, the extrudable composition and/or extruded item comprises one active ingredient. In another embodiment, the extrudable composition and/or extruded item comprises two active ingredients.

Suitably, extruded items of the invention comprise greater than or equal to 0.5 wt %, 1 wt %, 5 wt %, 10 wt %, 20 wt %, or 40 wt % active ingredient. Suitably, extruded items of the invention comprise less than or equal to 60 wt %, 50% wt, or 30% wt active ingredient. Suitably, extruded items of the invention comprise 0.5 to 50% wt of active ingredient.

Suitably, the extrudable composition(s) of the invention comprise greater than or equal to 0.5 wt %, 1 wt %, 5 wt %, 10 wt %, 20 wt %, or 40 wt % of active ingredient. Suitably, the extrudable composition(s) of the invention comprise less than or equal to 60 wt %, 50% wt, or 30% wt active ingredient. Suitably, the extrudable composition(s) of the invention comprise 0.5% wt to 60 wt % active ingredient.

Other Components

In a particular embodiment, the extrudable composition and/or extruded item further comprises one or more other components. Other components may suitably include one or more excipients, excipients carriers, and/or diluents, all of which may be included in the extruded item.

In particular, the one or more other components within the extrudable composition and/or extruded item may be selected from one or more fillers/diluents, antiadherants, binders, disintegrants, lubricants, glidants, flavourants, preservatives, sweeteners, colourants, and coatings.

Fillers/diluents, antiadherants, binders, disintegrants, lubricants, glidants, flavourants, preservatives, sweeteners, colourants, and coatings are known in the art of pharmaceuticals, nutraceuticals and food supplements, and any of these may be deployed where appropriate or desired for a particular pharmaceutical, nutraceutical or food supplement formulation.

Suitably the fillers/diluents, antiadherants, binders, disintegrants, lubricants, glidants, flavourants, preservatives, sweeteners, colourants, and coatings are substantially inert, and/or suitably have minimal or no interaction with other component(s) of the extruded item and/or the extrudable composition.

Suitable antiadherants may include magnesium stearate. Suitable diluents/fillers may include plant cellulose, dibasic calcium phosphate, vegetable fats and oils, lactose, sucrose, glucose, mannitol, sorbitol, calcium carbonate, magnesium stearate, and/or microcrystalline cellulose. Suitable binders may include saccharides; polysaccharides/derivatives thereof, for example, starches, cellulose or modified cellulose such as microcrystalline cellulose and cellulose ethers such as hydroxypropyl cellulose, hydroxypropyl methyl cellulose, and derivatives thereof; sugar alcohols, for example, xylitol, sorbitol or maltitol; synthetic polymers, for example, polyvinylpyrrolidone (PVP), polyethylene glycol (PEG)). Suitable disintegrants may include crosslinked polyvinylpyrrolidone (crospovidone), crosslinked sodium carboxymethyl cellulose, croscarmellose sodium, modified starch sodium and/or starch glycolate. Suitable lubricants may include silica; sodium stearyl fumarate; fats, e.g. vegetable stearin; magnesium stearate or stearic acid; and/or talc. Suitable glidants may include fumed silica, talc, magnesium carbonate, and/or colloidal silica. Suitable coatings may include tablet coatings to protect tablet ingredients from deterioration by moisture in the air and make large or unpleasant-tasting tablets easier to swallow (e.g. a cellulose ether hydroxypropyl methylcellulose (HPMC) film coating; synthetic polymers, shellac, corn protein zein or other polysaccharides, gelatin; enteric coatings, for example, including fatty acid(s), wax(es), shellac, plastics, plant fibres). Suitable colourants may include curcumin, riboflavin, riboflavin-5'-phosphate, tartrazine, quinoline yellow, sunset yellow FCF, Cochineal, azorubine, amaranth, ponceau 4R, erythrosine, allura red AC, patent blue V, indigotine, brilliant blue FCF, chlorophylls, copper complexes of chlorophylls, green S, plain caramel, caustic sulphite caramel, ammonia caramel, sulphite ammonia caramel, brilliant black BN, vegetable carbon, brown HT, carotenes, annatto, paprika extract, lycopene, beta-apo-8'-carotenal, lutein, canthaxanthin, beetroot red, anthrocyanins, calcium carbonate, titanium dioxide, iron oxides and hydroxides, aluminium, silver, gold and/or litholrubine BK. The generic classes of excipients are well understood by those skilled in the art.

A solid oral dosage form may be designed to release the active portion of the formulation at the point in the gastrointestinal tract where bioavailability is maximized and presystemic degradation is minimized. At least one additional agent may be included to facilitate absorption of an active of the disclosure and/or any additional therapeutic agents. In such solid dosage forms, the active compound is typically mixed with at least one inert, pharmaceutically acceptable excipient or carrier such as lactose, sodium citrate or dicalcium phosphate and/or one or more: a) fillers or extenders for example starches, lactose, sucrose, glucose, mannitol and silicic acid; b) binders for example carboxymethylcellulose, alginates, gelatin, polyvinylpyrrolidone, sucrose and acacia; c) humectants for example glycerol; d) disintegrating agents for example agar-agar, calcium carbonate, potato or tapioca starch, alginic acid, certain silicates and sodium carbonate; e) solution retarding agents for example paraffin; f) absorption accelerators for example quaternary ammonium compounds; g) wetting agents for example cetyl alcohol and glycerol monostearate; h) absorbents for example kaolin and bentonite clay and i) lubricants for example talc, calcium stearate, magnesium stearate, solid polyethylene glycols, sodium lauryl sulfate and mixtures thereof. Solid compositions of a similar type may also be employed as fillers in soft and hard-filled gelatin capsules using such excipients as lactose or high molecular weight polyethylene glycol, for example.

Such excipients may be chosen to suit the properties of the extruded item, the properties of the extrudable composition, or both, or a judicious compromise between both. For instance, in terms of the extruded item (i.e., solid dosage form), excipient(s) may be chosen for ease of administration to the target patient population(s) by the intended route;

improved dosing compliance; consistency and control of drug bioavailability; to enable bioavailability; improved active ingredient stability including protection from degradation; to ensure a robust and reproducible physical product. In terms of an extrudable composition (e.g. filaments for use in 3D printing), excipient(s) may be chosen to optimise the physical form and/or stability of the extrudable composition; to ensure a robust and reproducible physical products; flexibility and rigidity of the extrudable composition (an optimal balance between flexibility and rigidity of a filament is desirable to ensure that the filament can be conveyed successfully to an extrusion nozzle but then easily extruded from the nozzle); to enable production of optimal extruded item (e.g. as per the aforementioned points).

Suitably the extruded item comprises a coating. Suitably the coating protects the internal contents of the extruded from light, moisture and/or air (i.e., oxygen). Suitably the coating is a lubricant as herein define.

Applications of Extruded Item

The extruded item of the invention may take a variety of forms, though most suitably the extruded item is a solid dosage form, most suitably, the solid dosage form of a pharmaceutical, a nutraceutical and/or a food supplement solid dosage form.

In a particular embodiment, the extruded item is a pharmaceutical solid dosage form.

In a particular embodiment, the extruded item is an extruded item for use in the manufacture of a medicament.

The present invention also provides a method of treating and/or preventing a disease, condition, or disorder in a subject in need of such treatment. The method suitably comprises administering a therapeutically effective amount of the extruded item to the subject. Suitable the subject is an animal or human subject, most suitably a human subject. Suitably there is provided an extruded item for use as a medicament.

Suitably, the extruded item is an immediate release pharmaceutical solid dosage form for oral administration.

Packing of Extrudable Composition(s)

Extrudable composition(s) of the invention may be packaged by any one of a number of methods well known in the art. For example, cartridges for use in extruders can be preloaded with the extrudable composition(s). Advantageously, the cartridges can be prepared at a different site to where the extruder is situated and can be inserted into the extruder as and when required. Thus, when the extruder is located at different site, the user of the extrusion apparatus, for example a pharmacist, can select the appropriate extrudable composition package(s), insert said package(s) into the extrusion apparatus, and prepare an extruded item using said extrudable composition and extruder.

Suitably there is provided an extrudable composition package comprising:
 i. An extrudable composition comprising an extrudable carrier and a temporary plasticiser; and
 ii. A container, wherein the container contains the extrudable composition.

Suitably there is provided an extrudable composition package comprising:
 i. An extrudable composition comprising an extrudable carrier and a temporary plasticiser; and
 ii. A syringe wherein the syringe contains the extrudable composition.

Suitably there is provided an extrudable composition package comprising:
 i. An extrudable composition comprising an extrudable carrier and a temporary plasticiser; and
 ii. A cartridge, wherein the cartridge contains the extrudable composition.

Suitably the container is adapted to fit into the extrusion apparatus, suitably so the contents of the container (e.g. the extrudable composition) can be conveyed through the extruder. In one embodiment, the container is adapted so the contents of the container (e.g. the extrudable composition) can be conveyed to the extrusion nozzles of the extruder.

In one embodiment, the container comprises extrusion nozzles.

Suitably, the container is a cartridge, suitably a 3D printer cartridge. Suitably the cartridge contains the extrudable composition wherein the extrudable composition is in the form of a filament. Suitably, the cartridge contains the extrudable composition wherein the extrudable composition is in the form of a plurality of mini-tablets. Suitably, the cartridge contains the extrudable composition wherein the extrudable composition is in the form of a extrudable fluid.

Suitably, the container is a syringe and the extrudable composition is a extrudable fluid.

Suitably, the container is a heatable syringe. Advantageously, the syringe can be heated to form a extrudable fluid in situ.

Advantageously, when the container is a syringe and is filled with the extrudable fluid (either added to the syringe directly or formed in situ by heating), the syringe can act as an extruder, for example, it is possible to use the syringe to do direct ink writing.

Suitably there is provided an extrudable composition package, comprising one or more extrudable compositions, as defined herein, wherein the one or more extrudable compositions are optionally the same or different, within a packaging.

Suitably there is provided a method of producing an extrudable composition package, the method comprising packaging one or more extrudable compositions as defined herein, wherein the one or more extrudable compositions are optionally the same or different.

Suitably there is provided an extrudable composition package, obtainable by, obtained by, or directly obtained by the method of producing an extrudable composition package as defined herein.

Packaging of Extruded Item(s)

Extruded item(s) of the invention may be packaged by any one of a number of methods well known in the art. Where, for example, pharmaceutical solid dosage forms according to the invention are produced via extrusion apparatus situated in a pharmacy (e.g. to provide a patient with customised medicaments on-demand), the pharmacist may package the extruded item (e.g. solid dosage form) in a number of ways, including in tablet bottles, or even monitored dosing systems which may be subsequently dispatched to hospitals, care homes, and the like for ultimate dispensation to a patient.

Suitably there is provided a method of producing an extruded item package, the method comprising packaging one or more extruded items as defined herein, wherein the one or more extruded items are optionally the same or different.

Suitably there is provided an extruded item package, obtainable by, obtained by, or directly obtained by the method of producing an extruded item package as defined herein.

Suitably there is provided an extruded item package, comprising one or more extruded items, as defined herein, wherein the one or more extruded items are optionally the same or different, within a packaging.

In some embodiments, the packaging may be formed by the same or a different extrusion apparatus. In some examples, the packaging and extruded item may be produced simultaneously, whereby the extrusion operation utilises one or more extrudable composition(s) pertaining to the extruded item, and one or more extrudable compositions pertaining to the packaging, and the packaging may be built around the extruded item(s) during extrusion.

Preparing Filaments

A filament is suitably prepared by any one of the methods described in WO2016/038356 (by the present applicant). However, such methods reap the benefits of the present invention by utilising temporary-plasticizer-containing extrudable compositions in the production of filaments since, for instance, lower temperatures may be employed during hot-melt extrusions of the filaments.

Specific Embodiments of Extruded Item

Suitably, there is provided an extrudable composition comprising;
i. An extrudable carrier; and
ii. a temporary plasticiser.

Suitably, there is provided an extrudable composition comprising;
i. An extrudable carrier; and
ii. a temporary plasticiser having a boiling point less than or equal to 120° C.

Suitably, there is provided an extrudable composition comprising;
i. An extrudable carrier; and
ii. a temporary plasticiser;
wherein the temporary plasticiser is present at a level of greater than or equal to 5% by weight of the total extrudable composition weight.

Suitably, there is provided an extrudable composition comprising;
i. An extrudable carrier; and
ii. a temporary plasticiser;
wherein the temporary plasticiser is present at a level of greater than or equal to 10% by weight of the total extrudable composition weight.

Suitably, there is provided an extrudable composition comprising;
i. An extrudable carrier; and
ii. a temporary plasticiser;
wherein the temporary plasticiser is present at a level of greater than or equal to 15% by weight of the total extrudable composition weight.

Suitably, there is provided an extrudable composition comprising;
i. An extrudable carrier;
ii. a temporary plasticiser; and
iii. at least one active ingredient.

Suitably, there is provided an extrudable composition comprising;
i. An extrudable carrier;
ii. a temporary plasticiser;
iii. at least one active ingredient; and
iv. a permanent plasticiser.

Suitably, there is provided an extrudable composition comprising;
i. An extrudable carrier;
ii. a temporary plasticiser;
iii. at least one active ingredient;
iv. a permanent plasticiser; and
v. one or more other components, suitably an excipient, excipients carrier, and/or diluent.

Suitably, there is provided an extrudable composition comprising;
i. An extrudable carrier;
ii. a temporary plasticiser;
iii. at least one active ingredient;
iv. a permanent plasticiser; and
v. a colourant.

Suitably, there is provided an extrudable composition comprising;
i. at least 20% by weight of an extrudable carrier;
ii. greater than or equal to 1% by weight of a temporary plasticiser; and
iii. at least one active ingredient;
wherein the weights are relative to the total weight of the extrudable composition.

Suitably, there is provided an extrudable composition comprising;
i. at least 20% by weight of an extrudable carrier;
ii. greater than or equal to 1% by weight of a temporary plasticiser;
iii. at least one active ingredient; and
iv. at least 1% by weight of a permanent plasticiser;
wherein the weights are relative to the total weight of the extrudable composition.

Suitably, there is provided an extrudable composition comprising;
i. at least 20% by weight of an extrudable carrier;
ii. greater than or equal to 1% by weight of a temporary plasticiser;
iii. at least one active ingredient; and
iv. at least 10% by weight of a permanent plasticiser;
wherein the weights are relative to the total weight of the extrudable composition.

Suitably, there is provided an extrudable composition comprising;
i. at least 20% by weight of an extrudable carrier;
ii. greater than or equal to 1% by weight of a temporary plasticiser;
iii. at least one active ingredient;
iv. at least 10% by weight of a permanent plasticiser; and
v. one or more other components, suitably an excipient, excipients carrier, and/or diluent;
wherein the weights are relative to the total weight of the extrudable composition.

Suitably, there is provided an extrudable composition comprising;
i. an extrudable carrier selected from: (optionally alkyl-) acrylate, methacrylate or ethacrylate polymer or copolymer, optionally comprising amine-containing monomeric units, silicones, polyurethanes, polyolefins (e.g. polystyrene), polyalkylene glycols, polyalkyleneglycol-derived polymer or copolymer, a polyvinylpyrrolidone or polyvinylpyrrolidone-derived polymer or co-polymer, polyvinyl alcohol, polyamides, acrylonitrile butadiene styrene (ABS), polylactic acid (PLA), polyglycolide, nylon, and/or co-polymers or mixtures thereof;
ii. a temporary plasticiser having a boiling point less than or equal to 120° C.;
iii. at least one active ingredient; and
iv. a permanent plasticiser.

Suitably, there is provided an extrudable composition comprising;
i. polyvinyl alcohol;
ii. a temporary plasticiser selected from ethanol or water;
iii. at least one active ingredient; and
iv. sorbitol.

Suitably, there is provided an extrudable element comprising;
i. an extrudable carrier; and
ii. a temporary plasticiser.

Suitably, there is provided an extrudable element comprising;
i. an extrudable carrier; and
ii. a temporary plasticiser;
wherein the temporary plasticiser is present at a level of greater than or equal to 1% by weight of the total extrudable composition weight.

Suitably, there is provided an extrudable element comprising;
i. an extrudable carrier; and
ii. a temporary plasticiser;
wherein the extrudable element has a glass transition temperature of between −50° C. and 100° C.

Suitably, there is provided an extrudable element comprising;
i. an extrudable carrier; and
ii. a temporary plasticiser;
wherein the extrudable element has a glass transition temperature of between −15° C. and −10° C.

Suitably, there is provided an extrudable element comprising;
i. an extrudable carrier; and
ii. a temporary plasticiser;
wherein the extrudable element is a filament.

Suitably, there is provided an extrudable element comprising;
i. an extrudable carrier;
ii. a temporary plasticiser; and
iii. at least one active ingredient;
wherein the extrudable element is a filament.

Suitably, there is provided an extrudable element comprising;
i. an extrudable carrier;
ii. a temporary plasticiser;
iii. at least one active ingredient; and
iv. a permanent plasticiser
wherein the extrudable element is a filament.

Suitably, there is provided an extrudable compressed form comprising;
i. an extrudable carrier; and
ii. a temporary plasticiser.

Suitably, there is provided an extrudable compressed form comprising;
i. an extrudable carrier; and
ii. a temporary plasticiser;
wherein the extrudable compressed form is a tablet or a plurality of tablets.

Suitably, there is provided an extrudable compressed form comprising;
i. an extrudable carrier;
ii. a temporary plasticiser; and
iii. at least one active ingredient;
wherein the extrudable compressed form is a tablet or a plurality of tablets.

Suitably, there is provided an extrudable compressed form comprising;
i. an extrudable carrier;
ii. a temporary plasticiser;
iii. at least one active ingredient; and
iv. a permanent plasticiser;
wherein the extrudable compressed form is a tablet or a plurality of tablets.

Suitably, there is provided an extrudable compressed form comprising;
i. an extrudable carrier; and
ii. a temporary plasticiser;
wherein the extrudable compressed form has a weight of 10 to 100 mg.

Suitably, there is provided an extrudable fluid comprising;
i. an extrudable carrier; and
ii. a temporary plasticiser.

Suitably, there is provided an extrudable fluid comprising;
i. an extrudable carrier;
ii. a temporary plasticiser; and
iii. at least one active ingredient.

Suitably, there is provided an extrudable fluid comprising;
i. an extrudable carrier;
ii. a temporary plasticiser;
iii. at least one active ingredient; and
iv. a permanent plasticiser.

Suitably, there is provided an extrudable fluid comprising;
v. an extrudable carrier; and
vi. a temporary plasticiser;
wherein the extrudable fluid is a fluid at ambient temperature.

Suitably, there is provided an extrudable fluid comprising;
i. an extrudable carrier; and
ii. a temporary plasticiser;
wherein the extrudable fluid is a fluid at an elevated temperature.

Suitably, there is provided an extrudable fluid comprising;
i. an extrudable carrier; and
ii. a temporary plasticiser;
wherein the extrudable fluid is a fluid at a temperature greater than or equal to 80° C.

Suitably, there is provided an extruded item comprising;
i. an extrudable carrier; and
ii. a temporary plasticiser.

Suitably, there is provided an extruded item comprising;
i. an extrudable carrier;
ii. a temporary plasticiser; and
iii. at least one active ingredient.

Suitably, there is provided an extruded item comprising;
i. an extrudable carrier; and
ii. a temporary plasticiser;
wherein the temporary plasticiser is present at a level greater than or equal to 1% by weight of the total extruded item weight.

Suitably, there is provided an extruded item comprising;
i. an extrudable carrier;
ii. a temporary plasticiser; and
iii. at least one active ingredient;
wherein the temporary plasticiser is present at a level greater than or equal to 1% by weight of the total extruded item weight.

Suitably, there is provided an extruded item comprising;
i. an extrudable carrier;
ii. a temporary plasticiser;
iii. at least one active ingredient; and
iv. a permanent plasticiser;
wherein the temporary plasticiser is present at a level greater than or equal to 1% by weight of the total extruded item weight.

Suitably, there is provided a pharmaceutical, nutraceutical, or food supplement solid dosage form comprising;
i. an extrudable carrier;
ii. a temporary plasticiser and;
wherein the temporary plasticiser is present at a level greater than or equal to 1% by weight of the total extruded item weight.

Suitably, there is provided a pharmaceutical, nutraceutical, or food supplement solid dosage form comprising;
i. an extrudable carrier; and
ii. a temporary plasticiser;

Suitably, there is provided a pharmaceutical, nutraceutical, or food supplement solid dosage form comprising;
i. an extrudable carrier;
ii. a temporary plasticiser;
iii. at least one active ingredient; and
iv. a permanent plasticiser;
wherein the temporary plasticiser is present at a level greater than or equal to 1% by weight of the total extruded item weight.

Suitably, there is provided an extruded item comprising;
i. an extrudable carrier;
ii. a temporary plasticiser;
iii. at least one active ingredient; and
iv. a permanent plasticiser;
wherein the temporary plasticiser is present at a level greater than or equal to 5% by weight of the total extruded item weight and wherein the extruded item is a solid dosage form.

Suitably, there is provided an extruded item comprising;
i. At least 20% by weight of an extrudable carrier;
ii. Greater than or equal to 1% by weight of a temporary plasticiser;
iii. at least one active ingredient; and
iv. at least 10% by weight of a permanent plasticiser;
wherein the weights are relative to the total weight of the extruded item.

Suitably, there is provided an extruded item comprising;
i. At least 20% by weight of an extrudable carrier;
ii. Greater than or equal to 5% by weight of a temporary plasticiser;
iii. at least one active ingredient; and
iv. at least 10% by weight of a permanent plasticiser;
wherein the weights are relative to the total weight of the extruded item.

Suitably, there is provided an extruded item comprising;
i. an extrudable carrier;
ii. a temporary plasticiser;
iii. at least one active ingredient; and
iv. a permanent plasticiser;
wherein the temporary plasticiser is present at a level greater than or equal to 1% by weight of the total extruded item weight and wherein the extruded item is a solid dosage form comprising a plurality of layers, wherein each layer has a thickness of between 10 and 1000 μm.

Suitably, there is provided an extruded item comprising;
i. an extrudable carrier;
ii. a temporary plasticiser;
iii. at least one active ingredient;
iv. a permanent plasticiser; and
v. a coating
wherein the temporary plasticiser is present at a level greater than or equal to 1% by weight of the total extruded item weight and wherein the extruded item is a solid dosage form.

Suitably, there is provided an extruded item comprising;
i. an extrudable carrier selected from: (optionally alkyl-) acrylate, methacrylate or ethacrylate polymer or copolymer, optionally comprising amine-containing monomeric units, silicones, polyurethanes, polyolefins (e.g. polystyrene), polyalkylene glycols, polyalkyleneglycol-derived polymer or copolymer, a polyvinylpyrrolidone or polyvinylpyrrolidone-derived polymer or co-polymer, polyvinyl alcohol, polyamides, acrylonitrile butadiene styrene (ABS), polylactic acid (PLA), polyglycolide, nylon, and/or co-polymers or mixtures thereof;
ii. a temporary plasticiser having a boiling point less than or equal to 120° C.;
iii. at least one active ingredient; and
iv. a permanent plasticiser;
wherein the temporary plasticiser is present at a level greater than or equal to 1% by weight of the total extruded item weight and wherein the extruded item is a solid dosage form.

Suitably, there is provided a method of preparing an extrudable composition, the method comprising;
i. Mixing an extrudable carrier and a temporary plasticiser together; and
ii. further processing the mixture from step i. to form:
a. an extrudable fluid;
b. an extrudable compressed form; or
c. an extrudable element.

Suitably, there is provided a method of preparing an extrudable composition, the method comprising;
i. Mixing an extrudable carrier and a temporary plasticiser together; and
ii. Optionally further processing the mixture from step i. to form:
a. an extrudable fluid;
b. an extrudable compressed form; or
c. an extrudable element;
wherein the extrudable composition has at least 20% by weight of the extrudable carrier; less than or equal to 30% by weight of a temporary plasticiser; and wherein the weights are relative to the total weight of the extrudable composition.

Suitably, there is provided a method of preparing an extrudable composition, the method comprising;
i. Mixing an extrudable carrier, a temporary plasticiser, and at least one active ingredient together; and
ii. Optionally further processing the mixture from step i. to form:
a. an extrudable fluid;
b. an extrudable compressed form; or
c. an extrudable element;
wherein the extrudable composition has at least 20% by weight of the extrudable carrier; less than or equal to 30% by weight of a temporary plasticiser; and wherein the weights are relative to the total weight of the extrudable composition.

Suitably, there is provided a method of preparing an extrudable composition, the method comprising;
i. Mixing an extrudable carrier, a temporary plasticiser, at least one active ingredient, and a permanent plasticiser together; and
ii. Optionally further processing the mixture from step i. to form:
a. an extrudable fluid;
b. an extrudable compressed form; or
c. an extrudable element.

Suitably, there is provided a method of preparing an extrudable composition, the method comprising;
  i. Mixing an extrudable carrier, a temporary plasticiser, at least one active ingredient, and a permanent plasticiser together; and
  ii. Optionally further processing the mixture from step i. to form:
    a. an extrudable fluid;
    b. an extrudable compressed form; or
    c. an extrudable element;
  wherein the extrudable composition has at least 20% by weight of the extrudable carrier; less than or equal to 30% by weight of a temporary plasticiser; at least 10% by weight of the permanent plasticiser; and wherein the weights are relative to the total weight of the extrudable composition.

Suitably, there is provided a method of preparing an extrudable composition, the method comprising;
  i. Mixing an extrudable carrier and a temporary plasticiser together.

Suitably, there is provided a method of preparing an extrudable composition, the method comprising;
  i. Mixing an extrudable carrier and a temporary plasticiser together; and
  ii. further processing the mixture from step i. to form:
    a. an extrudable fluid.

Suitably, there is provided a method of preparing an extrudable composition, the method comprising;
  i. Mixing an extrudable carrier and a temporary plasticiser together; and
  ii. further processing the mixture from step i. to form:
    a. an extrudable compressed form.

Suitably, there is provided a method of preparing an extrudable composition, the method comprising;
  i. Mixing an extrudable carrier and a temporary plasticiser together; and
  ii. further processing the mixture from step i. to form:
    a. an extrudable element.

Suitably, there is provided a method of preparing an extrudable composition, the method comprising;
  i. Mixing an extrudable carrier and a temporary plasticiser together; and
  ii. Optionally further processing the mixture from step i. to form:
    a. an extrudable fluid;
    b. an extrudable compressed form; or
    c. an extrudable element;
  wherein the mixing is shear mixing.

Suitably, there is provided a method of preparing an extrudable composition, the method comprising;
  i. Mixing an extrudable carrier and a temporary plasticiser together; and
  ii. Optionally further processing the mixture from step i. to form:
    a. an extrudable fluid;
    b. an extrudable compressed form; or
    c. an extrudable element;
  wherein the mixing is shear mixing wherein mixing is performed at a temperature greater than or equal to 10° C.

Suitably, there is provided a method of preparing an extrudable composition, the method comprising;
  i. Mixing an extrudable carrier and a temporary plasticiser together; and
  ii. Optionally further processing the mixture from step i. to form:
    a. an extrudable fluid;
    b. an extrudable compressed form; or
    c. an extrudable element;
  wherein the mixing is shear mixing and the temporary plasticiser is sprayed on to the extrudable carrier during the mixing step.

Suitably, there is provided a method of preparing an extrudable composition, the method comprising;
  i. Mixing an extrudable carrier and a temporary plasticiser together; and
  ii. further processing the mixture from step i. to form:
    a. an extrudable fluid;
  wherein the extrudable fluid is a fluid at ambient temperature.

Suitably, there is provided a method of preparing an extrudable composition, the method comprising;
  i. Mixing an extrudable carrier and a temporary plasticiser together; and
  ii. further processing the mixture from step i. to form:
    b. an extrudable fluid;
  wherein the extrudable fluid is a fluid at elevated temperatures.

Suitably, there is provided a method of preparing an extrudable composition, the method comprising;
  i. Mixing an extrudable carrier and a temporary plasticiser together; and
  ii. Filing a container with the mixture from step i.

Suitably, there is provided a method of preparing an extrudable fluid, the method comprising;
  i. Mixing an extrudable carrier and a temporary plasticiser together;
  ii. Filing a container with the mixture from step i; and
  iii. Heating the container.

Suitably, there is provided a method of preparing an extrudable fluid, the method comprising;
  i. Mixing an extrudable carrier and a temporary plasticiser together;
  ii. Filing a container with the mixture from step i; and
  iii. Heating the container;
  wherein the container is a syringe.

Suitably, there is provided a method of preparing an extrudable fluid, the method comprising;
  i. Mixing an extrudable carrier and a temporary plasticiser together;
  ii. Filing a container with the mixture from step i; and
  iii. Heating the container to a temperature greater than the glass transition (or softening) temperature of the mixture formed from step i.

Suitably, there is provided a method of preparing an extrudable fluid, the method comprising;
  i. Mixing an extrudable carrier and a temporary plasticiser together;
  ii. Filing a container with the mixture from step i; and
  iii. Heating the container to a temperature greater than the glass transition (or softening) temperature of the mixture formed from step i.;
  wherein the container is a syringe.

Suitably, there is provided a method of preparing an extrudable composition, the method comprising;
  i. Mixing an extrudable carrier and a temporary plasticiser together; and
  ii. further processing the mixture from step i. to form:
    a. an extrudable compressed form.

Suitably, there is provided a method of preparing an extrudable composition, the method comprising;
  i. Mixing an extrudable carrier and a temporary plasticiser together; and
  ii. further processing the mixture from step i. to form:
    a. an extrudable compressed form;
  wherein the compressed form is a tablet or a plurality of tablets.

Suitably, there is provided a method of preparing an extrudable element, the method comprising;
  i. Mixing an extrudable carrier and a temporary plasticiser together; and
  ii. Extruding the mixture from step i.; and
  iii. Removing or partially removing the temporary plasticiser from the product from step ii.

Suitably, there is provided a method of preparing an extrudable element, the method comprising;
  i. Mixing an extrudable carrier and a temporary plasticiser together; and
  ii. Extruding the mixture from step i.; and
  iii. Removing or partially removing the temporary plasticiser from the product from step ii;
  wherein the extrudable element is a filament.

Suitably, there is provided a method of preparing an extrudable element, the method comprising;
  i. Mixing an extrudable carrier and a temporary plasticiser together; and
  ii. Extruding the mixture from step i.; and
  iii. Removing or partially removing the temporary plasticiser from the product from step ii. so that the extruded element has a glass transition (softening) temperature between −50° C. and 100° C.

Suitably, there is provided a method of preparing an extrudable element, the method comprising;
  i. Mixing an extrudable carrier and a temporary plasticiser together; and
  ii. Extruding the mixture from step i.; and
  iii. Removing or partially removing the temporary plasticiser from the product from step ii. so that the extruded element has a glass transition (softening) temperature between −15° C. and −10° C.

Suitably, there is provided a method of preparing an extrudable element, the method comprising;
  i. Mixing an extrudable carrier and a temporary plasticiser together; and
  ii. Extruding the mixture from step i.; and
  iii. Removing or partially removing the temporary plasticiser by heating the product from step ii. and/or holding the product from step ii. under reduced pressure until the extruded element has a glass transition (softening) temperature between −15° C. and −10° C.

Suitably, there is provided a method of preparing an extruded item, the method comprising;
  i. Extruding an extrudable composition into a desired form, wherein the extrudable composition is as defined herein optionally in association with one or more supplementary elements (e.g. a shell, coating, core);
  wherein:
  the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

Suitably, there is provided a method of preparing an extruded item, the method comprising;
  i. Extruding an extrudable composition into a desired form, wherein the extrudable composition comprises an extrudable carrier and a temporary plasticiser, optionally in association with one or more supplementary elements (e.g. a shell, coating, core);
  wherein:
  the temporary plasticiser is a vaporisable substance (or combination of vaporisable substances) capable of being vaporised at a temperature at or below 150° C. (suitably at standard ambient pressure e.g., 100 kPa); and the method further comprises removing or partially removing the temporary plasticiser.

Suitably, there is provided a method of preparing an extruded item, the method comprising;
  i. Extruding an extrudable composition into a desired form, wherein the extrudable composition comprises an extrudable carrier and a temporary plasticiser, optionally in association with one or more supplementary elements (e.g. a shell, coating, core);
  wherein:
  the temporary plasticiser is a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

Suitably, there is provided a method of preparing an extruded item, the method comprising;
  i. Extruding an extrudable composition into a desired form, wherein the extrudable composition comprises at least 20% by weight of an extrudable carrier and less than or equal to 30% by weight of a temporary plasticiser, optionally in association with one or more supplementary elements (e.g. a shell, coating, core);
  wherein:
  the weights are relative to the total weight of the extrudable composition;
  the temporary plasticiser is a vaporisable substance (or combination of vaporisable substances) capable of being vaporised at a temperature at or below 150° C. (suitably at standard ambient pressure e.g., 100 kPa); and
  the method further comprises removing or partially removing the temporary plasticiser, via vaporisation.

Suitably, there is provided a method of preparing an extruded item, the method comprising;
  i. Extruding an extrudable composition into a desired form, wherein the extrudable composition comprises an extrudable carrier, a temporary plasticiser, and at least one active ingredient, optionally in association with one or more supplementary elements (e.g. a shell, coating, core);
  wherein:
  the temporary plasticiser is a vaporisable substance (or combination of vaporisable substances) capable of being vaporised at a temperature at or below 150° C. (suitably at standard ambient pressure e.g., 100 kPa); and
  the method further comprises removing or partially removing the temporary plasticiser, via vaporisation.

Suitably, there is provided a method of preparing an extruded item, the method comprising;
  i. Extruding an extrudable composition into a desired form, wherein the extrudable composition comprises at least 20% by weight of an extrudable carrier, less than or equal to 30% by weight of a temporary plasticiser, and at least one active ingredient, optionally in association with one or more supplementary elements (e.g. a shell, coating, core);
wherein:
the weights are relative to the total weight of the extrudable composition;
the temporary plasticiser is a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form, wherein the extrudable composition comprises at least 20% by weight of an extrudable carrier, less than or equal to 30% by weight of a temporary plasticiser, and at least an active ingredient, optionally in association with one or more supplementary elements (e.g. a shell, coating, core);
wherein:
the extruded item is a pharmaceutical, nutraceutical or food supplement solid dosage form;
the weights are relative to the total weight of the extrudable composition;
the temporary plasticiser is a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form, wherein the extrudable composition comprises an extrudable carrier, a temporary plasticiser, at least one active ingredient, and a permanent plasticiser, optionally in association with one or more supplementary elements (e.g. a shell, coating, core);
wherein:
the temporary plasticiser is a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form, wherein the extrudable composition comprises at least 20% by weight of an extrudable carrier, less than or equal to 30% by weight of a temporary plasticiser, at least one active ingredient, and at least 10% by weight of a permanent plasticiser, optionally in association with one or more supplementary elements (e.g. a shell, coating, core);
wherein:
the extruded item is a pharmaceutical, nutraceutical or food supplement solid dosage form;
the weights are relative to the total weight of the extrudable composition;
the temporary plasticiser is a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form, wherein the extrudable composition comprises an extrudable carrier, and a temporary plasticiser, optionally in association with one or more supplementary elements (e.g. a shell, coating, core);
wherein:
the extruded item is a pharmaceutical, nutraceutical or food supplement solid dosage form;
the extruded item comprises a lower amount of the temporary plasticiser than the extrudable composition;
the temporary plasticiser is a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form, wherein the extrudable composition comprises at least 20% by weight of an extrudable carrier, and less than or equal to 30% by weight of a temporary plasticiser, optionally in association with one or more supplementary elements (e.g. a shell, coating, core;
wherein:
the extruded item is a pharmaceutical, nutraceutical or food supplement solid dosage form;
the extruded item comprises a lower amount of the temporary plasticiser than the extrudable composition;
the weights are relative to the total weight of the extrudable composition and wherein the temporary plasticiser is a vaporisable substance (or combination of vaporisable substances) capable of being vaporised at a temperature at or below 150° C. (suitably at standard ambient pressure e.g., 100 kPa);
and
the method further comprises removing or partially removing the temporary plasticiser, via vaporisation.

Suitably, there is provided a method of preparing an extruded item, the method comprising;
i. Extruding an extrudable composition into a desired form, wherein the extrudable composition comprises at least 20% by weight of an extrudable carrier, less than or equal to 30% by weight of a temporary plasticiser, and at least one active ingredient, optionally in association with one or more supplementary elements (e.g. a shell, coating, core);
wherein:
the extruded item is a pharmaceutical, nutraceutical or food supplement solid dosage form;
the extruded item comprises a lower amount of the temporary plasticiser than the extrudable composition;
the weights are relative to the total weight of the extrudable composition;
the temporary plasticiser is a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

Suitably, there is provided a method of preparing an extruded item, the method comprising;
i. Extruding an extrudable composition into a desired form, wherein the extrudable composition comprises at least 20% by weight of an extrudable carrier, less than or equal to 30% by weight of a temporary plasticiser, at least one active ingredient, and at least 10% by weight of a permanent plasticiser, optionally in association with one or more supplementary elements (e.g. a shell, coating, core);
wherein:
the extruded item is a pharmaceutical, nutraceutical or food supplement solid dosage form;
the extruded item comprises a lower amount of the temporary plasticiser than the extrudable composition;
the weights are relative to the total weight of the extrudable composition;
the temporary plasticiser is a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form, wherein the extrudable composition comprises at least 20% by weight of an extrudable carrier, less than or equal to 30% by weight of a temporary plasticiser, at least one active ingredient, and at least 10% by weight of a permanent plasticiser, optionally in association with one or more supplementary elements (e.g. a shell, coating, core);
herein:
the extruded item is a pharmaceutical, nutraceutical or food supplement solid dosage form;
the extruded item has 10% less of the temporary plasticiser than the extrudable composition;
the weights are relative to the total weight;
the temporary plasticiser is a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form, wherein the extrudable composition is as defined herein;
wherein:
the extruded item is a pharmaceutical, nutraceutical, or food supplement solid dosage form;
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable element, optionally in association with one or more supplementary elements (e.g. a shell, coating, core), into a desired form, wherein the extrudable element is as defined herein;
wherein:
the extrudable element initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

Suitably, there is provided a method of preparing an extruded item, the method comprising;
i. Extruding an extrudable compressed form into a desired form, wherein the extrudable compressed form is as defined herein;
wherein:
the extrudable compressed form initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and the method further comprises removing or partially removing the temporary plasticiser, via vaporisation.

Suitably, there is provided a method of preparing an extruded item, the method comprising;
i. Extruding an extrudable fluid into a desired form, wherein the extrudable fluid is as defined herein;
wherein:
the extrudable fluid initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form onto a build platform, wherein the extrudable composition is as defined herein;
wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising;
i. Extruding an extrudable composition into a desired form wherein the extrudable composition is as defined herein; and
ii. Heating the desired form from step i. and/or holding the desired from step i. under reduced pressure so to remove or partially remove the temporary plasticiser;
wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa).

Suitably, there is provided a method of preparing an extruded item, the method comprising;
i. Extruding an extrudable composition into a desired form wherein the extrudable composition is as defined herein); and
ii. Heating the desired form from step i. and/or holding the desired from step i. under reduced pressure so that at least 10% by weight of the temporary plasticiser is removed;

wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa).

Suitably, there is provided a method of preparing an extruded item, the method comprising;
i. Extruding an extrudable composition into a desired form wherein the extrudable composition is as defined herein and wherein the desired from is built up layer by layer;

wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation.

Suitably, there is provided a method of preparing an extruded item, the method comprising:
i. providing an extrudable composition comprising an extrudable carrier; and
ii. extruding the extrudable composition into a desired form optionally in association with one or more supplementary elements (e.g. a shell, coating, core);

wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation from the extruded item prior, during or after the step of extruding.

Suitably, there is provided a method preparing a pharmaceutical, nutraceutical, or food supplement solid dosage form, the method comprising:
i. providing an extrudable composition comprising an extrudable carrier; and
ii. extruding the extrudable composition into a desired form optionally in association with one or more supplementary elements (e.g. a shell, coating, core);

wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa); and
the method further comprises removing or partially removing the temporary plasticiser, via vaporisation from the extruded item prior, during or after the step of extruding.

Suitably, there is provided a method preparing an extruded item, the method comprising:
i. providing a container filled with an extrudable composition comprising an extrudable carrier;
ii. extruding the extrudable composition into a desired form optionally in association with one or more supplementary elements (e.g. a shell, coating, core);

wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa);
the extrudable composition is transformed in situ, suitably via heating of the container, or provided as an extrudable fluid; and
the method further comprises removing or partially removing the temporary plasticiser, via vaporisation from the extruded item prior, during or after the step of extruding.

Suitably, there is provided a method preparing an extruded item, the method comprising:
i. providing an extrudable composition comprising an extrudable carrier;
ii. extruding the extrudable composition into a desired form optionally in association with one or more supplementary elements (e.g. a shell, coating, core) by an extruder;

wherein:
the extrudable composition initially comprises a temporary plasticiser, the temporary plasticiser being a vaporisable substance (or combination of vaporisable substances) capable of being vaporised at a temperature at or below 150° C. (suitably at standard ambient pressure e.g., 100 kPa);
the extruder comprises a heatable build platform;
the method further comprises removing or partially removing the temporary plasticiser, via vaporisation from the extruded item during or after the step of extruding by heating the build platform to a temperature above ambient.

In an embodiment, an extrudable item is produced by direct ink 3D printing of an extrudable compressed form, wherein said extrudable compressed form is suitably a plurality of compressed units (e.g. minitablets) or a compressed monolith (e.g. compressed powder or compressed granular composition). The extrudable composition may optionally comprise or, prior to 3D printing, be mixed with a temporary plasticizer, but in certain embodiments the extrudable composition is free of or is not mixed with a temporary plasticizer. Suitably, in such embodiments, each minitablet has a longest dimension of between 0.5 mm and 10 mm, suitably between 1 mm and 8 mm, suitably between 3 mm and 7 mm, most suitably between 5 mm and 7 mm. Suitably each extrudable compressed form weighs 10 to 100 mg, 20 to 80 mg, 30 to 70 mg, 40 to 60 mg, or about 50 mg. Suitably each extrudable compressed form is formed by compressing 10 to 100 mg, 20 to 80 mg, 30 to 70 mg, 40 to 60 mg, or about 50 mg of an otherwise powdered or granulated extrudable composition.

Suitable any extrudable composition defined herein comprises either or both a temporary and/or permanent plasticizer, suitably as defined herein. Whenever a temporary plasticizer is used, it is suitably ultimately removed or partially removed after processing into the desired form (e.g. extruded item). Whenever a permanent plasticizer is used it suitably remains in the ultimate desired form into which it is processed.

Embedded Items

Method of Preparing an Embedded Item

The present invention provides a method of preparing an embedded item, suitably as defined herein.

There is provided a method of preparing an embedded item, the method comprising:
  i. Providing a solidifiable body substance in a fluid or a semi-fluid form;
  ii. Embedding within the solidifiable body substance an embeddable substance;
  iii. Solidifying the solidifiable body substance with the embeddable substance therein.

Suitably the embedded item is as defined herein.

The method suitable comprises operating the embedding apparatus to produce an embedded solid on it, suitably upon the build platform, through the embedding of the embeddable substance within the solidifiable body substance.

Suitably, such production is performed via a computer-implemented process (i.e. where embedding is controlled and suitably initiated by a computer that is connected or connectable to or within the apparatus, be it in a wired or wireless fashion).

The embeddable substance suitably resides within the apparatus in a storage position, suitably within a container, such as cartridge. The embeddable substance is suitably conveyed to the deposition nozzle, suitably by one or more conveyors (e.g. a pump or a syringe). The deposition nozzle suitably penetrates the provided solidifiable body substance or passes over the surface of a portion of the solidifiable body substance, and the embeddable substance is then passed through the deposition nozzle into the solidifiable body substance or onto a surface of the portion of solidifiable body substance (suitably whilst the embeddable substance continues to be conveyed towards the deposition nozzle from a storage position). The embeddable substance is deposited within/onto the solidifiable substance in at least one layer, suitably in a single layer or in a plurality of layers. If the embeddable substance is deposited onto a surface of the solidifiable body substance, another portion of the solidifiable body substance is placed onto the first portion thus embedding the embeddable substance within the solidifiable body substance. Suitably the embeddable substance is deposited in a continuous manner per layer (e.g. line), or a non-continuous manner (e.g. dots or portions of a pattern which may be connected or separate). Suitably a pattern of the embeddable substance is formed per layer within the solidifiable body substance. Due to the immiscibility of the embeddable substance with the solidifiable body substance the embeddable substance remains where it was deposited within the solidifiable body substance, that is there is no appreciable migration of the embeddable substance within the solidifiable body substance during the process to make the embedded item. Suitably there is no appreciable migration of the embeddable substance within the solidifiable body substance during the shelf life of the embedded item. Suitably there is no appreciable migration of the embeddable substance within the solidifiable body substance for at least 1 hour after production of the embedded item, suitably at least 2 hours, 4 hours, 8 hours, 12 hours, 24 hours, 48 hours, 72 hours, 7 days, 14 days, 1 month, 2 months, 3 months, 4 months, 6 months, 8 months, 10 months, 12 months, 18 months, or 24 months. Suitably there is no appreciable migration of the embeddable substance within the solidifiable body substance for 1 hour to 24 months after production of the embedded item. The term no appreciable migration is to be understood as no migration, or migration which does not affect the suitably of the embedded item for its intended use, i.e., as a dosage form. The skilled person would be aware of techniques in the art which can determine the levels of migration of the embeddable substance within the solidifiable substance, for example by visual monitoring by eye or by microscopy, monitoring the concentration profile of the embeddable substance within the embedded item using spectroscopy.

The deposition nozzle is suitably moved during the embedding step suitably in any or all of the X, Y, Z direction.

The solidifiable body substance suitably resides within the apparatus in a storage position, suitably within a container, such as cartridge. The solidifiable body substance is suitably conveyed to the deposition nozzle, suitably by one or more conveyors (e.g. a pump or a syringe). The deposition nozzle suitably provides solidifiable body substance by filling of a mould with the solidifiable body substance.

It will be understood by those skilled in the art that the, each, or any deposition nozzle may be adapted to suit the properties a corresponding embeddable substance/solidifiable body substance configured to embed/provide thereto. The nozzle properties/design and embeddable substance properties/solidifiable body substance suitably complement one another so as to facilitate controlled embedding/provision of said composition (be it continuous or intermittent, e.g. where more than one embeddable substance/solidifiable body substance is used), suitably without any deposition nozzle blockages or impedance, and suitably without any unacceptable degradation of ingredients within the embeddable substance/solidifiable body substance during the embedding/providing steps.

Suitably the method comprises embedding the embeddable substance into the solidifiable body substance after the solidifiable body substance has been solidified. For example, the solidifiable body substance is solidified and then embeddable body substance is embedded (i.e., by printing using a needle which pieces the solidified body substance) into the solidified body substance, thereby incorporating the embeddable body substance within the solidified body substance.

Suitably the method comprises embedding the embeddable substance within the solidifiable body substance by solidifying a portion of the solidifiable body substance, providing the embeddable substance onto a surface of the solidified body substance (i.e., by direct printing on the top surface), providing the remaining solidifiable body substance on top of the solidified body substance, and solidifying the remaining portion solidifiable body substance thereby embedding the embeddable substance between the two portions of the body substance.

Providing a Solidifiable Body Substance

Suitably the solidifiable body substance is as defined herein.

Suitably the providing step is performed at an elevated temperature, suitably at a temperature greater than or equal to ambient temperature. Suitably at a temperature greater than or equal to 25° C., 30° C., 40° C., 50° C., 60° C., 70° C., or 80° C. Suitably the providing step is performed at 25 to 80° C.

Suitably the solidifiable body substance is at a temperature greater than or equal ambient temperature, suitably at a temperature greater than or equal to 25° C., 30° C., 40° C., 50° C., 60° C., 70° C., or 80° C. Suitably the solidifiable body substance is at a temperature of 25 to 80° C.

Suitably the solidifiable body substance is heated in step i. Suitably the solidifiable body substance is heated to a temperature greater than or equal to ambient temperature. Suitably at a temperature greater than or equal to 25° C., 30°

C., 40° C., 50° C., 60° C., 70° C., or 80° C. Suitably the solidifiable body substance is heated in step i. to a temperature of 25 to 80° C.

Suitably the providing step comprises filling or partially filling a mould with the solidifiable body substance. Suitably the mould is sized and shaped to produce an embedded item sized and shaped as defined herein. Suitably the solidifiable body substance is poured into the mould.

Suitably the mould is held at a temperature greater than or equal to ambient temperature, suitably at a temperature greater than or equal to 25° C., 30° C., 40° C., 50° C., 60° C., 70° C., or 80° C. Suitably the mould is held at a temperature of 25 to 80° C.

Suitably the solidifiable body substance is provided at a temperature greater than the temperature of the mould. Suitably the solidifiable body substance is provided at a temperature of at least 10° C. higher than the temperature of the mould, suitably at least 15° C., 20° C., 25° C., or 30° C. higher.

Suitably more than one solidifiable body substances is used in the providing of a solidifiable body substance step.

Embedding Step

Suitably the embeddable substance is as defined herein.

Suitably more than one embeddable substance is used in the embedding step.

Suitably the embedding step comprises embedding the embeddable substance in at least one layer or partial layer within the solidifiable body substance. Suitably, there is one layer of the embeddable substance, suitably a plurality of layers, suitably two layers.

Suitably the embeddable substance comprises at least one active ingredient. Suitably each layer may comprise one or more active ingredients. Suitably, if there is more than one layer present, each layer may comprise different active ingredients. Suitably, if there is more than one layer present, each layer may be the same or different.

Suitably each layer is a continuous layer or a non-continuous layer. Suitably each layer may be in the form of a straight, curved, or intermittent layer (such as a dotted layer). Suitably each layer may be in the form of a continuous line, suitably a continuous straight line, suitably a continuous line comprising bends and/or curves.

Suitably the embedding step uses a printer, suitably a 3D-printer, suitably an embedded 3D-printer. Suitably the printer comprises a printing plate. Suitably the embedded item is formed on the printing plate, suitably within a mould on the printing plate.

Suitably the embedding step uses at least one syringe. Suitably the syringe is filled with the embeddable substance.

Suitably the embedding step is performed at a temperature less than or equal to 60° C., suitably less than or equal to 50° C., 40° C., 30° C., or 25° C. Suitably the embedding step is performed at a temperature of 0 to 50° C., such as 25 to 50° C. Advantageously, the embeddable substance is not exposed to very high temperatures during the embedding step. This is particularly useful for embeddable substances which comprises a thermally sensitive component, such as a thermally sensitive active ingredient, such as a biologic active ingredient, i.e., a protein or peptide.

Suitably each embedding step is continuous.

Suitably the embeddable substance is present within the solidifiable body substance in at least one layer or at least one partial layer.

Suitably the method comprises two or more embedding steps, each embedding step comprising embedding within the solidifiable body substance an embeddable substance, wherein the embeddable substance used in each embedding step is the same or different. Suitably each embedding step forms different layers of the embeddable substance within the solidifiable body substance. Suitably each embedding step forms part of the same layer of the embeddable substance within the solidifiable body substance.

Suitably each embedding step embeds a portion of the embeddable substance within the solidifiable body substance. Suitably the embedding step comprises embedding a portion of the embeddable substance within the solidifiable body substance followed by embedding at least another portion of the embeddable substance. Suitably the portions are the same or different. Suitably the embedding step comprises embedding at portion of the embeddable substance within the solidifiable body substance followed by three other portions. Suitably each portion embeds about 25% of the embeddable substance within the solidifiable body substance. For example, about 25% of the embeddable substance is embedded within the solidifiable body substance followed by another about 25% portion, followed by another about 25% portion and finally another about 25% portion. The portions of the embeddable substance may be joined or not joined within the solidifiable body substance. Suitably the embedding step comprises embedding a first layer, or portion thereof, of the embeddable substance within the solidifiable body substance followed by embedding a second layer, or portion thereof, of the embeddable substance within the solidifiable body substance. Suitably the first and second layers are distinct with the solidifiable body substance (i.e., the layers are separated by the solidifiable body substance) or are in contact with each other.

Suitably, the embedding step of each portion of the embeddable substance is digitally controlled, i.e., by a computer. Advantageously, embedding the embeddable substance in portions results in less variation during the embedding process of the amount of the embeddable substance dispensed, therefore resulting in a more accurate dose of the embeddable substance within the embedded item.

Suitably, the embedding step uses a needle. Suitably the needle size controls the amount of embeddable substance embedded in the solidifiable body substance. Suitably the needle size is 1 to 1.6 mm.

Suitably the amount of embeddable substance embedded in the solidifiable body substance is controlled by the embedding speed of the embedder. Suitably the embedding speed is between 40 and 80 mm/min, such as between 50 and 70 mm/min, suitably about 50 mm/min, suitably about 60 mm/min, suitably about 65 mm/min, suitably about 70 mm/min.

Suitably, the embeddable substance is embedded in the solidifiable body substance to produce a pattern, suitably a personalised pattern to the patient.

Suitably, the embeddable substance is embedded in the solidifiable body substance so to allow sequential release of the embeddable substance from the embedded item when the embedded item is administered, suitably orally administered. Suitably two embeddable substances are embedded so to allow sequential release of the embeddable substances.

Suitably, the embeddable substance is embedded in the solidifiable body substance so to allow dose titration of the embeddable substance from the embedded item when the embedded item is administered, suitably orally administered.

Solidifying Step

Suitably the solidifying step comprises UV curing, heating, cooling and/or providing a cross-linking agent.

Suitably the solidifying step comprises heating the solidifiable body substance, suitably heating the solidifiable body substance to above ambient temperature, suitably heating the solidifiable body substance to greater than or equal to 25° C., 30° C., 40° C., 50° C., 60° C., 70° C., 80° C., 90° C., or 100° C. Suitably the solidifying step comprises heating the solidifiable body substance to less than or equal to 200° C., 150° C., 120° C., or 100° C. Suitably the solidifying step comprises heating the solidifiable body substance to 25 to 200° C.

Suitably the solidifying step comprises cooling the solidifiable body substance, suitably cooling the solidifiable body substance to a temperature lower than temperatures used in the previous steps. Suitably the solidifying step comprises cooling the solidifiable body substance to a temperature below ambient temperature, suitably greater than or equal to −20° C., −10° C., 0° C., 10° C., or 20° C. Suitably the solidifying step comprises cooling the solidifiable body substance to a temperature less than or equal to 40° C., 30° C., 20° C., or 10° C. Suitably the solidifying step comprises cooling the solidifiable body substance to a temperature of between −20 and 40° C.

Suitably the solidifying step comprises UV curing, suitably by exposing the solidifiable body substance to UV light source. Suitably the exposure time is at least 1 minute, suitably at least 5 minutes, 10 minutes, 20 minutes, 30 minutes, or 60 minutes. Suitably the solidifying step comprises exposing the solidifiable body substance to UV light for 1 to 60 minutes. Suitably the UV light source is a UV lamp.

Suitably the solidifying step further comprises providing a cross-linking agent as defined herein. Suitably the cross-linking agent solidifies the solidifiable body substance. The skilled person will appreciate there are a number of agents which may act as a cross-linking agent and a number of agents which may act as a solidifiable body substance. The choice of both agents will depend on the compatibility of the agents with each other, and other components within the embedded item, as well their suitability for use in the method to prepare the embedded item and the desired attributes of the embedded item.

Suitably the solidifiable body substance comprises at least one active ingredient.

Additional Method Steps

The method may include one or more further steps before, during, and/or after any of the aforesaid steps. The external surface(s) of the embedded item may be pre- or post-treated, whether through the embedding of an additional layer or partial layer, or through alternative coating techniques well known in the art.

An embedded item produced via methods of the invention may be subsequently treated in a variety of ways to afford a further-processed embedded item. Suitably the method further comprises coating the product obtained from the embedding step. Suitably the coating is described herein. For instance, an embedded item may be enterically coated by standard enteric coating treatments known in the art. Likewise, other release-controlling properties may be imparted to an embedded item by further processing.

Most suitably, all steps (including any further processing steps) are performed by the embedding apparatus. Suitably all steps (including further processing steps) are suitably controlled by the same computer.

Computer-Implementation of Method

The method of preparing an embedded item is suitably a computer-implemented method, suitably as defined herein.

The method suitably involves providing an embedding apparatus, suitably as defined herein, and operating said apparatus to prepare the embedded item. Suitably the embedding apparatus includes or is otherwise connected to a computer. Operating the embedding apparatus suitably involves operating a computer, which is suitably connected (be it in a wired or wireless fashion) with or within the relevant embedding apparatus (so as to allow the computer to control and co-ordinate other parts of the embedding apparatus, including a printer).

A computer that is comprised of or otherwise associated with an embedding apparatus of the invention may be suitably referred to as an embedding control computer. The embedding control computer may serve a different function (and may be a distinct entity) to other "computers" referred to herein, such as monitoring computers and analytical computers, though a single computer may perform the function(s) of one or more of any combination of these computers. An embedding control computer suitably controls the preparation of the embedded item, for example the embedding of the embeddable substance within the solidifiable body substance through a deposition nozzle, and optionally further processing steps, for example coating of the item formed. Wherever a different computer is used to implement each of these operations, said computers are suitably co-ordinated and may thus be considered to be a part of one overall computer.

Preparing the embedded item is suitably controlled by a computer, running pursuant software, suitably based on information provided to the computer by user input(s) (drug type, drug dose level), databases (e.g. patient database and/or extruded item databases), and/or data files (e.g. design and/or parameter files), as described herein. Suitably an embedding apparatus is configured pursuant to instructions provided by the computer by: feeding the embeddable substance(s) and/or feeding the solidifiable body substances(s) to and through their respective deposition nozzle(s) at the appropriate intervals and/or at the appropriate rates; and by moving the deposition nozzle(s) and/or build platform to enable systematic embedding of the embeddable substance within the solidifying body substance in accordance with the relevant information obtained and calculations made by the computer.

The deposition nozzle(s) are suitably controlled by the computer according to the "obtained information" regarding the embedded item (e.g. design and/or other parameters). Deposition nozzles are suitably controlled to embed a given embeddable substance within the solidifiable body substance to a pattern pre-defined by the "obtained information". As such, the or each deposition nozzle may be controlled to switch "on" and "off" in accordance with a pre-defined schedule to deliver the required pattern in the construction of the embedded item. A deposition nozzle may be switched "on" by causing an output opening to open.

The build platform is suitably controlled by the computer according to the "obtained information" regarding the embedded item (e.g. design and/or other parameters), suitably as described elsewhere herein. This may include controlling the operating temperature of the build platform, in particular the operating temperature of the surface of the build platform. Suitably, during preparation of the embedded item, the operating temperature of the build platform or surface thereof is maintained substantially constant, suitably at a constant temperature+/−5° C., as required for that particular stage of the process. For example, during the filling or partial filling of the mould with the solidifiable substance the build platform may be held at a first temperature. During the solidifying stage, the build platform may be held at a second temperature. During the embedding stage, the build platform may be held a third temperature. Depending on how the solidifying of the solidifiable body substance is done, the first temperature may be higher than the second temperature and/or third temperature (e.g. solidifying is by cooling) or vice versa (e.g. solidifying is by heating). Suitably the first, second and third temperatures may be the same, for example when solidifying is by exposure to UV light and/or cross-linking. Additionally, such temperature control may facilitate adhesion of the developing embedded item to the surface of the build platform during its formation. Such temperature control may facilitate release (i.e. unsticking) of an embedded item after its formation (e.g. the surface of the build platform may be heated or cooled, as appropriate, to reduce adhesion of the embedded item(s) thereto). During the process of preparing an embedded item, the build platform is suitably configured or operable to maintain a surface temperature (i.e. for the surface in contact with the embedded item or the mould the embedded item is formed in) of less than or equal to 100° C., suitably less than or equal to 90° C., 80° C., 70° C., 60° C., 50° C., 40° C., 30° C., or 25° C. Suitably the surface temperature is greater than or equal to 0° C., suitably greater than or equal to 10° C., 20° C., 25° C., 30° C., 40° C., 50° C., or 60° C. Suitably the surface temperature is between 10 and 100° C.

Embedded Item

The present invention provides an embedded item obtainable by, obtained by, or directly obtained by the method of preparing an embedded item as defined herein.

The embedded item is suitably formed from the solidifiable substance and the embeddable substance. As such, any definitions herein relating to the solidifiable substance and the embeddable substance may be equally applicable to the embedded item per se.

There is provided an embedded item comprising an embeddable substance within a solidifiable body substance. Suitably the embedded item comprises one or more embeddable substance, suitably one embeddable substance, suitably two embeddable substances. Suitably each embeddable substance may comprise the same or different components, i.e., each embeddable substance may comprise the same or different active ingredients. Suitably the embedded item may comprise a plurality of solidifiable body substances, suitably two solidifiable body substances. Suitably each solidifiable body substance may be the same or different.

Suitably the embedded item comprises greater than or equal to 0.1%, 0.5%, 1%, 5%, 10%, 15%, 20%, 25% or 30% by weight of the embeddable substance, suitably between 1 to 30% by weight. Suitably the embedded item comprises greater than or equal to 10%, 20%, 30%, 40%, 50%, 60%, 70%, 80%, or 90% of the solidifiable body substance, suitably between 0.1 to 90% by weight.

Suitably the embedded item is a solid. Suitably the embedded item is a semi-solid. Suitably the embedded item is a solid or a semi-solid, suitably comprising a solid or semi-solid body (formed from the solidifiable body substance) and an embeddable substance within the body. Suitably the embeddable substance is a liquid, a solution, an emulsion, a suspension, a solid or a semi-solid (suitably a gel). Suitably the embeddable substance is a gel.

The embedded item(s) of the present invention are advantageously customisable in terms of the type/nature of active ingredient, the dose of active ingredient within the embedded item (be it an absolute dose per embedded item or the concentration of the active ingredient with the embedded item), the mass/volume of the embedded item (which is typically adaptable to vary the absolute dose of the active ingredient without changing the concentration of the active ingredient within the embedded item), the active ingredient release profile (which may be varied by judicious use and/or distribution of appropriate excipients), or shape and appearance (including novelty shapes, colours, and patterns, such as those that may help medical compliance for particular patients).

Suitably the embedded item comprises at least one active ingredient, suitably one active ingredient, suitably a plurality of active ingredients, suitably two active ingredients.

Suitably the embeddable substance comprises at least one active ingredient. Suitably the solidifiable body substance comprises at least one active ingredient. Suitably the solidifiable body substance comprises at least one active ingredient and the embeddable substance comprises at least one active ingredient wherein the active ingredients in the embeddable body substance and the solidifiable body substance are the same or are different.

Suitably, the embedded item is a solid dosage form, suitably a pharmaceutical, nutraceutical or food supplement solid dosage form, suitably a tablet. Suitably the tablet is a chewable tablet. Suitably the embedded item is a solid oral dosage form, most suitably, an immediate release solid dosage form. Suitably the embedded item is an extended release dosage form or a delayed release dosage form. Suitably the embedded item of the present invention are for oral administration.

Suitably the embedded item upon oral administration has an immediate, extended or delayed release profile.

Suitably, the solidifiable body substance provides gastric protection of the embeddable substance when the embedded item is orally administered.

The immediate release solid dosage form suitably releases at least 75% of the active ingredient(s) within a 45 minute period, suitably releases at least 85% of active ingredient(s) within a 30 minute period, and may suitably release at least 85% of the active ingredient(s) with a 15 minute period. The skilled person may refer to European Pharmacopeia 8.0. Strasbourg, France: Council of Europe; European Directorate for the Quality of Medicine; 2014 for further details.

Suitably the embeddable substance is fully within the solidifiable body substance. Suitably, the embeddable substance(s) is a layer or a portion of a layer within the solidifiable body substance, suitably a single layer (or portion of), suitably multiple layers (or portions of), suitably two layers (or portions of). Suitably the layer (or portion thereof) is a continuous or non-continuous. Suitably the embeddable substance is present as a straight line, curved line and/or intermittent (i.e. not continuous) in the layer. Suitably each layer may comprise one embeddable substance or multiple embedded substances. Suitably each layer may comprise at least one portion. Suitably if two or more layers are present, the layers are touching or are not touching, i.e., solidifiable body substance separates the layers or portion of layers.

Suitably each layer of the embeddable substance has a thickness of between 10 and 1000 μm, suitably between 20 and 800 μm, 30 and 600 μm, 40 and 500 μm, 50 and 400 μm, or 60 and 300 μm. Suitably each layer of the embeddable substance within the embedded item, if more than one layer is present, can have the same thickness or each layer can have a different thickness.

Suitably the shape of the embedded item is a cuboid, cube, or a cylinder.

Suitably the volume of the embedded item is suitably greater than or equal to 3 $mm^3$, 5 $mm^3$, 10 $mm^3$, 50 $mm^3$, 100 $mm^3$, or 200 $mm^3$. The volume of the embedded solid is suitably less than or equal to 500 $mm^3$, 300 $mm^3$, 250 mm³, 150 mm³, or 50 mm³. Suitably the volume of the embedded item is between 5 and 500 mm³.

The longest dimension ($D_{max}$) of the embedded item (e.g. whether in the X, Y, or Z direction) is suitably greater than or equal to 3 mm, 5 mm, 8 mm, 10 mm, or 12 mm. The longest dimension of the embedded item is suitably less than or equal to 30 mm, 25 mm, 20 mm, or 15 mm. The longest dimension of the embedded item is suitably between 3 and 30 mm.

The shortest dimension ($D_{min}$) of the embedded item (i.e. not necessarily the thinnest part but the maximum length of the thinnest dimension, or the shortest of the X, Y, or Z) is suitably greater than or equal to 0.1 mm, 0.5 mm, 1 mm, 3 mm, 5 mm, 8 mm, 10 mm, or 12 mm. The shortest dimension of the embedded item is suitably less than or equal to 30 mm, 25 mm, 20 mm, 15 mm, 10 mm, 8 mm, 5 mm, or 2 mm. The shortest dimension of the embedded item is suitably between 0.1 and 30 mm.

Suitably the embedded item has a weight of greater than or equal to 1 mg, suitably greater than or equal to 5 mg, 10 mg, 50 mg, or 80 mg. Suitably the embedded item has a weight of less than or equal to 1000 mg, suitably less than or equal to 500 mg, 250 mg, or 100 mg. Suitably the embedded item has a weight of 1-1000 mg.

Many of the features preferred of the embedded item are described elsewhere herein. For instance, features described in relation to the method of producing the embedded item may suitably reflect a feature of the embedded item itself (e.g. number of layers of the embeddable substance). Suitably the embedded item comprises ingredients provided by the solidifiable substance(s) and the embeddable substance(s) used in its formation and may be considered to comprise relevant solidifiable body substances and embeddable substances.

Suitably there is no migration of the embeddable substance into the solidifiable body substance. Suitably there is no migration during at least the process to prepare the embedded item, suitably at least until the embedded item is used by the end user (e.g. the patients administer the embedded item).

Suitably, the embedded item comprises at least one active ingredient, suitably two active ingredients.

Suitably the embedded item comprises 0.01 to 50%, 0.1 to 50%, 0.1-40%, 1-30%, 5-25%, 5-20%, 5-15%, 8-12%, or about 10% by weight of the active ingredient. Suitably the embedded item comprises less than or equal to 80%, 60%, or 50% by weight of the active ingredient. Suitably the embedded item comprises greater than or equal to 1%, 2%, or 5% by weight of the active ingredient.

Suitably, the embeddable substance is arranged in the embedded item to allow sequential release of the embeddable substance when the embedded item is administered to a patient, suitably orally administered.

Suitably, the embeddable substance is arranged in the embedded item to allow dose titration of the embeddable substance when the embedded item is administered to a patient, suitably orally administered. Suitably, the embeddable sub Solidifiable Body Substance There is provided a solidifiable body substance. Suitably the solidifiable body substance is a substance that solidifies when exposed to elevated temperatures, temperatures below ambient, UV-light and/or a cross-linking agent.

Suitably the solidifiable body substance is a fluid or a semi-fluid form at ambient and/or elevated temperatures, suitably greater than or equal to 25° C., 30° C., 40° C., 50° C., 60° C., or 70° C. Suitably the solidifiable body substance is a fluid or a semi-fluid form at a temperature of 25 to 70° C.

Suitably the solidifiable body substance solidifies when exposed to elevated temperatures, suitably temperatures above ambient temperature, suitably greater than or equal to 25° C., suitably 30° C., 35° C., 40° C., 50° C., 60° C., 70° C., 80° C., 90° C., or 100° C. Suitably the solidifiable body substance solidifies when exposed to temperatures less than or equal to 200° C., 150° C., 120° C., or 100° C. Suitably the solidifiable body substance solidifies when exposed to temperature of between 25 and 200° C.

Suitably the solidifiable body substance solidifies when exposed to temperatures below ambient temperature, suitably greater than or equal to −20° C., −10° C., 0° C., 10° C., or 20° C. Suitably the solidifiable body solidifies when exposed to temperatures less than or equal to 40° C., 30° C., 20° C., or 10° C. Suitably the solidifiable body substance solidifies when exposed to a temperature of −20 to 40° C.

Suitably the solidifiable body substance solidifies when exposed to UV-light.

Suitably the solidifiable body substance solidifies a cross-linking agent is present. Suitably the cross-linking agent is selected from ethylene glycol diacrylate, di(ethylene glycol) diacrylate, tetra(ethylene glycol) diacrylate, ethylene glycol dimethacrylate, di(ethylene glycol) dimethacrylate, tri(ethylene glycol) dimethacrylate, N,N'-methylenebisacrylamide, N,N'-(1,2-dihydroxyethylene)bisacrylamide, N-(1-Hydroxy-2,2-dimethoxyethyl)acrylamide and divinylbenzene. This list is not exhaustive. The skilled person would appreciate other cross-linking agents are available and the choice of the agent is dependent on the solidifiable body substance selected and the compatibility of the substance with other components present in the embedded item.

Suitably the solidifiable body substance is a gel. Suitably the solidifiable body substance is a gelatine matrix. Suitably the gelatine matrix comprises gelatine, glycerol and/or water. Suitably the solidifiable body substance comprises gelatine, glycerol and water. Suitably the solidifiable body substance comprises 10-40% w/v of gelatine, suitably 20-30% w/v, suitably about 25% w/v. Suitably the solidifiable body substance comprises 15-45% w/v of glycerol, suitably 25-35% w/v, suitably about 30% w/v. Suitably the solidifiable body substance comprises 30-60% w/v of water, suitably 40-50% w/v, suitably about 45% w/v. Suitably the solidifiable body substance comprises 10-40% w/v of gelatine, 15-45% w/v of glycerol, and 30-60% w/v of water.

Suitably the solidifiable body substance comprises at least one active ingredient. Suitably the solidifiable body substance comprises one active ingredient. Suitably the solidifiable body substance comprises a plurality of active ingredients. Suitably the active ingredient is a pharmaceutical, nutraceutical or a food supplement active ingredient. Suitably the active ingredient is thermally sensitive, for example, suitably the active ingredient is a biologic, suitably a pharmaceutical biologic. Suitably the biologic is a protein or a peptide. Suitably the active ingredient is a small molecule, suitably a pharmaceutically active small molecule. Suitably the active ingredient is stable in the solidifiable body substance, for example, the active ingredient is stable in the solidifiable body substance from the point of the solidifiable body substance being prepared, during the process to prepare the embedded item, and at least until the point of use of the embedded item. Suitably, stable means less than or equal to a 0.05%, 0.1%, 0.5%, 1%, 2%, 3%, 4%, or 5% change in the active ingredient during the time frame mentioned above, for example 1 hour, 1 day, 1 week, 1 month, 3 months, 6 months or greater than 6 months.

Suitably the solidifiable body substance comprises 0.01 to 50%, 0.1 to 50%, 0.1-40%, 1-30%, 5-25%, 5-20%, 5-15%, 8-12%, or about 10% by weight of the active ingredient. Suitably the solidifiable body substance comprises less than or equal to 80%, 60%, or 50% by weight of the active ingredient. Suitably the solidifiable body substance comprises greater than or equal to 1%, 2%, or 5% by weight of the active ingredient.

Suitably the solidifiable body substance further comprises one or more other components. Other components may suitably include one or more excipients, excipients carriers, and/or diluents, all of which may be included in the solidifiable body substance.

Fillers/diluents, antiadherants, binders, disintegrants, lubricants, glidants, flavourants, preservatives, sweeteners, colourants, and coatings are known in the art of pharmaceuticals, nutraceuticals and food supplements, and any of these may be deployed where appropriate or desired for a particular pharmaceutical, nutraceutical or food supplement formulation.

Suitably the fillers/diluents, antiadherants, binders, disintegrants, lubricants, glidants, flavourants, preservatives, sweeteners, colourants, and coatings are substantially inert, and/or suitably have minimal or no interaction with other component(s) of the embedded item.

Suitable antiadherants may include magnesium stearate. Suitable diluents/fillers may include plant cellulose, dibasic calcium phosphate, vegetable fats and oils, lactose, sucrose, glucose, mannitol, sorbitol, calcium carbonate, magnesium stearate, and/or microcrystalline cellulose. Suitable binders may include saccharides; polysaccharides/derivatives thereof, for example, starches, cellulose or modified cellulose such as microcrystalline cellulose and cellulose ethers such as hydroxypropyl cellulose, hydroxypropyl methyl cellulose, and derivatives thereof; sugar alcohols, for example, xylitol, sorbitol or maltitol; synthetic polymers, for example, polyvinylpyrrolidone (PVP), polyethylene glycol (PEG)). Suitable disintegrants may include crosslinked polyvinylpyrrolidone (crospovidone), crosslinked sodium carboxymethyl cellulose, croscarmellose sodium, modified starch sodium and/or starch glycolate. Suitable lubricants may include silica; sodium stearyl fumarate; fats, e.g. vegetable stearin; magnesium stearate or stearic acid; and/or talc. Suitable glidants may include fumed silica, talc, magnesium carbonate, and/or colloidal silica. Suitable coatings may include tablet coatings to protect tablet ingredients from deterioration by moisture in the air and make large or unpleasant-tasting tablets easier to swallow (e.g. a cellulose ether hydroxypropyl methylcellulose (HPMC) film coating; synthetic polymers, shellac, corn protein zein or other polysaccharides, gelatin; enteric coatings, for example, including fatty acid(s), wax(es), shellac, plastics, plant fibres). Suitable colourants may include curcumin, riboflavin, riboflavin-5'-phosphate, tartrazine, quinoline yellow, sunset yellow FCF, Cochineal, azorubine, amaranth, ponceau 4R, erythrosine, allura red AC, patent blue V, indigotine, brilliant blue FCF, chlorophylls, copper complexes of chlorophylls, green S, plain caramel, caustic sulphite caramel, ammonia caramel, sulphite ammonia caramel, brilliant black BN, vegetable carbon, brown HT, carotenes, annatto, paprika extract, lycopene, beta-apo-8'-carotenal, lutein, canthaxanthin, beetroot red, anthrocyanins, calcium carbonate, titanium dioxide, iron oxides and hydroxides, aluminium, silver, gold and/or litholrubine BK. The generic classes of excipients are well understood by those skilled in the art.

Embeddable Substance

Suitably the embeddable substance is a liquid, a solution, a semi-solid (suitably a gel), an emulsion, a solid, or a suspension. Suitably the semi-solid is a gel.

Advantageously, this results in it being possible to prepare an embedded item using embedded 3D-printing. In particular, it is possible to prepare an embedded item without exposed the embeddable substance to high temperatures. This is particularly useful when the embeddable substance comprises thermal sensitive components, for example, thermally sensitive active ingredients, such as a biologic active ingredient, for example a protein or peptide.

Suitably the embeddable substance comprises at least one active ingredient. Suitably the embeddable substance comprises one active ingredient. Suitably the embeddable substance comprises a plurality of active ingredients. Suitably the active ingredient is a pharmaceutical, nutraceutical or a food supplement active ingredient. Suitably the active ingredient is thermally sensitive, for example, suitably the active ingredient is a biologic, suitably a pharmaceutical biologic. Suitably the biologic is a protein or a peptide. Suitably the active ingredient is a small molecule, suitably a pharmaceutically active small molecule. Suitably the active ingredient is stable in the embeddable substance, for example, the active ingredient is stable in the embeddable substance from the point of the embeddable substance being prepared, during the process to prepare the embedded item, and at least until the point of use of the embedded item. Suitably, stable means less than or equal to a 0.05%, 0.1%, 0.5%, 1%, 2%, 3%, 4%, or 5% change in the active ingredient during the time frame mentioned above, for example 1 hour, 1 day, 1 week, 1 month, 3 months, 6 months or greater than 6 months.

Suitably the embeddable substance comprises 0.01 to 50%, 0.1 to 50%, 0.1-40%, 1-30%, 5-25%, 5-20%, 5-15%, 8-12%, or about 10% by weight of the active ingredient. Suitably the embeddable substance comprises less than or equal to 80%, 60%, or 50% by weight of the active ingredient. Suitably the embeddable substance comprises greater than or equal to 1%, 2%, or 5% by weight of the active ingredient.

Suitably the embeddable substance comprises a gel forming agent, a suspension forming agent, an emulsion forming agent or a solution forming agent.

A suspension forming agent is a liquid that the active ingredient is poorly soluble in, for example the active ingredient has a solubility of less than 0.5 mg/mL, suitably less than 0.1 mg/mL, 0.05 mg/mL, or 0.01 mg/mL.

A solution forming agent it a liquid that the active ingredient is soluble in, for example, the active ingredient has a solubility of greater than or equal to 0.5 mg/mL, suitably greater than or equal to 1 mg/mL, 2 mg/mL, 5 mg/mL, 10 mg/mL, 50 mg/mL, or 100 mg/mL in the solution forming agent. Suitably, the active ingredient has a solubility of between 0.5 and 10 mg/mL in the solution forming agent.

An emulsion forming agent comprises two liquids wherein the two liquids are not miscible with each other. Suitably one liquid is a hydrophobic liquid and the other liquid is a hydrophilic liquid. Suitably, the hydrophobic liquid is a vegetable derived oil, for example soy bean oil. Suitably the hydrophilic liquid is an aqueous system, for example water.

Gel forming agents for use herein can be any gelling agent typically used in the pharmaceutical, neutraceutical or food supplement arts for oral delivery. As used herein, the term "gelling agent" is intended to mean a compound used to render a liquid vehicle into a jelly-like vehicle. Exemplary gelling agents include, by way of example and without limitation, synthetic macromolecules, cellulose derivatives (e.g. carboxymethylcellulose and hydroxypropylmethyl-cellulose) and natural gums (e.g. tragacanth, sodium alginate or xanthan gum). The synthetic macromolecules include carbomers (e.g. Carbomer 910, 934, 934P, 940, 941, and 1342), which are high molecular weight water-soluble polymers of acrylic acid cross-linked with allyl ethers of sucrose and/or pentaerythritol. Carbomers have different viscosities depending on their polymeric composition. Gelling agents of the present invention may be selected from any of synthetic or semi-synthetic polymeric materials, polyacrylate copolymers, cellulose derivatives and polymethyl vinyl ether/maleic anhydride copolymers. The present invention preferably uses natural gums. Suitably the gel forming agents are sodium alginate or xanthan gum.

Suitably the embeddable substance further comprises water. Suitably the embeddable substance further comprises an alkali. Suitably the alkali is sodium hydroxide.

Suitably the embeddable substance comprises sodium alginate, water and sodium hydroxide. Suitably the embeddable substance comprises 1-20% w/v of sodium alginate, suitably 2-15% w/v, 6-10% w/v, or about 8% w/v. Suitably the embeddable substance comprises 0.1-5% w/v, suitably 0.5-5% w/v, 1-3% w/v, or about 2% w/v.

Suitably the embeddable substance further comprises one or more other components. Other components may suitably include one or more excipients, excipients carriers, and/or diluents, all of which may be included in the embeddable substance.

Flavourants, preservatives, sweeteners, and colourants are known in the art of pharmaceuticals, nutraceuticals and food supplements, and any of these may be deployed where appropriate or desired for a particular pharmaceutical, nutraceutical or food supplement formulation.

Suitably the flavourants, preservatives, sweeteners, and colourants are substantially inert, and/or suitably have minimal or no interaction with other component(s) of the embedded item.

Suitable colourants may include curcumin, riboflavin, riboflavin-5'-phosphate, tartrazine, quinoline yellow, sunset yellow FCF, Cochineal, azorubine, amaranth, ponceau 4R, erythrosine, allura red AC, patent blue V, indigotine, brilliant blue FCF, chlorophylls, copper complexes of chlorophylls, green S, plain caramel, caustic sulphite caramel, ammonia caramel, sulphite ammonia caramel, brilliant black BN, vegetable carbon, brown HT, carotenes, annatto, paprika extract, lycopene, beta-apo-8'-carotenal, lutein, canthaxanthin, beetroot red, anthrocyanins, calcium carbonate, titanium dioxide, iron oxides and hydroxides, aluminium, silver, gold and/or litholrubine BK. The generic classes of excipients are well understood by those skilled in the art.

Suitably the embeddable substance is immiscible with the solidifiable body substance. Suitably, the embeddable substance is immiscible with the solidifiable body substance during the process to prepare the embedded item, suitably during the life time of the embedded item (for example until use by the end user, e.g., the patient), for example 1 hour, 1 day, 1 week, 1 month, 3 months, 6 months or greater than 6 months.

Embedding Apparatus to Prepare an Embedded Item

There is provided an embedding apparatus comprising an embedder and suitably also comprising a solidifiable body substance, suitably as defined herein, and/or an embeddable substance, suitably as defined herein. The embedding apparatus is suitably operable to form an embedded item via the method as described herein.

Suitably the embedding apparatus comprises an embeddable substance.

Suitably the embedding apparatus comprises a solidifiable body substance.

Suitably the embedding apparatus comprises a solidifiable body substance and an embeddable body substance.

Suitably the embedding apparatus comprises a mould. The mould may be a detachable or replaceable mould.

The embedding apparatus is suitable for embedding an embedding substance within a solidifiable body substance form an embedding solid item, wherein the embeddable substance and the embedded item comprises at least one active ingredient.

Embedder

The embedding apparatus suitably comprises an embedder. Suitably the embedder is a 3D-printer. Suitably the 3D-printer is an embedding 3D-printer. Embedding 3D-printers are known in the art and are generally suitable for use with the present invention, though they may be judiciously modified based on the principles outlined herein to optimise the preparation of the embedded item.

Embedders suitable for use with the invention generally have a deposition nozzle (optionally heated/heatable) with deposits the embeddable substance into (and within) the solidifiable body substance or onto a surface of a portion of the solidifiable body substance. Suitably the deposition nozzles may also deposit the solidifiable body substance onto the build platform or into a mould wherein the mould is on the build platform.

The embedder also suitably includes one or more deposition nozzle heaters (suitably one associated with each deposition nozzle but optionally one serving multiple deposition nozzles) and suitably one or more conveyors (suitably one associated with each deposition nozzle and/or each embeddable substance/solidifying body substance) as defined herein.

Suitably the embedder comprises a heated/heatable build platform. Suitably the solidifiable body substance is in contact with the build platform, either directly or indirectly through a mould. Suitably the mould is in direct contact with the build platform.

Suitably the embedder uses containers as herein defined. Suitably the embedding apparatus employs pre-filled container(s).

The embedding apparatus of the invention may comprise one or more other components, optionally embedding, printing or dispensing materials intended to form a part of the embedded item. For example, the embedded item may be coated with a coating.

Deposition Nozzle

Suitably, the embedding apparatus comprises at least one deposition nozzle through and from which an embeddable substance (or portion thereof) and/or a solidifying body substance (or part thereof) can be deposited from. Suitably the or each deposition nozzle may be a heated deposition nozzle, suitably a deposition heated nozzle with a variable temperature control (e.g. to allow the deposition nozzle to be selectively heated at a desired temperature). As such, the embedding apparatus may comprise a deposition nozzle heating element, suitably for heating the deposition nozzle to melt, soften, or otherwise liquidise the or part of the relevant substance. Suitably, the embedding apparatus may comprise a plurality of the aforementioned deposition nozzles, each of which may be assigned to one or more substances. Suitably such a deposition nozzle is a part of the embedder.

The temperature of the deposition nozzle(s) are suitably computer-controlled.

Suitably, the embedding apparatus comprises a conveyor for conveying the solidifying body substance(s) and/or embeddable substance(s) to and/or through the at least one deposition nozzle.

Suitably the conveyor feeds the solidifying body substance(s) and/or embeddable substance(s) through itself towards and/or through the relevant deposition nozzle. Suitably the conveyor is controlled to deliver the solidifying body substance(s) and/or embeddable substance(s) at a rate and/or at intervals suitable to provide the desired embedded item. The conveyor, or a part thereof (e.g. "a feeder") (preferably a part en route to the deposition nozzle) may be heated, suitably via a heating element associated therewith, optionally a separate and/or separately controllable heating element from any heating elements associated with the deposition nozzle. Where the embedding apparatus comprises more than one deposition nozzle, suitably the embedding apparatus comprises more than one feeder, one associated with each deposition nozzle.

The temperature of the deposition nozzle(s) are suitably computer-controlled. Suitably, the deposition nozzle(s) are configured to operate at temperatures between 0 and 350° C., suitably between 25 and 300° C., 80 and 300° C., 100 and 220° C., or 120 and 190° C.

Suitably each deposition nozzle comprises an input opening (into which the solidifying body substance(s) and/or embeddable substance(s) is fed) and an output opening (out of which the solidifying body substance(s) and/or embeddable substance(s) is deposited). The output opening is suitably smaller than the input opening. The output opening is suitably dimensioned for the properties of the solidifying body substance(s) and/or embeddable substance(s) to allow solidifying body substance(s) and/or embeddable substance(s) be deposited therefrom (e.g. onto a build platform/ within the solidifiable body substance).

Suitably the or each deposition nozzle may be movable (suitably in an automated fashion or in a manner controlled by a computer or by the embedder under instruction from the computer) to deposit the solidifying body substance(s) and/ or embeddable substance(s) at different locations upon the build platform or within the solidifiable body substance. The deposition nozzle may be moveable in any or all of the X, Y, and Z direction, though in some embodiments (e.g. where the build platform is movable in the Z direction, i.e. up and down relative to the deposition nozzle) it is constrained to move in only X and Y directions.

Suitably the or each deposition nozzle is operable to move at a speed of between 50 and 150 mm/min whilst depositing (i.e. when the deposition nozzle is "on"—this may be the deposition nozzle speed), suitably between 50 and 110 mm/min, suitably between 55 and 75 mm/min, suitably between 60 and 70 mm/min. Suitably the or each deposition nozzle is operable to move at a speed of between 100 and 200 mm/s when not depositing (i.e. when the deposition nozzle is "off"—this may be the deposition nozzle travelling speed), more suitably between 120 and 180 mm/s, more suitably between 140 and 160 mm/s.

It will be understood by those skilled in the art that the, each, or any deposition nozzle may be adapted to suit the properties of the solidifying body substance(s) and/or embeddable substance(s) configured to deposit thereto. The deposition nozzle properties/design, and solidifying body substance(s) and/or embeddable substance(s) properties suitably complement one another so as to facilitate controlled deposition of said substance(s) (be it continuous or intermittent, e.g. where more than one solidifying body substance(s) and/or embeddable substance(s) is used), suitably without any deposition nozzle blockages or impedance, and suitably without any unacceptable degradation of ingredients within the solidifying body substance(s) and/or embeddable substance(s) composition during the deposition process.

Build Platform

The embedding apparatus suitably comprises a build platform (or built plate) upon which the solidifying body substance(s) is depositing (directly or into a mould wherein the mould is in contact with the build platform). The build platform suitably provides a (substantially flat) surface that supports forming and formed embedded item throughout the process to form it.

Suitably a mould is provided on a surface of the build platform.

Suitably, during deposition of the solidifying substance the surface of the build platform or the mould onto which the embedded solid is to be deposited adheres to the embedded item (or at least to the layer thereof in contact with the build platform or mould) sufficiently to prevent movement of the developing item during deposition. Suitably, however, after deposition (e.g. optionally at a different temperature to the depositing operating temperature) the embedded item(s) may be removed from the build platform or mould without being damaged (e.g. the build platform or mould is non-adherent enough to allow the embedded item(s) to be removed or is selectively tunable, e.g. by changing the operating temperature, to allow the embedded item(s) to be removed therefrom). As such, the surface of the build platform or mould may comprise a surface coating or surface tape which imparts the required surface properties (e.g. adhesive but not too adhesive that the embedded items are permanently adhered).

The build platform (and mould if present) is suitably configured or operable to maintain a surface temperature (i.e. for the surface in contact with the embedded item) of less than or equal to 150° C., 100° C., 90° C., 80° C., 70° C., 60° C., 50° C., 40° C., or 30° C. Suitably The build platform (and mould if present) is suitably configured or operable to maintain a surface temperature (i.e. for the surface in contact with the embedded item) of greater than or equal to 5° C., 15° C., 30° C., or 40° C. The build platform (and mould if present) is suitably configured or operable to maintain a surface temperature (i.e. for the surface in contact with the embedded item) of 5-150° C. This may be achieved through selective operation of heating and/or cooling elements associated with (e.g. lying beneath) the surface of the build platform (and mould if present). In a particular embodiment, the build platform (and mould if present) is operable and preferably operated to maintain a surface temperature of between 20 and 110° C., suitably between 20 and 100° C., suitably about 40° C.

The build platform may be movable (suitably in an automated fashion or in a manner controlled by a computer or by the embedder under instruction from the computer) to control the position or height of the forming embedded item upon the build platform. The build platform may be moveable in any or all of the X, Y, and Z direction, though in some embodiments the build platform is movable in the Z direction only, i.e. up and down.

Dispensers

The embedding apparatus suitably comprises a dispenser. Suitably the dispenser comprises a storage container. The storage container suitably comprises the embeddable substance and/or the solidifying body substance or precursors thereof. The storage container is suitably sealed. The storage container may be in the form of a container (as defined herein, for example a cartridge or a syringe) specially adapted for compatibility with the apparatus of the invention. The storage container suitably has either an outlet (such as a valve-operated tap, optionally in conjunction with a positive dispensing means, such as a pressurizer or agitator) through and from which its contents may be dispensed, or a sampling port from which contents may be extracted by an external sampling element.

The dispenser suitably comprises one or more dispensing vessels. Suitably such dispensing vessels are configured to receive a quantity of the solidifying body substance and/or the embeddable substance (or precursors thereof) from the storage container, suitably either directly or via a conveying means. Suitably the one or more dispensing vessels may receive a pre-determined dose of the solidifying body substance and/or the embeddable substance (or precursors thereof).

The dispenser suitably comprises a quantifying component, for example, a gravimetric or volumetric component. Such a quantifying component suitably weighs or otherwise quantifies each dose of solidifying body substance and/or the embeddable substance (or precursors thereof) to be dispensed. Suitably the dispenser is operable to convey a quantity of the solidifying body substance and/or the embeddable substance (or precursors thereof) from the storage container to the quantifying component or to a dispensing vessel that interacts with the quantifying component. Suitably, one or more dispensing vessels are located so that quantifying component(s) can quantify the amount of the solidifying body substance and/or the embeddable substance received by the dispensing vessel(s). Alternatively, the quantifying component may be associated with the storage container and thereby measure a mass reduction as the extrudable composition (or precursor thereof) is dispensed therefrom. Quantification may be performed by weight and/or by volume.

The dispenser suitably comprises a flow-control component, which suitably controls and meters the distribution of the solidifying body substance and/or the embeddable substance (or precursors thereof) from the storage container to the one or more dispensing vessels. A flow-control component may, for example, comprise a controlled feed mechanism, and may suitably comprise an Archimedes screw, a valve, an agitator (e.g. to vibrate, tap, or shake). Alternatively or additionally, the flow-control component may comprise a sampling probe operable to sample a (estimated) quantity of the e solidifying body substance and/or the embeddable substance (or precursors thereof) from the storage container.

The dispenser suitably comprises an expelling mechanism for expelling quantified amounts of solidifying body substance and/or the embeddable substance (or precursor thereof) from either a sampling probe or dispensing vessel. Such an expelling mechanism may suitably comprise a release means (e.g. a tap, valve, vacuum release, or other such mechanism, for example, which may tip the contents out of a dispensing vessel towards a target dispensing point). Alternatively or additionally the expelling mechanism may comprise an expulsion means, for example, a pressurizer, agitator, screw, piston or plunger, which forces the solidifying body substance and/or the embeddable substance (or precursors thereof) from the dispensing vessel(s) to thereby dispense the solidifying body substance and/or the embeddable substance.

Suitably the components of the dispenser are computer-controlled, and suitably any valves or pressurizers are electronically controlled.

Computer Interface and Computer

The embedding apparatus, including the embedder (and optionally the build platform), is suitably operable via the computer, suitably a computer running pursuant to specialist software, and optionally also to one or more databases, optionally to deposit the solidifying body substance onto the build platform, to embed the embeddable substance within the solidifying body substance (either inject within, or print onto the surface of a portion of the solidifiable body substance), and thereby forming the embedded solid upon the build platform, suitably via a process involving the embedding of an embeddable substance within a solidifying body substance.

It will be readily understood by those skilled in the art that any one or more of the build platform, solidifying body substance(s), embeddable substance(s), and/or computer, and/or any part thereof, may suitably be integrated within or form a part of the embedder. In an embodiment, the embedding apparatus is essentially a 3D printer, suitably an embedding 3D-printer.

Suitably, the embedding apparatus comprises a computer interface (whether for wired or wireless connection to a computer operable to control the embedder).

The embedding apparatus suitably comprises a computer for controlling the embedder. The computer may optionally control the build platform (e.g. its position, height, etc.). The computer may thus be configured to operate the embedder (e.g. 3D-printer) pursuant to a pre-determined embedded item design pattern.

The embedder suitably includes or is otherwise connected to a computer. The embedder is suitably connected to the computer via an interface (suitably a digital interface), which may be wired (e.g. a port-to-port connection via an appropriate data lead, e.g. a USB lead) or wireless. The computer may be located at the site of the embedder (i.e. a local computer). However, the invention is equally applicable where the relevant computer (or computers) is located remote from the site of the relevant embedder, but both the embedder and remote computer comprise or are otherwise connected to respective communicators allowing the remote computer and embedder to communicate with one another. In this manner, a remote computer may be caused to operate the embedder. In a particular embodiment, the embedder may be connected to a network so that multiple remote computers (and/or local computers) may communicate therewith to cause the operation of the embedder.

The computer associated or otherwise connected with the embedder suitably controls deposition of the relevant embeddable substance(s) and/or solidifying body substance(s) in accordance with an embedded item design and/or embedded item parameters (e.g. relative amounts and juxtaposition of ingredients) set forth in a given embedded item data file (e.g. in a CAD or a .STL file), suitably as interpreted by relevant software pursuant to which the computer runs.

In a particular embodiment, the embedding apparatus comprises or is connected to a local computer, and both the embedding apparatus and the local computer are located on site at a pharmacy, most suitably in a purpose-build area or room (which may be suitably have regulatory approval).

Suitably the method and/or embedding apparatus involves a computer running pursuant to embedding software (and optionally one or more internal and/or external databases).

Suitably, a computer running pursuant to said to embedding software is configured to obtain information regarding one or more parameters (optionally including physical design parameters, such as shape) pertaining to the embedded item to be prepared (e.g. be it from information inputted manually by a user or information obtained automatically from another data source). Suitably the computer pursuant to said to embedding software is configured to request manual user input via a user interface (e.g. keyboard/screen) regarding one or more parameters pertaining to the embedded item to be prepared. For example, a user (which may be a pharmacist acting under instruction from a patient and/or doctor) may be requested to input information regarding patient name, patient reference number (e.g. healthcare number), and/or another reference name or number, following which the computer may communicate (via relevant communicators associated therewith) with one or more databases (be it local or remote, wired or wirelessly, e.g. via a network such as the internet) to automatically call further information and/or options corresponding with said name or reference (e.g. personal patient data, medication history, repeat prescriptions, data or partial data relating to the embedded item to be extruded, including embedded item data files containing designs and/or other relevant parameters). Thereafter, the user may be requested to manually input or manually select further information (e.g. drug, drug dose, release profile, etc.) and/or options to allow the computer to obtain all relevant information pertaining to the preparing of the embedded item form. Alternatively or additionally, the user may be requested to manually input or call information relating to one or more specific parameters pertaining to the embedded item (e.g. drug name/reference, drug dose, drug release requirements, colour, size, shape, solubility, packaging labelling information, etc.). Suitably, any user input may be logged and/or stored for future reference or for repeat prescriptions, etc.

There are a variety of ways the computer may be configured to obtain the relevant information to allow an embedded item to be prepared, but it is likely that a variety of pre-set information may be used (e.g. certain approved embeddable substance(s) and solidifiable body substance(s) combinations for producing a given embedded item). As such, the computer may suitably be associated with or connected/connectable with an embedded item database (suitably a central database accessible via a network, such as the internet) which provides all necessary pre-set information (e.g. data files relating to the embedded item and details of variable parameters such as drug dose levels/limits).

Suitably, an embedded item design (and optionally parameters connected therewith) may be recorded in an embedded item data file, which may be read by a computer running pursuant to the embedding software.

Suitably, a computer running pursuant to said to embedding software is configured to calculate the mass and/or volume of the embedded item to be prepared based on the information obtained. Suitably once the computer has obtained all required information (be it information manually inputted by a user, information imported automatically, or a combination of both) it is configured to perform calculations to allow finalisation of preparation instructions before the computer controls deposition of the embeddable substance and/or solidifiable body substance. At this stage, further input may be required or requested (e.g. via a user interface), for instance dimension(s) and/or shape modifications may be optionally selected. Calculations typically relate to the mass and/or volume of a given embedded item required to provide a given active dosage per embedded item. Though it may be possible to increase the concentration of a given active ingredient relative to other ingredients (e.g. excipients), typically formulations are optimised and relative proportions fixed/pre-set, whereas overall mass/volume may be varied whilst retaining the same relative proportions of ingredients.

Suitably, a computer running pursuant to said embedding software is configured to control deposition of and relative proportions of ingredients within the embedding solid item, suitably based on the information obtained and suitably based on the calculations performed. Suitably "controlling deposition" includes initiating deposition of the solidifiable body substance and/or the embeddable substance and terminating deposition and any or all operations therebetween.

Suitably during deposition, operational data is collected (optionally by one or more local and/or remote computers and/or databases) and suitably stored (most suitably at a central computer which may analyse such data, e.g. for quality control monitoring, monitoring of malfunctions, monitoring of batches, monitoring of dosage forms dispensed to a given patient, etc.). Suitably the embedding apparatus comprises or is otherwise associated with one or more operational sensors (e.g. deposition nozzle temperature sensors, feed rate sensors or conveyor sensors for the embeddable substance and/or the solidifiable body substance, overall temperature sensors, build platform sensors which may, for example, monitor surface temperature and/or rate of cooling/heating of the build platform (and mould if present), etc.) which feedback operational parameters/information to a computer, database, or data storage facility, relating to the operation of the embedding apparatus and elements associated therewith during the preparation of each embedded item. Most preferably, such operational data is collected, stored, and/or otherwise transmitted to a central computer or database to enable independent auditing of any given embedding apparatus. This may be important in order to maintain quality control, and maintain appropriate records in order to retain regulatory approval of any given system.

Suitably, a computer running pursuant to said to embedding software is configured to control performance of one or more further processing steps.

Software and Data Files

The computer operating the embedding apparatus suitably runs pursuant to embedding software (and optionally also to one or more databases). As explained herein, this software may configure the computer to obtain information and perform calculations before it then configures the computer to control deposition via an interface with the embedding apparatus.

Once the computer has obtained the relevant information and performed the relevant calculation, suitably the software configures the computer to control deposition of the embeddable substance and/or solidifiable body substance thereby forming the embedded item, suitably based on a design (shape and dimensions, texture, layer structure, internal structure, porosity, colour(s), etc.) and/or parameters (relative amounts of ingredients, such as drug dose) relating to said embedded item contained within one or more embedded item data files. The embedded item data files may include a design file (e.g. containing data and/or images relating to the physical design of the embedded item, including its dimensions, shape, layered structure, core-shell structure, etc.) and/or a parameter file (e.g. containing data relating to the chemical composition of the embedded item, including drug type, excipient type(s), drug dose level, excipients to control drug release, etc.). A single embedded item data file may contain all data pertaining to the physical design and chemical composition. However, the physical design and chemical composition may be modified pursuant to information obtained following user input.

In some embodiments, the design file may be a CAD file depicting an embedded item. However, such file formats are likely to require conversion to a file format compatible with the embedding apparatus. In particular, 3D printers generally read design files in a .STL format. As such, the design file is suitably a .STL design file depicting the embedded item (or at least the physical design thereof).

The design file may include or be linked with a parameter file containing chemical composition details, or the two may be independent. Alternatively there may be no parameter file as such and instead the relevant parameter information may be called from a database, for instance, in response to user input (e.g. patient reference, or drug reference, etc.).

The software may additionally configure the computer to collect, store, and/or transmit (e.g. to a central database) operational data fed back to the computer from the embedding apparatus (e.g. 3D printer) during preparation of the embedded item. The software may configure the computer to detect and/or respond to any (or a preset level of) deviation in expected operational data (e.g. if build platform temperature exceeds a maximum preset temperature level), for instance alerting the user/operator or any other interested party that a malfunction has occurred and that the embedded item produced during malfunctional should be disposed or otherwise tested.

Databases

The embedding apparatus and/or computer(s) associated therewith may be configured (e.g. by the embedding software) to communicate with (suitably via relevant communicator(s), and suitably via a network such as the internet) one or more embedded item databases and/or patient databases to obtain information regarding one or more parameters pertaining to the embedded item to be prepared. For example, such database(s) may be consulted in response to a user input (e.g. patient reference number) to furnish the computer with the relevant information (or relevant information to be supplemented by further user input) to enable calculations and deposition of the embeddable substance and/or solidifiable body substance to be performed.

By way of example, a patient database comprising patient records for multiple patients (which records may include, for example, patient name, patient reference number, medical data, medical history, etc.) suitably contains information (which may merely be a cross-reference or reference number relating to information residing in another database, such as an embedded item database) regarding the embedded item to be prepared for each patient. Where the "information" is a cross-reference to an embedded item database, this embedded item database may then be consulted for further information regarding the embedded item. This information may be any of the information defined herein, though optionally the embedding apparatus or computer(s) associate therewith may be instructed (e.g. via a user interface) to modify the information (e.g. drug dose level) prior to calculations and/or deposition. Any of these databases may be accessible to interested parties, preferably securely accessible (to maintain confidentiality of certain data), to enable the relevant information (be it in a patient database, embedded item database, or both) to be retrieved and/or amended as required (e.g. if a patient needs an increased dose in the embedded items or a different active release profile). Suitably such database(s) may be wirelessly accessible via a network, such as the internet. Such database architectures are well known in the art.

The or each embedding apparatus and/or computer(s) associated therewith may be configured (e.g. by the embedding software) to communicate with (suitably via relevant communicator(s), and suitably via a network such as the internet) one or more embedding apparatus-monitoring databases configured to transmit to and store within said database (and optionally analyse and/or report upon) operational data collected (optionally by one or more local and/or remote computers and/or databases) during each operation (i.e. each time the apparatus deposits a substance). As described herein, such operational data is suitably obtained/delivered by sensors associated with each given embedding apparatus, suitably sensors associated with key parts of the embedding apparatus that could affect the quality of the ultimate embedded item. The operational data may be transmitted to said database in real time, following preparation of the embedded item, or at any suitable time (e.g. at night to avoid unnecessary overloading communication networks during work hours). Such embedding apparatus-monitoring databases may be organised with a record for each embedding apparatus, and may suitably maintain a log of operational data each time said embedding apparatus is operated. Suitably each set of operational data is cross-reference to a given patient an embedded item, suitably so that if any operational data is deemed malfunctional, the relevant interested parties can be alerted. In this manner, each embedding apparatus may be monitored (whether in real time or otherwise, whether automatically or otherwise) and data periodically submitted to satisfy regulatory requirements. Moreover, central embedding apparatus-monitoring databases may trigger a response to any perceived malfunction of a given embedding apparatus. Moreover, a response may be triggered which prevents the relevant malfunctional embedding apparatus from being used until its performance can be revalidated.

Again, any of the one or more embedding apparatus-monitoring databases may be accessible to interested parties, preferably securely accessible (to maintain confidentiality of certain data), to enable the relevant information to be retrieved and/or analysed as required (e.g. if regulatory bodies wish to check that a given embedding apparatus has been in good order throughout a given period, or if machine maintenance professionals which to use the data to diagnose a problem in order to restore the performance of a given embedding apparatus). Suitably such database(s) may be wirelessly accessible via a network, such as the internet. Such database architectures are well known in the art.

Applications of Embedded item

The embedded item of the invention may take a variety of forms, though most suitably the embedded item is a solid dosage form, most suitably, the solid dosage form of a pharmaceutical, a nutraceutical and/or a food supplement solid dosage form.

In a particular embodiment, the embedded item is a pharmaceutical solid dosage form.

In a particular embodiment, the embedded item is an embedded item for use in the manufacture of a medicament. Suitably the embedded item is an embedded item for use in therapy.

The present invention also provides a method of treating and/or preventing a disease, condition, or disorder in a subject in need of such treatment. The method suitably comprises administering a therapeutically effective amount of the embedded item to the subject. Suitable the subject is an animal or human subject, most suitably a human subject. Suitably, there is provided an embedded item for use as a medicament.

Suitably, the embedded item is an immediate release pharmaceutical solid dosage form for oral administration.

Packing of Solidifiable Body Substance(s) and Embeddable Substances

Solidifiable body substances(s) and/or embeddable substance(s) of the invention may be packaged by any one of a number of methods well known in the art. For example, cartridges for use in embedding apparatus can be preloaded with the solidifiable body substance(s) and/or embeddable substance(s). Advantageously, the cartridges can be prepared at a different site to where the embedding apparatus is situated and can be inserted into the embedding apparatus as and when required. Thus, when the embedding apparatus is located at different site, the user of the embedding apparatus, for example a pharmacist, can select the appropriate solidifiable body substance package(s), embeddable substance package(s) and/or a solidifiable body substance and embeddable substance package(s), insert said package(s) into the embedding apparatus, and use the package(s) to prepare an embedded item using said solidifiable body substance and/or embeddable substance.

Suitably there is provided a solidifiable body substance package comprising a container filled with the solidifiable body substance.

Suitably there is provided an embeddable substance package comprising a container filled with the embeddable substance.

Suitably there is provided a solidifiable body substance and embeddable substance package comprising a container filled with the solidifiable body substance and the embeddable substance.

Suitably the container is adapted to fit into the embedding apparatus, suitably so the contents of the container (e.g. the embeddable substance and/or solidifiable body substance) can be conveyed through the embedding apparatus. In one embodiment, the container is adapted so the contents of the container (e.g. the embeddable substance and/or solidifiable body substance) can be conveyed to the deposition nozzles of the embedding apparatus.

In one embodiment, the container comprises deposition nozzles.

Suitably, the container is a cartridge, suitably a printer cartridge, suitably an embedding apparatus cartridge, such as a 3D printer cartridge. Suitably the container contains the embeddable substance wherein the embeddable substance is in the form of a gel.

Suitably there is provided an embeddable substance package, comprising one or more embeddable substances, as defined herein, wherein the one or more embeddable substances are optionally the same or different, within a packaging.

Suitably there is provided a solidifiable body substance package, comprising one or more solidifiable body substances, as defined herein, wherein the one or more solidifiable body substances are optionally the same or different, within a packaging.

Suitably there is provided a method of producing an embeddable substance package, the method comprising packaging one or more embeddable substance as defined herein, wherein the one or more embeddable substance are optionally the same or different.

Suitably there is provided a method of producing a solidifiable body substance package, the method comprising packaging one or more solidifiable body substance as defined herein, wherein the one or more solidifiable body substance are optionally the same or different.

Suitably there is provided an embeddable substance package, obtainable by, obtained by, or directly obtained by the method of producing an embeddable substance package as defined herein.

Suitably there is provided a solidifiable body substance package, obtainable by, obtained by, or directly obtained by the method of producing a solidifiable body substance package as defined herein.

Packaging of Embedded Item(s)

Embedded item(s) of the invention may be packaged by any one of a number of methods well known in the art. Where, for example, pharmaceutical solid dosage forms according to the invention are produced via an embedding apparatus situated in a pharmacy (e.g. to provide a patient with customised medicaments on-demand), the pharmacist may package the embedded item (e.g. solid dosage form) in a number of ways, including in tablet bottles, or even monitored dosing systems which may be subsequently dispatched to hospitals, care homes, and the like for ultimate dispensation to a patient.

Suitably there is provided a method of producing an embedded item package, the method comprising packaging one or more embedded items as defined herein, wherein the one or more embedded items are optionally the same or different.

Suitably there is provided an embedded item package, obtainable by, obtained by, or directly obtained by the method of producing an embedded item package as defined herein.

Suitably there is provided an embedded item package, comprising one or more embedded items, as defined herein, wherein the one or more embedded items are optionally the same or different, within a packaging.

Specific Embodiments of Embedded Item

There is provided an embedded item comprising an embeddable substance within a solidifiable body substance.

Suitably there is provided an embedded item comprising an embeddable substance within a solidifiable body substance wherein the embedded item comprises 0.01 to 50% by weight of at least one active ingredient.

Suitably there is provided an embedded item comprising 0.1 to 90% by weight of an embeddable substance within a solidifiable body substance.

Suitably there is provided an embedded item comprising an embeddable substance within a solidifiable body substance wherein the embeddable substance comprises at least one active ingredient.

Suitably there is provided an embedded item comprising an embeddable substance within a solidifiable body substance wherein the embeddable substance comprises 0.01 to 50% weight of at least one active ingredient.

Suitably there is provided an embedded item comprising an embeddable substance within a solidifiable body substance; wherein the embeddable substance comprises at least one active ingredient; and wherein the embedded item is a pharmaceutical, a nutraceutical or a food supplement solid dosage form.

Suitably there is provided an embedded item comprising an embeddable substance within a solidifiable body substance; wherein the embeddable substance comprises at least one active ingredient; wherein the embedded item is a pharmaceutical, a nutraceutical or a food supplement oral solid dosage form; and wherein the oral solid dosage form is a chewable tablet.

Suitably there is provided an embedded item comprising an embeddable substance within a solidifiable body substance; wherein the embeddable substance comprises at least one active ingredient; and wherein the embeddable substance present as a single layer within the solidifiable body substance.

Suitably there is provided an embedded item comprising an embeddable substance within a solidifiable body substance; wherein the embeddable substance comprises at least one active ingredient; and wherein the embeddable substance present as at least two layers within the solidifiable body substance.

Suitably there is provided an embedded item comprising an embeddable substance within a solidifiable body substance; wherein the embeddable substance comprises at least one active ingredient; and wherein the embeddable substance present as a continuous layer within the solidifiable body substance.

Suitably there is provided an embedded item comprising an embeddable substance within a solidifiable body substance' wherein the embeddable substance comprises at least one active ingredient; wherein the embeddable substance present as a continuous layer within the solidifiable body substance; and wherein the embeddable substance is present as a continuous line with the layer.

Suitably there is provided an embedded item comprising an embeddable substance within a solidifiable body substance; wherein the embeddable substance comprises at least one active ingredient; and wherein the embeddable substance present as a line in a layer within the solidifiable body substance.

Suitably there is provided an embedded item comprising an embeddable substance within a solidifiable body substance; wherein the embeddable substance comprises at least one active ingredient; and wherein the embeddable substance is a solution, a semi-solid, an emulsion, or a suspension.

Suitably there is provided an embedded item comprising an embeddable substance within a solidifiable body substance; wherein the embeddable substance comprises at least one active ingredient; and wherein the embeddable substance is a solution, a gel, an emulsion, or a suspension.

Suitably there is provided an embedded item comprising an embeddable substance within a solidifiable body substance; wherein the embeddable substance comprises at least one active ingredient; and wherein the embeddable substance is a gel.

Suitably there is provided an embedded item comprising an embeddable substance within a solidifiable body substance; wherein the embeddable substance comprises at least one active ingredient; and wherein the embeddable substance is a gel comprising xanthan gum and/or sodium alginate.

Suitably there is provided an embedded item comprising an embeddable substance within a solidifiable body substance; wherein the embeddable substance comprises at least one active ingredient; and wherein the embeddable substance is a gel comprising xanthan gum, sodium alginate, water and/or an alkali.

Suitably there is provided an embedded item comprising an embeddable substance within a solidifiable body substance; wherein the embeddable substance comprises at least one active ingredient; and wherein the solidifiable body substance comprises a gelatine matrix.

Suitably there is provided an embedded item comprising an embeddable substance within a solidifiable body substance; wherein the embeddable substance comprises at least one active ingredient; wherein the solidifiable body substance comprises a gelatine matrix; and wherein the embeddable substance is a gel.

Suitably there is provided an embedded item comprising an embeddable substance within a solidifiable body substance; wherein the embeddable substance comprises at least one active ingredient; wherein the solidifiable body substance comprises a gelatine matrix; and wherein the embeddable substance is a gel comprising xanthan gum and/or sodium alginate.

Suitably there is provided a method of preparing an embedded item, the method comprising:
  i. Providing a solidifiable body substance in a fluid or a semi-fluid form;
  ii. Embedding within the solidifiable body substance an embeddable substance;
  iii. Solidifying the solidifiable body substance with the embeddable substance therein.

Suitably there is provided a method of preparing an embedded item, the method comprising:
  i. Providing a solidifiable body substance in a fluid or a semi-fluid form;
  ii. Embedding within the solidifiable body substance an embeddable substance wherein the embeddable substance comprises at least one active ingredient;
  iii. Solidifying the solidifiable body substance with the embeddable substance therein.

Suitably there is provided a method of preparing an embedded item, the method comprising:
  i. Providing a solidifiable body substance in a fluid or a semi-fluid form by filling a mould with the solidifiable body substance;
  ii. Embedding within the solidifiable body substance an embeddable substance;
  iii. Solidifying the solidifiable body substance with the embeddable substance therein.

Suitably there is provided a method of preparing an embedded item, the method comprising:
  i. Providing a solidifiable body substance in a fluid or a semi-fluid form by filling a mould with the solidifiable body substance at a temperature greater than ambient temperature;
  ii. Embedding within the solidifiable body substance an embeddable substance;
  iii. Solidifying the solidifiable body substance with the embeddable substance therein.

Suitably there is provided a method of preparing an embedded item, the method comprising:
  i. Providing a solidifiable body substance in a fluid or a semi-fluid form;
  ii. Embedding within the solidifiable body substance an embeddable substance;
  iii. Solidifying the solidifiable body substance with the embeddable substance therein by UV curing, heating, cooling and/or providing a cross-linking agent.

Suitably there is provided a method of preparing an embedded item, the method comprising:
  i. Providing a solidifiable body substance in a fluid or a semi-fluid form by filling a mould with the solidifiable body substance;
  ii. Embedding within the solidifiable body substance an embeddable substance;
  iii. Solidifying the solidifiable body substance with the embeddable substance therein by UV curing, heating, cooling and/or providing a cross-linking agent.

Suitably there is provided a method of preparing an embedded item, the method comprising:
i. Providing a solidifiable body substance in a fluid or a semi-fluid form by filling a mould with the solidifiable body substance at a temperature greater than ambient temperature;
ii. Embedding within the solidifiable body substance an embeddable substance;
iii. Solidifying the solidifiable body substance with the embeddable substance therein by UV curing, heating, cooling and/or providing a cross-linking agent.

Suitably there is provided a method of preparing an embedded item, the method comprising:
i. Providing a solidifiable body substance in a fluid or a semi-fluid form by filling a mould with the solidifiable body substance at a temperature greater than ambient temperature;
ii. Embedding within the solidifiable body substance an embeddable substance;
iii. Solidifying the solidifiable body substance with the embeddable substance therein by cooling.

Suitably there is provided a method of preparing an embedded item, the method comprising:
i. Providing a solidifiable body substance in a fluid or a semi-fluid form by filling a mould with the solidifiable body substance at a temperature greater than ambient temperature;
ii. Embedding within the solidifiable body substance an embeddable substance;
iii. Solidifying the solidifiable body substance with the embeddable substance therein by cooling to ambient temperature.

Suitably there is provided a method of preparing an embedded item, the method comprising:
i. Providing a solidifiable body substance in a fluid or a semi-fluid form;
ii. Embedding within the solidifiable body substance an embeddable substance using a printer;
iii. Solidifying the solidifiable body substance with the embeddable substance therein.

Suitably there is provided a method of preparing an embedded item, the method comprising:
i. Providing a solidifiable body substance in a fluid or a semi-fluid form;
ii. Embedding within the solidifiable body substance an embeddable substance wherein the embeddable substance is in a layer within the solidifiable body substance;
iii. Solidifying the solidifiable body substance with the embeddable substance therein.

Suitably there is provided a method of preparing an embedded item, the method comprising:
i. Providing a solidifiable body substance in a fluid or a semi-fluid form;
ii. Embedding within the solidifiable body substance an embeddable substance wherein the embeddable substance comprises at least one active ingredient and wherein the embeddable substance is in a layer within the solidifiable body substance;
iii. Solidifying the solidifiable body substance with the embeddable substance therein.

Suitably there is provided a method of preparing an embedded item, the method comprising:
i. Providing a solidifiable body substance in a fluid or a semi-fluid form by filling a mould with the solidifiable body substance;
ii. Embedding within the solidifiable body substance an embeddable substance wherein the embeddable substance comprises at least one active ingredient and wherein the embeddable substance is in a layer within the solidifiable body substance;
iii. Solidifying the solidifiable body substance with the embeddable substance therein by UV curing, heating, cooling and/or providing a cross-linking agent.

Suitably there is provided a method of preparing an embedded item, the method comprising:
i. Providing a solidifiable body substance in a fluid or a semi-fluid form by filling a mould with the solidifiable body substance;
ii. Embedding within the solidifiable body substance an embeddable substance using a printer wherein the embeddable substance comprises at least one active ingredient and wherein the embeddable substance is in a layer within the solidifiable body substance;
iii. Solidifying the solidifiable body substance with the embeddable substance therein by UV curing, heating, cooling and/or providing a cross-linking agent.

Suitably there is provided an embedding apparatus comprising an embedder, a solidifiable body substance, suitably as defined herein, and/or an embeddable substance, suitably as defined herein.

Suitably there is provided an embedding apparatus comprising an embedder, a solidifiable body substance, suitably as defined herein, and an embeddable substance, suitably as defined herein.

Suitably there is provided an embedding apparatus comprising an embedder and a solidifiable body substance, and an embeddable substance; wherein the embeddable substance comprises at least one active ingredient.

Suitably there is provided an embedding apparatus comprising an embedder, a solidifiable body substance, and an embeddable substance; wherein the embeddable substance comprises at least one active ingredient and wherein the embedder is a printer.

Suitably there is provided an embedding apparatus comprising an embedder, a solidifiable body substance, and an embeddable substance; wherein the embeddable substance comprises at least one active ingredient; and wherein the embedder is a printer comprising a build platform.

Suitably there is provided an embedding apparatus comprising an embedder, a solidifiable body substance, and an embeddable substance; wherein the embeddable substance comprises at least one active ingredient; and wherein the embedder is a printer comprising a build platform is configured or operable to maintain a surface temperature of less than or equal to 150° C.

Suitably there is provided an embedding apparatus comprising an embedder, a solidifiable body substance, and an embeddable substance; wherein the embeddable substance comprises at least one active ingredient; wherein the embedder is a printer comprising a build platform; and wherein there is a mould provided on a surface of the build platform.

Suitably there is provided an embedding apparatus comprising an embedder, a solidifiable body substance, and an embeddable substance; wherein the embeddable substance comprises at least one active ingredient; and wherein the embedder is a printer wherein the printer comprises deposition nozzles.

Suitably there is provided an embedding apparatus comprising an embedder, a solidifiable body substance, and an embeddable substance; wherein the embeddable substance comprises at least one active ingredient; and wherein the embedder is a printer wherein the printer comprises deposition nozzles and a build platform.

Suitably there is provided an embedding apparatus comprising an embedder, a solidifiable body substance, and an embeddable substance; wherein the embeddable substance comprises at least one active ingredient; wherein the embedder is a printer; and wherein the printer comprises deposition nozzles, a build platform and a dispenser.

Suitably there is provided an embedding apparatus comprising an embedder, a solidifiable body substance, and an embeddable substance; wherein the embeddable substance comprises at least one active ingredient; and wherein the embedder is a printer wherein the printer comprises deposition nozzles, a build platform, a dispenser and a computer interface.

Suitably there is provided an embedding apparatus comprising an embedder, a solidifiable body substance, and an embeddable substance; wherein the embeddable substance comprises at least one active ingredient; and wherein the embedder is a printer wherein the printer comprises deposition nozzles, a build platform, a dispenser and a computer for controlling the embedder.

EXAMPLES

Lisinopril dihydrate, indapamide, amlodipine besylate and rosuvastatin calcium were purchased from Kemprotec Ltd (Cumbria, UK). Theophylline (anhydrous, 99+%) was purchased from ACROS Organics (Germany). Titanium dioxide was obtained from Sigma-Aldrich, Inc. (Gillingham, UK). HPLC gradient grade acetonitrile and methanol were from Fisher Scientific Ltd (Loughborough, UK). Poly(vinyl alcohol) Parteck MXP is a polymer developed for hot melt extrusion which is also Generally Recognised as Safe (GRAS) by the US Food and Drug Administration and compliant with the US, European and Japanese pharmacopeias for excipients monographs. All other materials were of analytical grade and commercially available.

Example 1: Optimisation of the Composition of and Conditions to Prepare an Extrudable Element In this example a series of filaments were prepared. The ratio of PVA (an extrudable carrier) to a sorbitol (a permanent plasticiser) and water (a temporary plasticiser) were optimised for use of the filament in a fused deposition modelling (FDM) 3D printer head.

A Thermo Scientific HAAKE MiniCTW hot melt extruder (Karlsruhe, Germany) was used to prepare the filaments. The extruded filaments were dried at 100° C. at 0% RH for 1 hour in a FD240 Binder heating chamber (Tuttlingen, Germany).

A Makerbot 2×3D printer (Makerbot Industries, NY, USA) fitted with 0.4 mm nozzle and controlled by Simplify 3D software version 4.0 (Cincinnati, OH, USA). Printing took place using. The tablets were printed following a concentric fill pattern and 100% infill with a layer thickness of 166 μm.

Stage 1: Varying the PVA: Sorbitol Ratio; Presence of Non-Melting Components
Preparation 1:
Composition: 50% w/w PVA (Parteck® SI 200 by Merck) and 50% w/w sorbitol
Hot Melt Extrusion (HME) parameters: Extrusion temperature of 150° C.; extrusion mixing speed 120 rpm; extrusion speed 35 rpm; 1.5 mm nozzle.

Results: The filament was too flexible for us in a FDM 3D printer head. The gears of the 3D printer could not pass it down to the nozzle.
Preparation 2:
Composition: 67% w/w PVA (Parteck® SI 200 by Merck) and 33% w/w sorbitol
HME parameters: Extrusion temperature of 170° C.; extrusion mixing speed 120 rpm; extrusion speed 35 rpm; 1.5 mm nozzle.
Results: The filament was less flexible than the filament from Preparation 1 but was still too flexible for use in a FDM 3D printer head.
Preparation 3:
Composition: 50% w/w Theophylline, 35% w/w PVA (Parteck® SI 200 by Merck) and 15% w/w sorbitol.
HME parameters: Extrusion temperature of 180° C.; extrusion mixing speed 90 rpm; extrusion speed 35 rpm; 1.7 mm nozzle.
Results: The theophylline does not melt during extrusion to form the filament (non-melting component). The resulting filament has appropriate flexibility for 3D printing as could be fed to the FDM 3D printer. The filament could be printed at a temperature of 210° C. This temperature may be too high for thermally sensitive active ingredients. In general, it was found that the presence of non-melting components reduced the flexibility of the filament and in addition increased the resistance to flow resulting in a higher extrusion temperature being required.
Conclusion: These experiments demonstrated that varying the ratio of PVA to sorbitol did not significantly reduce the extrusion temperature required and that the presence of a non-melting component the extrusion temperature required was increased. The extrusion temperatures required to extrude the compositions of preparations 1, 2 and 3 were at least 150° C. This may be too high if thermally sensitive ingredients are present. Alternative ways of reducing the extrusion temperature were investigated.
Stage 2: Optimisation of the Amount of Water (Temporary Plasticiser)
Preparation 4:
Composition: 66.5% w/w PVA, 28.5% w/w Sorbitol and 5% w/w distilled non-ionised water
HME parameters: Extrusion temperature of 90° C.; extrusion mixing speed of 90 rpm; extrusion speed 35 rpm; 1.7 mm nozzle.
Results: A flexible filament was obtained. The flexibility was lost after drying the filament in the oven (70° C., 2 hour). The filament became very brittle and was not suitable for 3D printing.
Preparation 5:
Composition: 63% w/w PVA, 27% w/w Sorbitol and 10% w/w distilled non-ionised water
HME parameters: Extrusion temperature of 90° C.; extrusion mixing speed 90 rpm; extrusion speed 35 rpm; 1.7 mm nozzle.
Results: A flexible, white filament was obtained. The flexibility remained even after drying the filament in an oven (70° C., 2 hours) which made it possible to feed the filament into the FDM 3D printer and print the filament at a printing temperature was 150° C.
Preparation 6:
56% w/w PVA, 24% w/w Sorbitol and 20% w/w distilled non-ionised water.
HME parameters: Extrusion temperature of 80° C.; extrusion mixing speed of 90 rpm; extrusion speed 35 rpm; 1.7 mm nozzle.

Results: A flexible, white filament with appropriate flexibility after drying (70° C., 2 hours) was obtained.

Conclusion: These experiments demonstrated that it is possible to reduce the extrusion temperature through the use of a temporary plasticiser. The temporary plasticiser can subsequently be partially removed post extrusion to yield a filament which has suitable flexibility for use in a 3D printer.

Stage 3: Optimisation of the Drying Time of the Filament after Extrusion

Part 1:

Two filaments were prepared as detailed below (Preparations 7 and 8).

Preparation 7:

Composition: 66.5% w/w PVA, 28.5% w/w Sorbitol and 5% w/w distilled non-ionised water HME parameters: Extrusion temperature of 150° C.; extrusion mixing speed 90 rpm; extrusion speed 35 rpm; 1.7 mm nozzle.

Preparation 8:

Composition: 63% w/w PVA, 27% w/w Sorbitol and 10% w/w distilled non-ionised water HME parameters: Extrusion temperature of 120° C.; extrusion mixing speed 90 rpm; extrusion speed 35 rpm; 1.7 mm nozzle.

Portions of these filaments (Preparations 7 and 8) were weighed and dried in the oven for 2 hours 15 minutes at 50° C. The filaments were weighed after 1 hour, 2 hours, and 2 hours and 15 minutes in the oven in order to assess the weight loss.

Results:

Preparation 7:

| Time point | Initial | 1 hour | 2 hours | 2 hours 15 minutes |
| --- | --- | --- | --- | --- |
| Weight (g) | 1.4061 | 1.3607 | 1.3507 | 1.3511 |
| % weight loss | — | 3.23 | 3.94 | 3.91 |

Preparation 8:

| Time point | Initial | 1 hour | 2 hours | 2 hours 15 minutes |
| --- | --- | --- | --- | --- |
| Weight (g) | 1.6597 | 1.5812 | 1.5693 | 1.5672 |
| % weight loss | — | 4.73 | 5.45 | 5.57 |

Part 2:

A second drying experiment was performed using an oven temperature of 70° C. using preparation 9.

Preparation 9:

Composition: 100:20 ration of dry ingredients: distilled non-ionised water. Dry ingredients composition is 50% w/w Theophylline, 35% w/w PVA, 15% w/w Sorbitol.

The filament was split into two portions, 9a and 9b, and dried for 1 and 2 hours respectively.

Results:

Portion 9a:

| Portion 9a | Initial Weight | Final Weight (after drying for 1 hour at 70° C.) |
| --- | --- | --- |
| Weight (g) | 1.2237 | 1.091 |
| % weight loss | — | 10.84 |

Portion 9b:

| Portion 9b | Initial Weight | Final Weight (after drying for 2 hours at 70° C.) |
| --- | --- | --- |
| Weight (g) | 1.3421 | 1.1931 |
| % weight loss | — | 11.10 |

Filament portion 9a post drying had suitable flexibility for use in 3D-printing.

Conclusion: An optimized ratio of solid to water content of 100:20 for the PVA, sorbitol, theophylline and water composition was reached to allow extrusion at relatively low temperature. A dying time and temperature was optimised to reach a residual water content of 4% and a $T_g$ of −10° C.

Example 2: Preparation of a PVA Containing Filament and Tablet Loaded with Theophylline and Hydrocortisone Methods:

Preparation of the Filaments Using Hot Melt Extrusion (HME)

Filaments containing individual drugs at different concentration were produced to achieve the individual target dose of each model drug. A Thermo Scientific HAAKE MiniCTW hot melt extruder (Karlsruhe, Germany) was used to prepare the filaments. Blank (drug-free) and individual drug loaded filaments were prepared by blending 10 g of dry ingredients (composition according to Table I) with additional 2 g of distilled water (temporary plasticiser) (Table 1) using mortar and pestle. This blend mixture was then fed to the hot melt extruder at 90° C. and mixed at 100 rpm, nozzle size of 1.5 mm. The filaments were extruded at the same temperature at 35 rpm. The extruded filaments were dried at 100° C. at 0% RH for 1 hour in a FD240 Binder heating chamber (Tuttlingen, Germany). For comparison purposes, a filament was also extruded without water at an extrusion temperature of 180° C. and a mixing rate of 100 rpm.

TABLE I

Ingredients of HME based filament containing theophylline and hydrocortisone (thermo-sensitive drug).

| | Ingredients | | | | | | |
| --- | --- | --- | --- | --- | --- | --- | --- |
| Filament | Theophylline | hydrocortisone | PVA | Sorbitol | TiO$_2$ | Tri calcium phosphate | Nozzle size |
| Blank filament (drug free) | | | 70% | 30% | 1 | — | 1.7 |
| Theophylline filament | 50 | — | 35 | 15 | — | — | 1.5 |

TABLE I-continued

Ingredients of HME based filament containing theophylline and hydrocortisone (thermo-sensitive drug).

| Filament | Theophylline | hydrocortisone | PVA | Sorbitol | TiO$_2$ | Tri calcium phosphate | Nozzle size |
|---|---|---|---|---|---|---|---|
| Hydrocortisone filament | — | 1 | 35 | 15 | 1 | 48 | 1.5 |

Tablet Design and 3D Printing

The tablets printed were designed using Autodesk® 3ds Max Design 2016 software version 18.0 (Autodesk, Inc., USA). The designs were then imported to the computer software in stereolithographic (STL) format. The extruded filaments were printed by a Makerbot 2×3D printer (Makerbot Industries, NY, USA) fitted with 0.4 mm nozzle and controlled by Simplify 3D software version 4.0 (Cincinnati, OH, USA). Printing took place using nozzle and building plate temperatures of 150 and 40° C. respectively. The tablets were printed following a concentric fill pattern and 100% infill with a layer thickness of 166 μm. For comparison reasons, tablets (without addition of water) were printed following the same settings as above but at nozzle temperature of 210° C.

Thermal Analysis

Samples of the raw materials, drug-loaded filaments and 3D printed tablets were analysed by differential scanning calorimetry (DSC) and thermogravimetric analysis (TGA). TGA Q500 (TA Instruments, Elstree, Hertfordshire, UK) was used to analyse of about 10 mg of each material. Samples were heated at a rate of 10° C./min from 25° C. to 500° C. with a nitrogen purge of 40 ml/min for the sample and 60 ml/min for the furnace respectively. In addition, DSC Q2000 (TA Instruments, Elstree, UK) was used to assess the thermal behaviour of the aforementioned samples. Samples of about 5 mg, sealed (with pin hole) in a 40 μL aluminium pan, were scanned −50° C. to 200° C. using 10° C./min and a nitrogen purge of 50 ml/min. TA Universal analysis software (v 4.5A, TA Instruments, Elstree, UK) was used to analyse the data after collection in both TGA and DSC.

The effect of water on the plasticity ($T_g$) of the polymer in the extruded filaments were studied using freshly extruded filaments, 1 hour dried filaments and 4 hour dried filaments. Measurements were done in triplicate.

HPLC Methods

Hydrocortisone HPLC Method:

The HPLC analysis was performed using Agilent 1260 series UV-HPLC (Agilent Technologies, Germany) equipped with a Synergi Polar column (250×4.6 mm, 4 μm particle size) (Phenomenex, Macclesfield, UK) at 35° C. The analysis was carried out at a detection wavelength of 254 nm, flow rate of 1 mL/min, injection volume of 100 μL and a 4 minute run time. The mobile phase consisted of a 1:1 mixture of solvent A (acetonitrile) and solvent B (water).

Theophylline HPLC Method:

For theophylline, the same UV-HPLC system and column were used as detailed above for hydrocortisone. The mobile phase constituted of 10 mM solution of ammonium acetate buffer, methanol and acetonitrile (86:7:7). Analysis was carried out at a wavelength of 272 nm, temperature of 40° C., flow rate of 1 ml/min, injection volume of 5 μL and a run time of 7 min.

Sample Preparation:

In order to examine the effect of hot melt extrusion (HME) and FDM 3D printing on the integrity of the active pharmaceutical ingredient (API), API-loaded filaments were analysed for API content post drying as well as in the 3D printed tablets. Samples (API loaded filaments or tablets) were accurately weighed and placed in 250 mL of 1:1 water:acetonitrile mixture for 2 hour under sonication. The solutions were filtered through 0.22 μm Millex-GP syringe filters (Merck Millipore, USA) and prepared for HPLC analysis.

Figure 2:
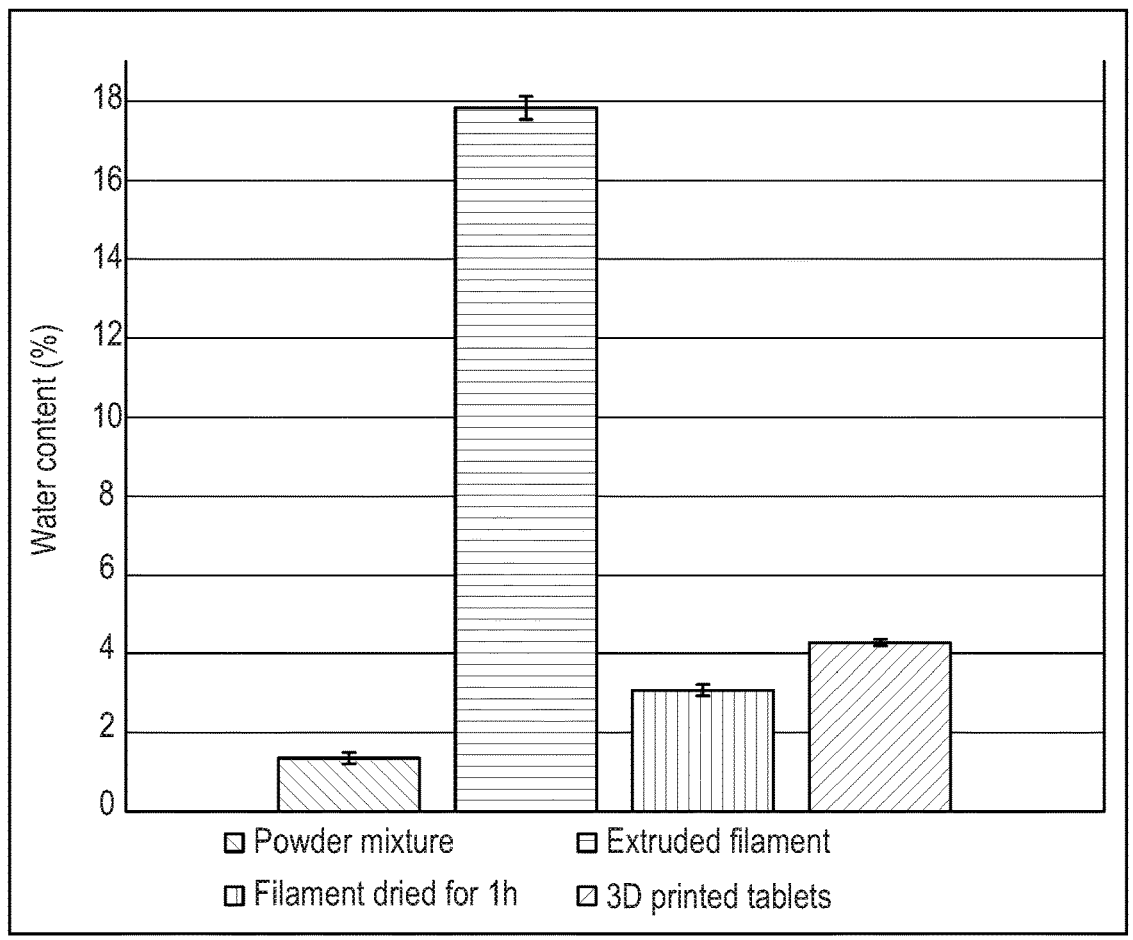
FIG. 2: Water content for a powder mixture (control), an extruded filament, an extruded filament dried for 1 hour at 100° C., and a 3D-printed tablet.

Results:

PVA has a $T_g$ of 45° C. and an endothermic event in the DSC corresponding to the melting of the crystals within the semi-crystalline matrix of this polymer. PVA has to be extruded at a temperature >180° C. in order to ensure a smooth extrusion of the polymer filament. Plasticisers can be used to reduce the temperature of extrusion. For example, sorbitol can be used to lower the extrusion temperature to 140° C. (Grymonpre W, De Jaeghere W, Peeters E, Adriaensens P, Remon J P, Vervaet C. The impact of hot-melt extrusion on the tableting behaviour of polyvinyl alcohol. International Journal of Pharmaceutics. 2016; 498(1):254-262) but the amount of plasticiser required to achieve this extrusion temperature results in PVA:sorbitol filament being too flexible and therefore is incompatible with FDM 3D printing processes. A 70:30 PVA:sorbitol mixture ($T_g$ of 55° C.) is compatible for FDM 3D printing however but this composition requires high processing temperatures (extrusion temperature of 180° C. and FDM 3D printing temperature of 200° C.). Adding water (ratio of dry ingredients: water of 100:20) enabled the extrusion of PVA/sorbitol filament (drug free) at a significantly decreased temperature of 90° C. The drop in the $T_g$ of the filament to approximately −15° C. (FIG. 1) resulted in a highly flexible filament that proved to be incompatible to FDM 3D printer's nozzle. However, when the resultant filaments were dried for 1 hour at 100° C. the water content was reduced by 14.15±0.07% (see FIG. 2) and restored an ideal flexibility of the filament for FDM 3D printing (a $T_g$ value of −10° C.; FIG. 1). The resulting filament was deemed appropriate for FDM 3D printing at 150° C. and yielded 3D printed tablets with residual water content of 4.28±0.05% (FIG. 2).

Figure 3:
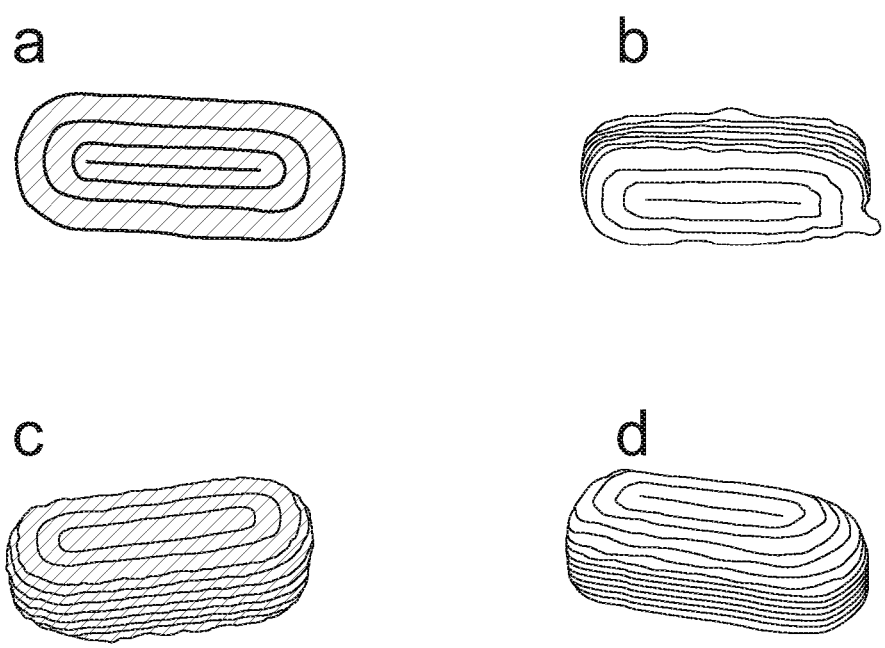
FIG. 3: Photographs of theophylline loaded PVA tablets printed at a). 210° C. without water b). 150° C. with water, and hydrocortisone loaded PVA tablets printed at c). 210° C. without water and d). 150° C. with water.

FIG. 3 shows the yielded tablets containing theophylline and hydrocortisone printed with and without water being present in the composition.

HPLC analysis of the theophylline and hydrocortisone containing filaments and tablets prepared with and without the presence of water showed that the use of high temperatures had a detrimental effect on the assay of hydrocortisone in said filament and tablet (hydrocortisone is thermally sensitive). Table II shows that only 20% of hydrocortisone is recovered in a filament prepared without the addition of a temporary plasticiser (extrusion temperature of 180° C.) versus 100% recovery when a filament is prepared from a composition containing a temporary plasticiser (extrusion temperature of 90° C.). However, in 3D-printing a tablet from the hydrocortisone and water containing filament (printing temperature of 150° C.) degradation of hydrocortisone was observed (48.6% recovery). In comparison if no temporary plasticiser a printing temperature of 210° C. is required (3.02% recovery). Theophylline containing filaments and tablets were successfully prepared with and without the presence of a temporary plasticiser. This data demonstrates that the use of a temporary plasticiser allows filaments and tablets to be prepared and reduces the amount of degradation of a thermally sensitive active ingredient observed during the filament forming process and 3D printing.

TABLE II

Impact of printing temperature on the potency of drug following HME and FDM 3D printing. (Method with temporary plasticiser used 90° C. for HME followed by 150° C. for 3D-printing. The method without temporary plasticiser used 180° C. for HME followed by 210° C. for 3D-printing.)

|  | Theophylline Residual Percentage | | Hydrocortisone residual percentage | |
| --- | --- | --- | --- | --- |
|  | Temporary plasticiser | No temporary (plasticiser) | Temporary plasticiser | No temporary (plasticiser) |
| Filament | 100% ± 0.046 | 100.61% ± 0.39 | 100.9% ± 0.1 | 19.98% ± 1.13 |
| Tablets | 100.2% ± 1.1 | 100.53% ± 0.33 | 48.6% ± 1.8 | 3.02% ± 3.45 |

Example 3: To Prove the Suitability of the System for Different Active Pharmaceutical Ingredients Filaments were prepared with the target concentration of components as detailed in Table III. 10 g of the dry ingredients (% weights according to Table III) was blended with 2 g of distilled non-ionised water (temporary plasticiser) using a mortar and pestle. The resulting blends were fed to a hot melt extruder at 90° C. and mixed at 100 rpm. A Thermo Scientific HAAKE MiniCTW hot melt extruder (Karlsruhe, Germany) was used to prepare the filaments. The filaments were dried for 1 hour at 100° C. in a drying and heating chamber (Binder Inc., series ED, Tuttinglen, Germany) and then used in 3D printing using the methodology described in Example 2 (i.e., nozzle temperature of 150° C.).

TABLE III

Composition of filament loaded with individual drug or a combination

| Filament | Ingredients (% weight) | | | | | | |
| --- | --- | --- | --- | --- | --- | --- | --- |
|  | Lisinopril | Amlodipine | Indapamide | Rosuvastatin | PVA | Sorbitol | TiO$_2$ |
| Lisinopril filament | 20 | — | — | — | 56 | 23 | 1 |
| Amlodipine besylate filament | — | 10 | — | — | 63 | 27 | — |
| Indapamide filament | — | — | 5 | — | 66.5 | 27.5 | 1 |
| Rosuvastatin calcium filament | — | — | — | 20 | 56 | 23 | 1 |
| Uni-matrix filament | 5 | 2.5 | 1.25 | 5 | 60.35 | 25.9 | — |

Drug Content Analysis Via High Performance Liquid Chromatography HPLC Method

A HPLC method was developed and validated in order to assess the assay of the active substances in the extruded filaments and the 3D printed tablets. Each sample was accurately weighed (approximately 5 mg) and placed in a 1000 ml volumetric flask and dissolved in a mixture of water:acetonitrile:methanol (80:10:10). The solutions were then filtered through an Econofltr 0.2 μm syringe (Agilent Technologies Ltd., Cheadle, UK) and analysed by HPLC.

Lisinopril dihydrate, indapamide, rosuvastatin calcium and amlodipine content was assessed using Agilent UV-HPLC 1260 series (Agilent Technologies, Germany) equipped with a synergy max column (250×4.6 mm, 4 μm particle size), at temperature of 50° C. The analysis was carried out at 210 nm wavelength, flow rate 1 mL/min, injection volume was 100 μl and run time of 35 minutes. The mobile phase consisted of acetonitrile (A) and buffer pH3 (B) (which was prepared by adjustment of the pH of distilled water with phosphoric acid) according to the gradient in Table IV. Drug assay of the multi-layer polypill I (prepared from the uni-matrix) was assessed based on the assumption that each layer corresponds to an equal part of the tablet.

TABLE IV

HPLC gradient conditions

| Time | % of Acetonitrile | % of pH3 buffer |
| --- | --- | --- |
| 0 | 17 | 83 |
| 4 | 17 | 83 |

TABLE IV-continued

HPLC gradient conditions

| Time | % of Acetonitrile | % of pH3 buffer |
| --- | --- | --- |
| 6 | 20 | 80 |
| 32 | 90 | 10 |

TABLE IV-continued

| HPLC gradient conditions | | |
| --- | --- | --- |
| Time | % of Acetonitrile | % of pH3 buffer |
| 32.01 | 10 | 90 |
| 35 | 10 | 90 |

Dissolution Studies

The release profile of the immediate release 3D printed tablets was analysed using USP type II apparatus with paddle at a rotation speed 50 rpm in 900 mL of simulated gastric fluid. For dissolution test of amlodipine besylate, the paddles were covered with tape in order to avoid interaction of the drug with the stainless steel. The experiments were performed in triplicate in dissolution media 37° C.±5° C. Aliquots were manually collected (5 mL) using an Econofltr 0.2 μm syringe (Agilent Technologies Ltd., Cheadle, UK) at dissolution times 5, 10, 15, 20, 30, 45, 60, 90 and 120 minutes. The samples were analysed by the HPLC method described previously.

Figure 4:
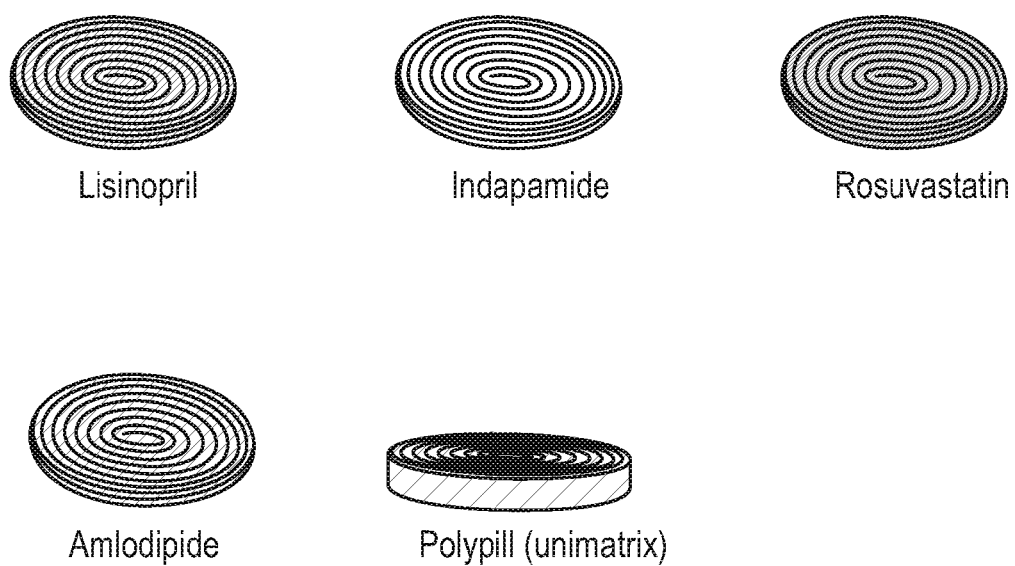
FIG. 4: Photographs of 3D printed tablets loaded with lisinopril dihydrate, indapamide, rosuvastatin calcium and amlodipine, and the polypill (unimatrix).

Results:

FIG. 4 shows photographs of five tablets prepared which are loaded with Lisinopril dihydrate, indapamide, rosuvastatin calcium and amlodipine, and the polypill (prepared from unimatrix filament).

Figure 5:
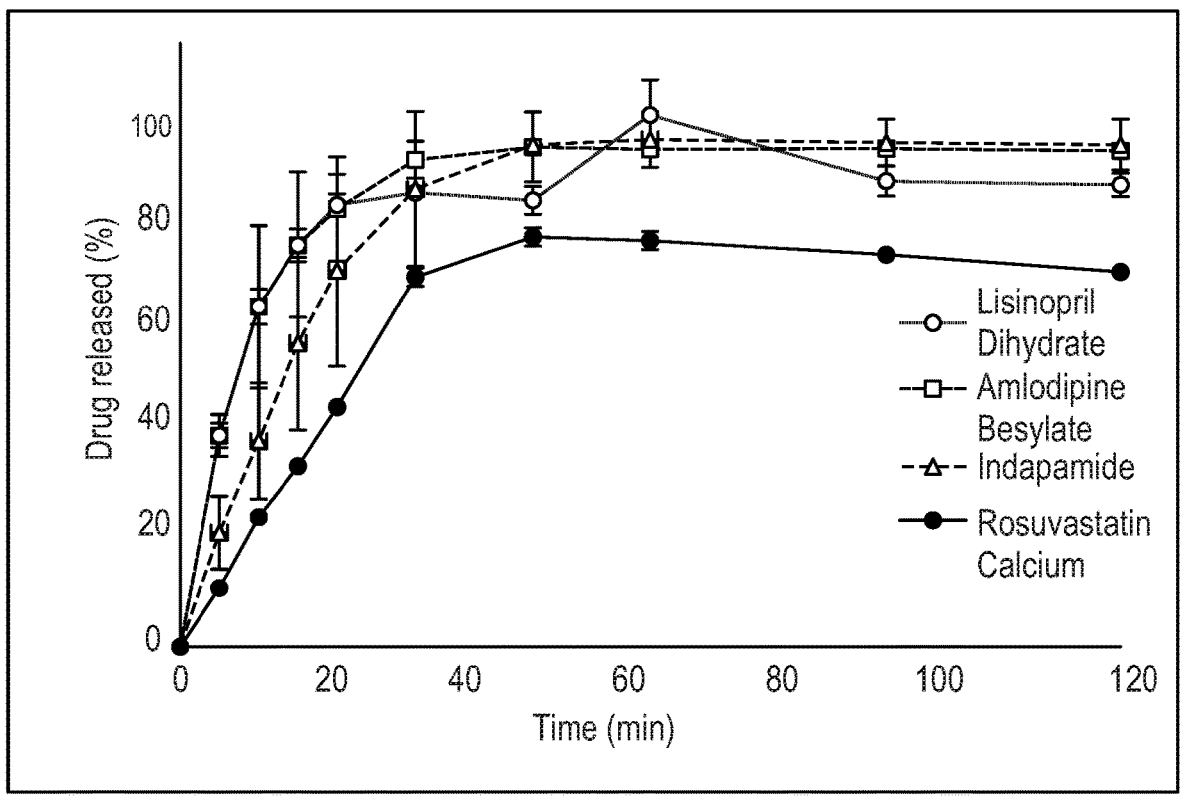
FIG. 5: In-vitro drug release analysis in a gastric medium of the lisinopril, indapamide, rosuvastatin and amlodipine containing individual tablets.

FIG. 5 shows the in vitro release in a gastric medium of the lisinopril, indapamide, rosuvastatin or amlodipine containing individual tablets. The tablets tested each dissolved within 45 minutes and complied with the British Pharmacopeia criteria for immediate release products.

The dimensions of the prepared tablets and their weight uniformity is presented in Table V as well as the percentage recovery of the active ingredient in the filament and tablet.

layer by layer. This type of direct ink writing of 3D printing has been used in pharmaceutical manufacturing. However, there are a number of disadvantages to direct ink writing; these include organizing the flow from non-Newtonian fluids (suspension), the high contents of the solvent residues, shrinkage of dosage form, and the need for additional drying step.

On the other hand, FDM 3D printing provides an alternative for manufacturing of dosage forms by employing a filament as a feed for the hot nozzle. However, such approach faces number of challenges, such as use of high temperature thermal processes for both hot melt extrusion and FDM 3D printing, which can lead to significant drug degradation in this multi-step process. The need for filament as a pre-product may increase the cost of production.

In this newly proposed method, there is provided a combination of direct ink writing that is facilitated by 1) elevating the temperature of the syringe, 2) the addition of distilled non-ionised water (as a temporary plasticiser) 3) evaporation use of elevated temperature plate.

This approach allows the production of a tablet by direct extrusion of material at relatively low temperatures (90° C.) in a single process.

Preparation 4a: Preparation of a PVA Based Filament and Tablet Using TASFEX Printing The following components were mixed together for two minutes using a blade mixer and subsequently used to produce a filament and a tablet.

3.5 g PolyVinyl Alcohol (PVA) Partech MXP
1.5 g Sorbitol
4.5 g Theophylline (model drug)
0.5 g Sodium stearyl Fumarate (PRUV)
2 g Distilled non-ionised water

TABLE V

| | Dimension | | | Weight Uniformity | Drug contents in filament | | |
| --- | --- | --- | --- | --- | --- | --- | --- |
| Tablet | X | Y | Z | ±SD (mg) | Lisinopril | Amlodipine | Indapamide |
| Lisinopril dihydrate | 12.88 ± 0.12 | 7.98 ± 0.08 | 0.59 ± 0.07 | 49.4 ± 5.6 | 93.9 ± 1.66 | | |
| Amlodipine besylate | 12.89 ± 0.09 | 7.89 ± 0.1 | 0.62 ± 0.03 | 51.58 ± 1.6 | | 97.89 ± 1.94 | |
| Indapamide | 12.99 ± 0.18 | 7.92 ± 0.15 | 0.55 ± 0.69 | 51 ± 3.2 | | | 93.32 ± 1.67 |
| Rosuvastatin calcium | 13.12 ± 0.08 | 8.1 ± 0.09 | 0.53 ± 0.04 | 51.2 ± 0.75 | | | |
| Polypill (unimatrix) | 12.99 ± 0.07 | 8.17 ± 0.08 | 1.95 ± 0.05 | 199.03 ± 6.81 | 99.2 ± 2.9 | 92.8 ± 8.1 | 95.4 ± 5.2 |

| | Drug contents in filament | Drug contents in tablets | | | |
| --- | --- | --- | --- | --- | --- |
| Tablet | Rosuvastatin | Lisinopril | Amlodipine | Indapamide | Rosuvastatin |
| Lisinopril dihydrate | | 87.8 ± 1.5 | | | |
| Amlodipine besylate | | | 90.68 ± 2.28 | | |
| Indapamide | | | | 96.06 ± 2.06 | |
| Rosuvastatin calcium | 98.2 ± 1.09 | | | | 95.4 ± 2.37 |
| Polypill (unimatrix) | 92.1 ± 2.8 | 100.6 ± 2.81 | 87.54 ± 0.32 | 96.3 ± 1.92 | 88.93 ± 3.94 |

Example 4: Temperature and Solvent Facilitated Extrusion (TASFEX) 3D Printing

Figure 6:
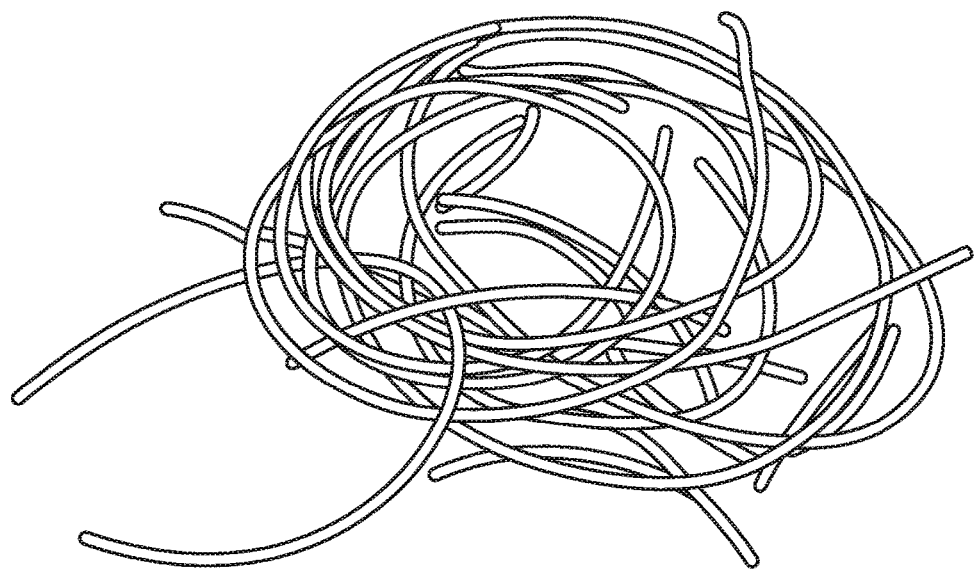
FIG. 6: Photograph of a filament produced by TASFEX 3D printing

Direct ink writing is an additive manufacturing technique. A composition is extruded from a moving nozzle onto a platform. An object is obtained by writing the desired shape A smooth white filament was produced (FIG. 6) by extruding the blend (12 g) (extrusion temperature of 95-100° C., G18 nozzle and a plate temperature of 70-75° C.).

Another blend (12 g; same composition as stated above) was packed and produced a tablet using Hyrel M30 3d printer equipped with KRA-15 nozzle head. The following settings were used (Table VI):

TABLE VI

| Printer | Hyrel 3D printer |
|---|---|
| Software | Slic3r |
| Syringe | Krakatoa (body) |
|  | Volcano (actual syringe) |
| Tip | 16 Gauge |
| Warming | 100° C. for 30 min |
| Head Temperature | 100° C. |
| Plate Temperature | 50° C. until RT |
| Layer Thickness | 0.3 mm |
| 1st Layer Thickness | 0.8 mm |
| Infill/Perimeter Overlap | 100% Rectilinear |
| External Perimeters | 50% |
| Infill | 4 mm/s |
| Travel | 15 mm/s |
| 1st Layer | 4 mm/s |
| All other | 2 mm/s |
| Speed | 2 mm/min |
| Go-G1 Tag | 1500 |
| Extrusion Multiplier | 1 |
| Nozzle Diameter | 1 mm |
| Filament Diameter | 1 mm |
| Rotations* | 700 |
| Tablet Dimensions | X = 17.19 mm |
|  | Y = 6.81 mm |
|  | Z = 6.25 mm |

Figure 7:
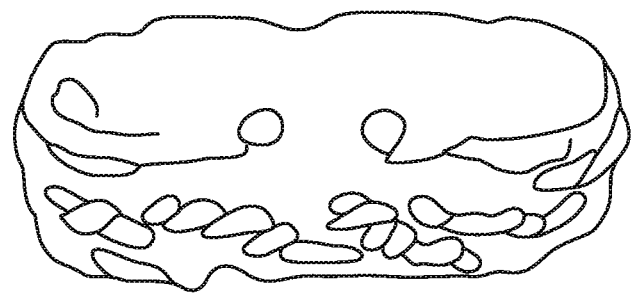
FIG. 7: Photograph of a tablet produced by TASFEX 3D printing

FIG. 7 shows the tablet obtained by TASFEX 3D printing.

Preparation 4b: Preparation of a PVA Based Tablet (Caplet and Cylindrical)

The following components were mixed together and subsequently used to produce tablets in two different designs; a caplet and a cylinder.

40% w/w Theophylline

35% w/w PVA

20% w/w Sorbitol

5% w/w Sodium stearyl fumarate (PRUV)

20% w/w distilled non-ionised water

The blend (12 g per form) was used to directly produce a caplet and a cylinder using Hyrel M30 3d printer equipped with KRA-15 nozzle head. The following settings were used (Table VII):

TABLE VII

| Printer | | Hyrel 3D System 30M |
|---|---|---|
| Slicing software | | Slic3r |
| Main Software | | Repetrel |
| Modular Head | | VOL-25 (Volcano) |
| Tip | | 18 Gauge |
| Warming | | 100° C. for 30 min |
| Head Temperature | | 90° C. |
| Plate Temperature | | 50° C. |
| Layer Thickness | | 0.3 mm |
| 1st Layer Thickness | | 0.5 mm |
| Infill/Perimeter Overlap | | 100% Rectilinear |
| Speed | External Perimeters | 50% |
|  | Infill | 9 mm/s |
|  | Travel | 15 mm/s |
|  | 1st Layer | 4 mm/s |
|  | All over | 7 mm/s |
| Go-G1 Tag | | 1500 |
| Extrusion Multiplier | | 1 |
| Nozzle Diameter | | 0.838 mm |
| Filament Diameter | | 0.838 mm |
| Head Settings | Nozzle diameter | 0.838 mm |
|  | Layer Z | 0.3 mm |
|  | Pulses/nL | 2.28 |
|  | Material flow rate multiplier | 0.9 |
| Caplet Design Dimensions | | X = 17.19 mm |
|  | | Y = 6.81 mm |
|  | | Z = 6.25 mm |
| Cylindrical Design Dimensions | | Radius = 10 mm |
|  | | Height = 3 mm |

Methodology:

Scanning Electronic Microscopy (SEM)

The morphology and cross-section of the tablets were assessed using a JCM-6000 plus NeoScope™ microscope (Jeol, Tokyo, Japan) at 10 kV. All samples were gold coated using a JFC-1200 Fine Coater (Jeol, Tokyo, Japan). The images were collected using Image J software (v 1.2.0., Tokyo, Japan).

In Vitro Dissolution Testing

In vitro dissolution testing was conducted in an AT-70 Smart dissolution USP II apparatus (Sotax, Switzerland). The dissolution medium was held at 37±0.5° C. with a paddle rotation at 50 rpm. The tablets were tested in 750 mL of acidic phase (0.1 M HCl, pH 1.2) for 2 hours. The percentage of released theophylline was determined at 5 min intervals by UV/vis spectrophotometer (PG Instruments Ltd., UK) at the wavelength of 272 nm and path length of 1 mm. Data were analysed using IDISis software (Automated Lab, UK).

Figure 8:
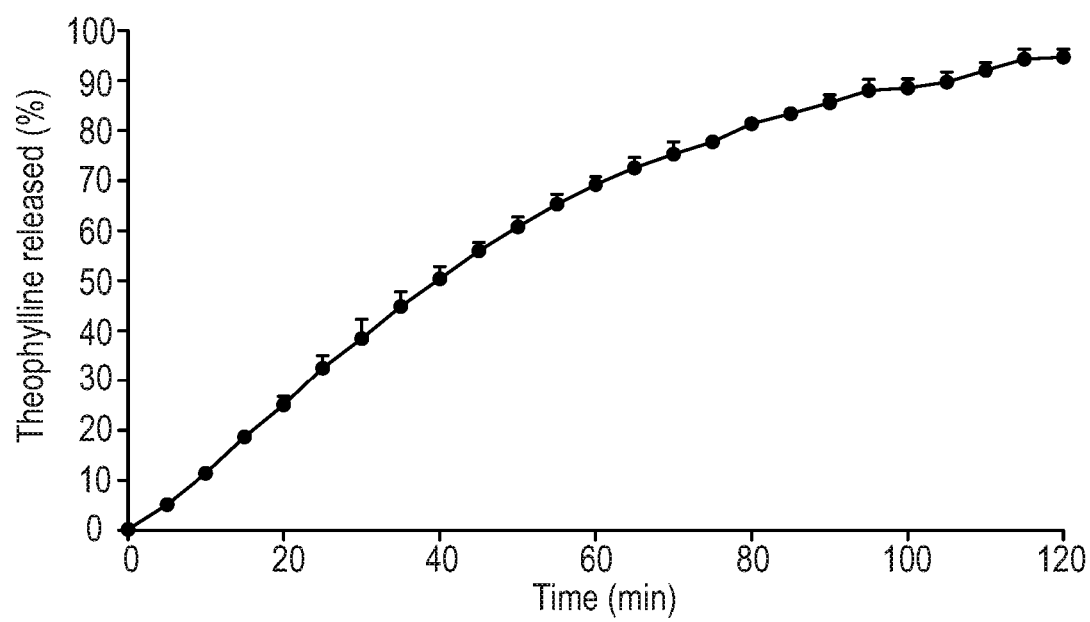
FIG. 8: In-vitro drug release analysis from a caplet produced by TASFEX printing

Results:

FIG. 8 shows the in vitro drug release from the caplet produced by TASFEX 3D-printing.

Figure 9:
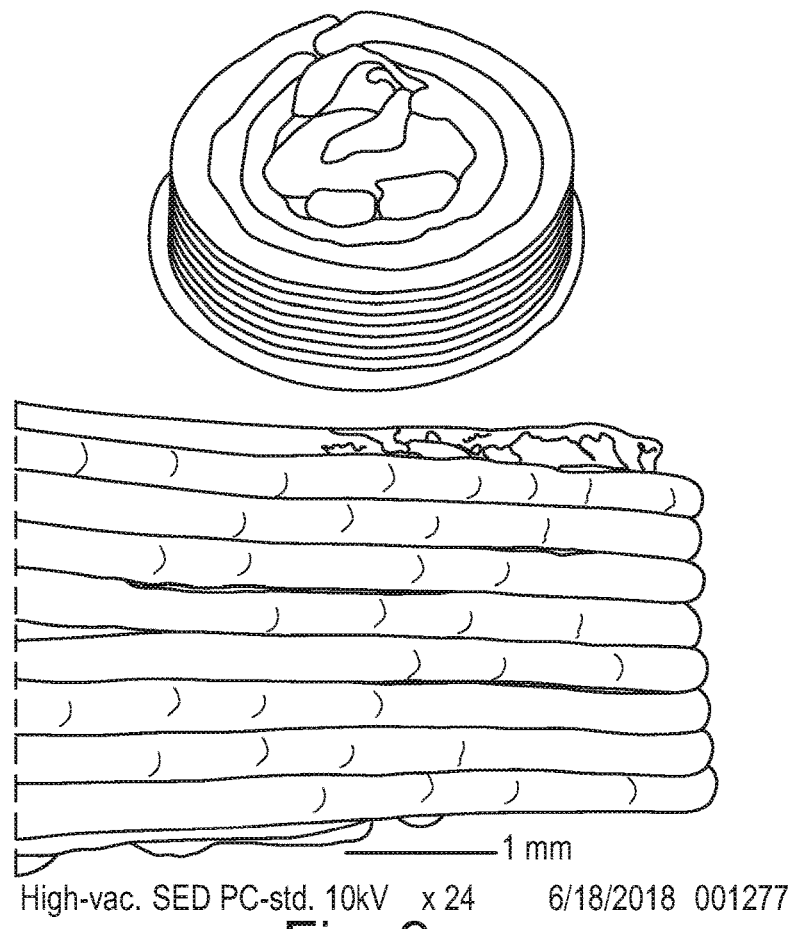
FIG. 9: Photograph and SEM images of a theophylline loaded PVA cylindrical tablet produced by TASFEX 3D printing

The produced tablet (cylindrical) showed a smooth surface and relatively high resolution as confirmed by SEM images (FIG. 9).

Figure 10:
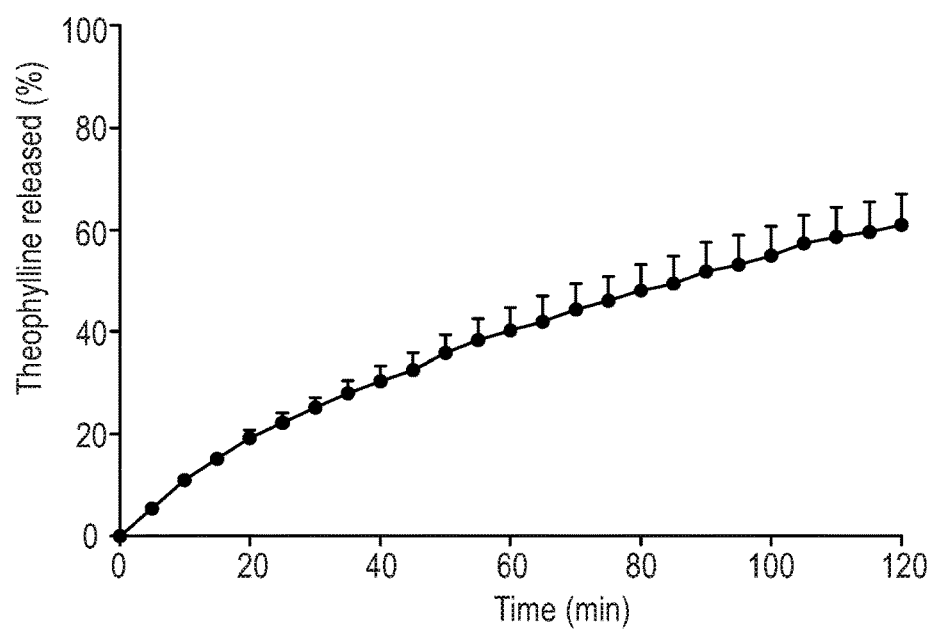
FIG. 10: In-vitro release analysis of a theophylline loaded PVA cylindrical tablet produced by TASFEX printing.

FIG. 10 shows the in vitro testing of the cylinder tablet produced by TASFEX 3D-printing.

Conclusion:

This example demonstrates it is possible to produce a tablet directly from a blend of components in a single process using a relatively low printing temperature of 95-100° C.

Example 5: Degradation of Active Ingredient Dependent on the Level of Active Ingredient Present Hydrocortisone is a thermally-sensitive molecule that is susceptible to thermal degradation above 160° C. During production of a tablet using FDM 3D printing the molecule is exposed twice to high temperatures. Firstly, during the preparation of the filament using HME and secondly during the FDM 3D printing of the filament.

Filaments were compounded according to the formulation in Table VIII using Thermo Fisher Haake MiniCTW compounder. The extruder speed was set at 35 rpm and temperature at 90° C.

TABLE VIII

| Formulation | Weight % |
|---|---|
| Hydrocortisone | 1, 5 or 10 |
| Eudragit EPO | 46.75 |
| Tricalcium phosphate | 48, 43 or 38 |
| Triethylcitrate | 3.25 |
| $TiO_2$ | 1 |

Tablets were constructed with the pre-prepared filaments using a commercial FDM 3D printer equipped with 0.4 mm nozzle size. The templates used to print the tablets were designed in a caplet shape using Autodeski 3ds Maxi Design 2012 software version 14.0 (Autodesk, Inc., USA). The design was saved in a stereo-lithography (.stl) file format and was imported to the 3D software, MakerWare Version 3.9.1.1143 (Makerbot Industries, LLC., USA). Tablets were printed using modified settings of the software for PLA: as follows: type of printer: Replicator 2×; resolution: standard; speed of extruder 90 mm/s while extruding and 150 mm/s while traveling; infill: 100%; height of the layer: 200 mm. No supports or rafts were utilized. The temperatures for the nozzle and build plate of the 3D printer were 135° C. and 60° C. respectively. Blue Scotch painter's tape was applied to the build platform to facilitate the adherence of the printed object during FDM 3D printing.

HPLC Analysis:

Hydrocortisone content was assessed using HPLC using the following conditions:

Mobile phase: water:acetonitrile 1:1.

Stationary phase: Phenomenex® column Synergi Polar RP column with particle size 4 μm with 80 Å pores, length of 250 mm Column temperature: 35° C.

Injection Volume: 10 μL.

Flow rate: 1 mL/min

Detection: UV, 254 nm

Retention time of hydrocortisone=around 4 minutes.

Analysis of blends used to make the extruded filament, the extruded filament and the printed tablet.

The blend powder, the extruded filament or the printed tablet were placed into a 500 mL volumetric flask along with HCl. The flasks were sonicated for 30 minutes, followed by allowing the solutions to cool back to room temperature (approximately 30 minutes). A 10 mL syringe was filled with the resulting solution. A filter was added to the syringe; the first 5 mL was discarded, the second 5 mL used to fill a HPLC vial.

Results:

In this example, it was surprising to note that percentage of residual drug increased by increasing drug loading, as shown in Table IX.

TABLE IX

| Drug Concentration | Drug potency in filament average ± SD (n = 3) | Drug potency in FDM 3D printed average ± SD (n = 3) |
| --- | --- | --- |
| 1% | 85.97 ± 0.14% | 75.13 ± 0.62% |
| 5% | 92.25 ± 0.21% | 95.4 ± 4.3% |
| 10% | 99 ± 0.34% | 98.2 ± 0.45% |

Increasing drug loading was more efficient in reducing degradation of hydrocortisone compared to using a lower drug concentration in combination of wide spectrum of anti-oxidant additives (20 different additives were screened such as vitamin C, EDTA and citric acid).

Figure 11:
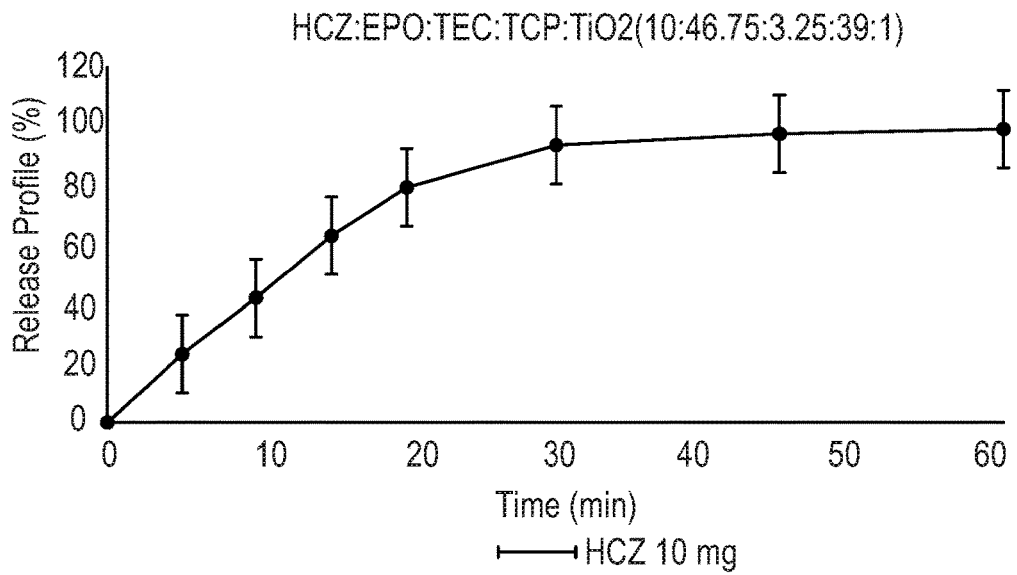
FIG. 11: In-vitro release analysis of 10% hydrocortisone loaded tablet in pH 1.2 media.

FIG. 11 shows the in vitro release testing of the 10% hydrocortisone tablet in pH 1.2 media. The in vitro dissolution methodology used was as described in Example 2 using the hydrocortisone HPLC method described above.

Preparation 4c

The following components were mixed together and subsequently used to produce a filament.

50% w/w Eudragit L100-55
47.5% w/w Theophylline
2.5% w/w sodium stearyl fumarate (PRUV)
30% w/w water The following conditions were used to prepare the filament (Table X).

TABLE X

| Printer | Hyrel 3D System 30M |
| --- | --- |
| Slicing Software | Slic3r |
| Main Software | Repetrel |
| Modular Head | VOL-25 (Volcano) |
| Tip | 18 Gauge |
| Warming | 100° C. for 30 minutes |
| Head Temperature | 90° C. |
| Plate Temperature | 50° C. |
| Layer Thickness | 0.3 mm |
| 1st Layer Thickness | 0.5 mm |
| Infill/Perimeter Overlap | 100% Rectilinear |
| Speed   External Perimeters | 50% |
|    Infill | 9 mm/s |
|    Travel | 15 mm/s |
|    1st Layer | 4 mm/s |
|    All over | 7 mm/s |
| Go-G1 Tag | 1500 |
| Extrusion Multiplier | 1 |
| Nozzle Diameter | 1.194 mm |
| Filament Diameter | 1.194 mm |
| Head Settings   Nozzle diameter | 1.194 mm |
|    Layer Z | 0.3 mm |
|    Pulses/nL | 2.28 |
|    Material flow rate multiplier | 0.9 |
| Caplet Design Dimensions | X = 17.19 mm |
|  | Y = 6.81 mm |
|  | Z = 6.25 mm |
| Cylindrical Design Dimensions | Radius = 10 mm |
|  | Height = 3 mm |

Results:

Eudragit L100-55 has proven to be compatible with the technique and the use of water as a temporary plasticiser has allowed its extrusion at 90° C. However, Eudragit L100-55 does not stick to the plate. Low printing speeds (4 mm/s) can be used in order to achieve adhesion to the plate.

Example 6: Continuous Production of a Filament

In this example the continuous production of filament is demonstrated by using a continuous feed of minitablets. This was achieved using two steps:

Step 1: Production of Minitablets 50 g of the powder mixture (Table XI) was blended together using a shear mixer followed by compression using Riva MiniPress tablet press equipped with 6 mm multi-punch tooling. Each resultant tablet had an average weight of about 51 mg.

TABLE XI

| Formulation | % |
| --- | --- |
| Hydrocortisone | 1 |
| EPO | 46.75 |
| Tri-calcium phosphate | 48 |
| TEC | 3.25 |
| TiO$_2$ | 1 |

Step 2: Production of a Filament

Continuous production of filament was achieved by feeding mini-tablets on a continuous fashion by adding 0.5 g/30 sec using Haake MiniCTW extruder (Thermo Fisher) and was received by a conveyor belt with a rotating speed 2.5.

Example 7: Additional Excipients Present in the Extrudable Composition and Extruded Item The formulation is similar to Example 5 however, sodium stearyl fumarate was added to the formulation at 4%. It has proved to have visually accelerated tablet disintegration. The formulation composition is according to Table XII.

TABLE XII

| Formulation | % |
|---|---|
| Hydrocortisone | 10 |
| Eudragit EPO | 46.75 |
| Tri-calcium phosphate | 35 |
| Sodium Stearyl fumarate | 4 |
| TEC | 3.25 |
| TiO$_2$ | 1 |

Example 8: Production of an Embedded Item Using Embedded 3D-Printing

An embeddable substance was prepared by mixing the following components together with a composition according to Table XIII. Mixing was performed manually at room temperature using a pestle and mortar.

TABLE XIII

| Substance | Amount | In 1 mL (one dose) |
|---|---|---|
| Ibuprofen | 10 g (powder) | 0.1 g |
| NaOH | 2 g (powder) | 0.02 g |
| Sodium alginate (Manucol) | 8 g (powder) | 0.08 g |
| Water | 100 mL | 1.0 mL |

A solidifiable body substance was prepared by mixing the following substances together at 70° C. to form a gelatine matrix (Table XIV).

TABLE XIV

| Substance | % (w/v) |
|---|---|
| Gelatine | 25 g (powder) |
| Glycerol | 30 mL |
| Water | 45 mL |

The solidifiable body substance (gelatine solution; 10-12 mL) was poured (in one or two steps) into a template that was heated to 40° C. Then, the embeddable substance (ibuprofen gel) was embedded into the solidifiable body substance using 3D printing. This was followed by cooling the resulting structure to room temperature in order to solidify the solidifiable body substance.

Figure 12:
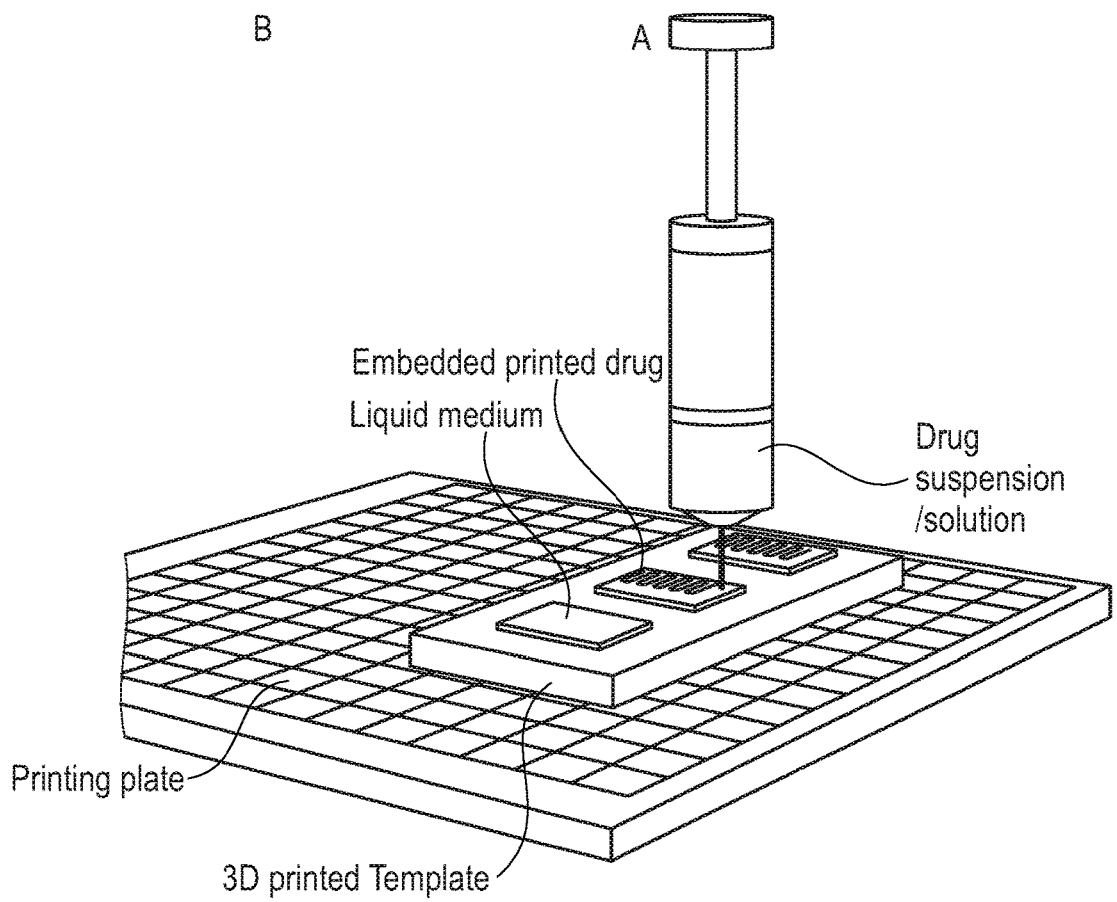
FIG. 12: Schematic of an embedding apparatus.

A schematic of the 3D printing apparatus is provided in FIG. 12. Part A of this figure shows a schematic of embedded 3D printing wherein a liquid medium is cast into a 3D printed template, and a drug solution is embedded through computer controlled software. Part B of this figure shows a photograph of drug (red lines) loaded in gelatine based chewable tablet formed in shape of Lego® bricks.

In Vitro Dissolution Testing Methodology:

The release profile of the immediate release 3D printed tablets was analysed using USP type II apparatus with paddle at a rotation speed 50 rpm in 900 mL of simulated gastric fluid. For dissolution test of amlodipine besylate, the paddles were covered with tape in order to avoid interaction of the drug with the stainless steel. The experiments were performed in triplicate in dissolution media 37° C.±5° C. The percentage of released active was determined at 5 min intervals by UV/vis spectrophotometer (PG Instruments Ltd., UK) at the wavelength of 221 nm and path length of 1 mm. Data were analysed using IDISis software (Automated Lab, UK).

HPLC Methodology:

Agilent 1200 system was used for the detection of paracetamol and ibuprofen, the system was equipped with Kinetex 3.5 μm XB-C18 Size-LC Column 100×4.6 mm. The mobile phase was 0.1% phosphoric acid pH2.2:ACN (35:65). The injection volume was 2 μL and the flow rate was 0.5 ml/min. The temperature of the column was 45° C. The detection was tested at a wavelength of 210 nm. The retention time for paracetamol is 1.9 min and for ibuprofen 4.2 min.

Figure 13:
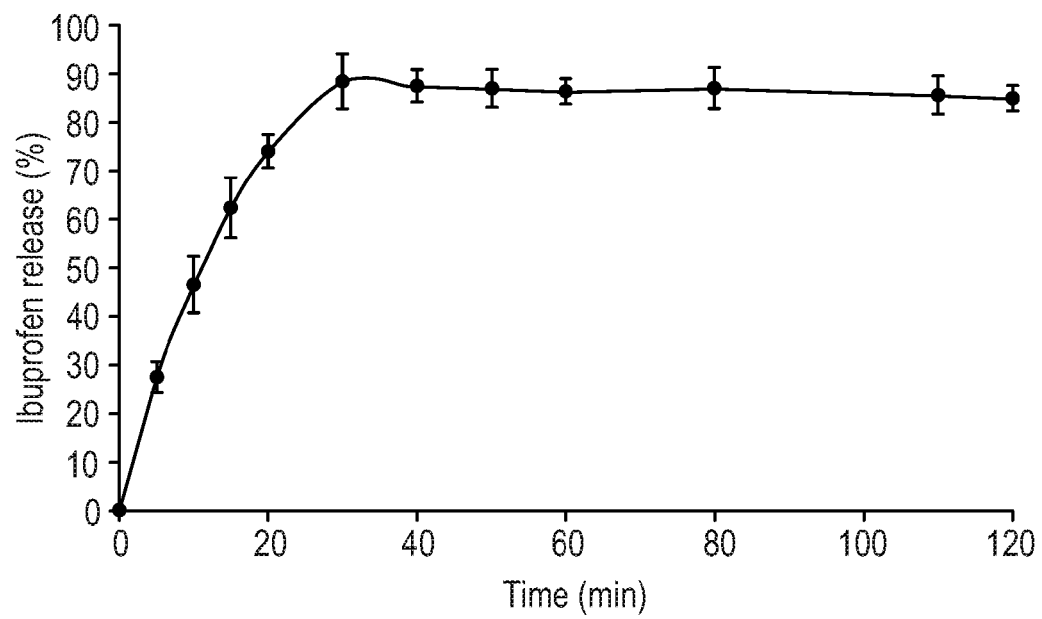
FIG. 13: In-vitro release analysis of chewable tablets containing ibuprofen in intestinal medium.

Results:

FIG. 13 shows the drug release pattern of the chewable tablets containing ibuprofen in intestinal medium.

Figure 14:
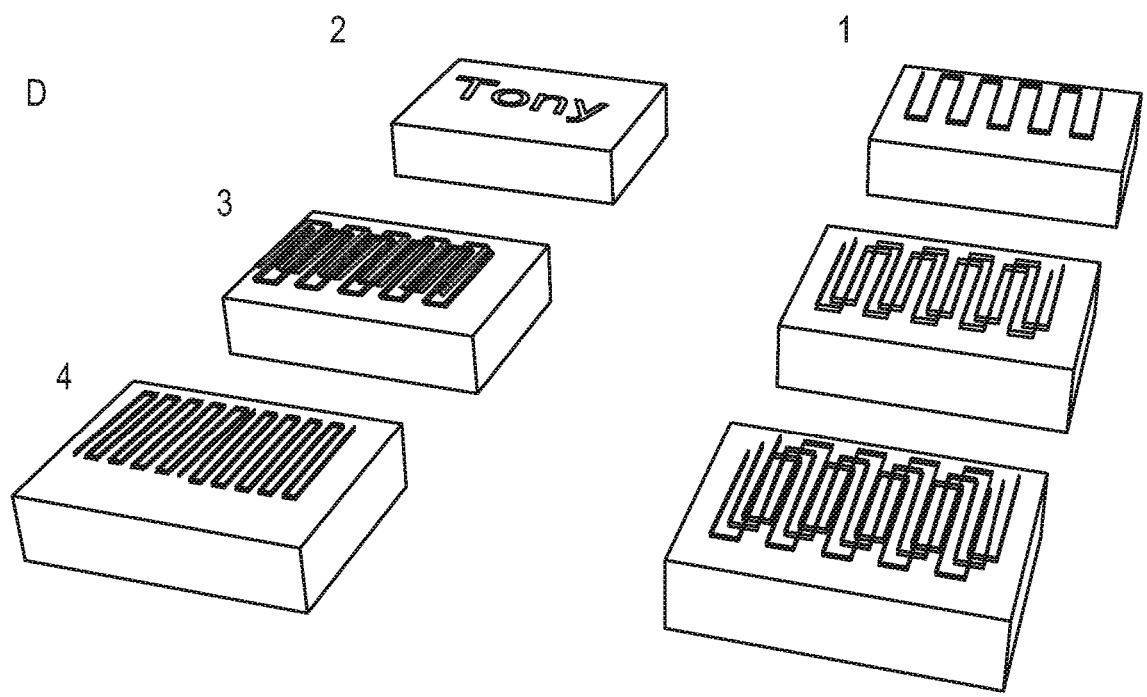
FIG. 14: Schematic showing potential applications of embedded 3D-printing: for use in dose titration (1), dose personalisation (2), combining two active ingredients (3) and sequential drug release in multi-drug modified release systems.

FIG. 14 shows potential applications of embedded 3D-printing. For example, for use in dose titration (1), dose personalisation (2), combining two active ingredients (3) and sequential drug release in multi-drug modified release systems.

Example 9: Demonstrating Two Different Methods to Prepare an Embedded Item and how the Extruder Parameters can be Varied in Order to Control the Active Ingredient Dose in an Embedded Item Two different methods of producing an embedded item were tested along with altering the extruder multiplier and printing pattern in order to see how these affected how much of the embeddable substance was embedded within the solidifiable body substance, and consequently the dose of an active ingredient in the embedded item.

Figure 15:
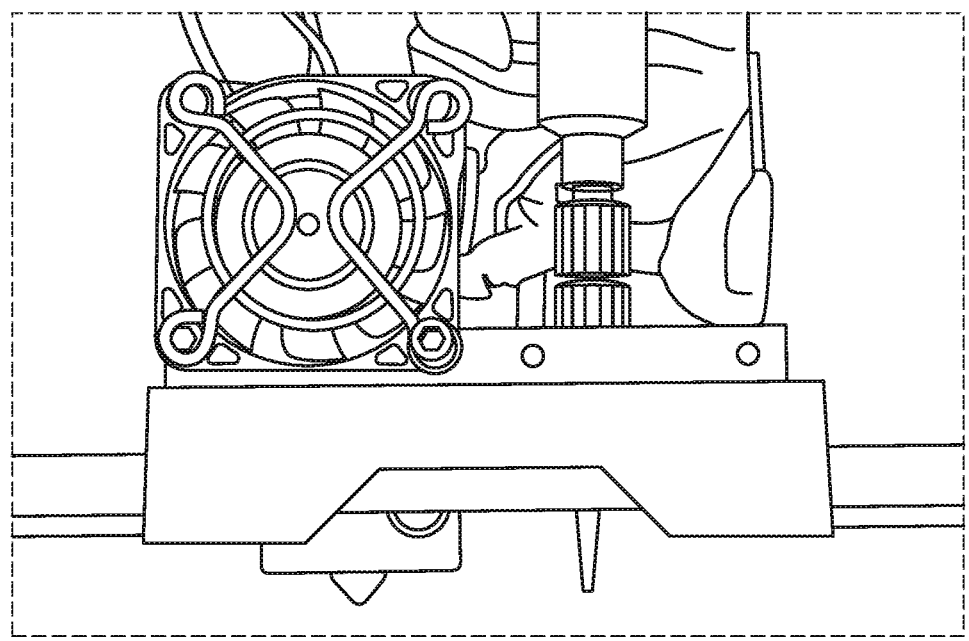
FIG. 15: Photograph showing the modification of dual FDM 3D printer to accommodate a liquid dispenser (right) in combination with FDM 3D printer head (left).

3D-Printer Settings:

In order to devise a fully automated manufacturing of the embedded item, a Makerbot Replicator Experimental 2× dual FDM 3D printer (MakerBot Industries, New York, USA) was modified. The printer has two FDM nozzle heads. The right extruder/head of the dual 3D printer was replaced by a syringe-based liquid dispenser as shown in FIG. 15. The design for the dispenser was obtained from an open source design (Thingiverse, 2017) and the different parts were produced by 3D printing using an M2 Makergear FDM 3D printer and ABS filaments (MakerGear LLC, Ohio, USA). The dispenser head was assembled and equipped with either a 2 or 10 mL syringe. A Nema17 1.5 A 4-lead stepper motor (MakerBot Industries, New York, USA) was connected to the motherboard using the default housing connectors.

Figure 16:
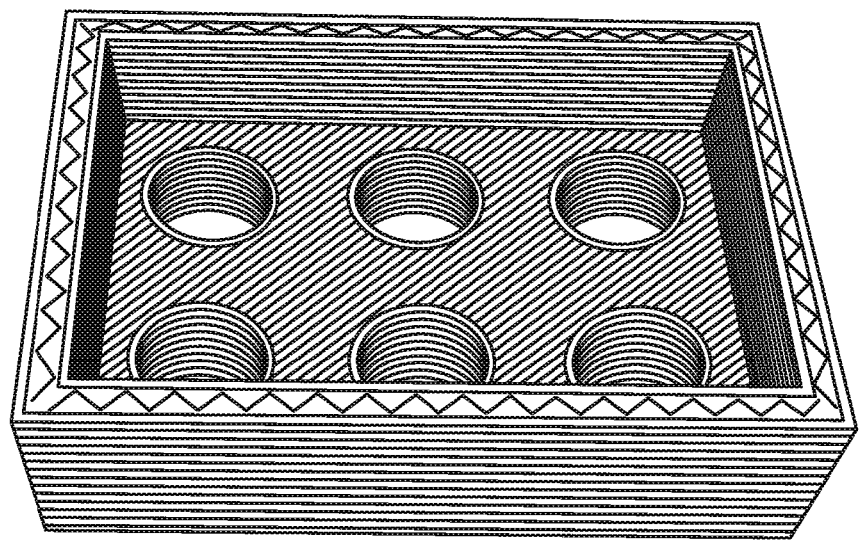
FIG. 16: Photograph of a mould for a gelatine cast.

Nozzle diameter 0.40 mm
Extruder Multiplier 10.00
Printing speed 55.0 mm/min
Nozzle diameter 0.4 mm
Outline 0
Infill 100 percent
Mould for Gelatine Cast A template based on lego design was printed the dimensions was 44×28×8 mm space, see FIG. 16. This template was printed using FDM 3D printer and PLA filament. Please note that the template can be in any shape and the capacity. In this case the template's capacity was approximately 12 mL.

Two different way of embedded printing were demonstrated.

Method I: Single Step Embedded 3D Printing

In this method the template is completely filled with gelatine solution (composition as detailed in Table XIV) at 70° C. Then the tip of the syringe is calibrated to be at 4 mm height (middle level of the 8 mm height). The computer-controlled syringe was used to apply the drug suspension within the gelatine at 70° C. However, when the embedded item was printed it was found using the current settings that no regular pattern could be achieved and there was significant variation in dose (see Table XV).

Methodology:

Embeddable substance used: 40 g paracetamol and 60 g (locust gum 2%), i.e., 2% weight of the 60 g is locust gum and the remaining mass balance is water Solidifiable body substance used was according to Table XIV.

Printing speed: 55 mm/min

Needle G16

Extrusion multiplier 10

Results:

TABLE XV

| Dose (mg) | | |
|---|---|---|
| Average weight of paracetamol in the embedded item | Standard Deviation (n = 3) | Standard Deviation % |
| 147.8 | 17.9 | 12.1 |

Method II: Two Step Embedded 3D Printing

In this method the template is partially filled with a gelatine solution (as detailed in Table XIV) at 70° C. and cooled until it solidified. Then a pattern of printing of a drug suspension in a single or multiple layer is applied using a computer controlled syringe. Lastly a second layer of gelatine at 70° C. is applied in a second stage and the embedded item is cooled until all of the gelatine is solidified.

The following experiments (varying the extruder multiplier, varying the needle size—experiment set 1 & set 2, varying the printing pattern, and varying the printing speed) used the two step embedded 3D printing process.

Varying the Extruder Multiplier

An embeddable substance was prepared by mixing the following components together:

40 g paracetamol 60 g (locust gum 2%), i.e., 2% weight of the 60 g is locust gum and the remaining mass balance is water The extruder multiplier was varied during this experiment. Experiments were run with the extruder multiplier set at 3.0, 5.0 and 10.0 (three experiments per extruder multiplier). The embeddable substance was printed using a G16 filament and 55 mm/min.

Results:

It is possible to control the dose of the active ingredient (paracetamol) by changing the setting of the extrusion multiplier, as shown in Table XVI.

TABLE XVI

| | Dose (mg) | | |
|---|---|---|---|
| Extruder Multiplier | Average weight of paracetamol in the embedded item | Standard Deviation [n = 3] | Standard Deviation % |
| 3.0 | 45.8 | 0.9 | 2.0 |
| 5.0 | 73.0 | 2.6 | 3.5 |
| 10.0 | 104.1 | 7.2 | 7.0 |

Conclusions:

As shown in examples from single and two steps embedded 3D printing, the variation in dosing is significantly lower in two step embedded 3D printing compared to one step.

Varying the Needle Size-Experiment Set 1

An embeddable substance was prepared by mixing the following components together in a pestle and mortar at room temperature:

40 g paracetamol 60 g (locust gum 2%), i.e., 2% weight of the 60 g is locust gum and the remaining mass balance is water The solidifiable body substance used is as detailed in Table XIV.

The needle size was varied during this experiment. Three experiments were run per needle size G17 (0.042"/1.06 mm), G16 (0.053"/1.35 m) and G15 (0.06"/1.52 mm)). The embeddable substance was printed using a 5.0 extruder multiplier and 55 mm/min.

Results:

It is possible to control the active ingredient dose (paracetamol) by changing the size of the needle, as shown in Table XVII.

TABLE XVII

| | Dose (mg) | | |
|---|---|---|---|
| Needle | Average weight of paracetamol in the embedded item | Standard Deviation n = 3 | Standard Deviation % |
| G17 | 28.7 | 0.7 | 2.3 |
| G16 | 116.6 | 7.0 | 6.0 |
| G15 | 171.2 | 6.0 | 3.5 |

Varying the Needle Size-Experiment Set 2

An embeddable substance was prepared by mixing the following components together using a pestle and mortar at room temperature:

28 g ibuprofen 72 g (locust gum 2%) i.e., 2% weight of the 72 g is locust gum and the remaining mass balance is water The solidifiable body substance used was as detailed in Table XIV.

The needle size was varied during this experiment. Experiments were run using needle sizes G16 and G15 (three experiments run per needle size). The embeddable substance was printed using a 10 extruder multiplier and 55 mm/min.

Results:

It is possible to control the active ingredient dose (ibuprofen) by changing the size of the needle, as shown in Table XVIII.

TABLE XVIII

| | Dose (mg) | | |
|---|---|---|---|
| Needle | Average | Standard Deviation n = 3 | Standard Deviation % |
| G16 | 57.5 | 1.1 | 1.9 |
| G15 | 72.0 | 1.4 | 2.0 |

Varying the Printing Pattern

An embeddable substance was prepared by mixing the following components together using a pestle and mortar at room temperature:

40 g paracetamol 60 g (locust gum 2%) i.e., 2% weight of the 60 g is locust gum and the remaining mass balance is water The solidifiable body substance used is as detailed in Table XIV.

The percentage of the printing pattern was varied during this experiment (25%, 50%, 75%, 100%, 150%, 200%, 300% and 400% wherein 100% is the full design, 25% is quarter of the design and 200% is the design printed twice etc.). The embeddable substance was printed using a 5.0 extruder multiplier, 55 mm/min and a needle size G17.

Figure 17:
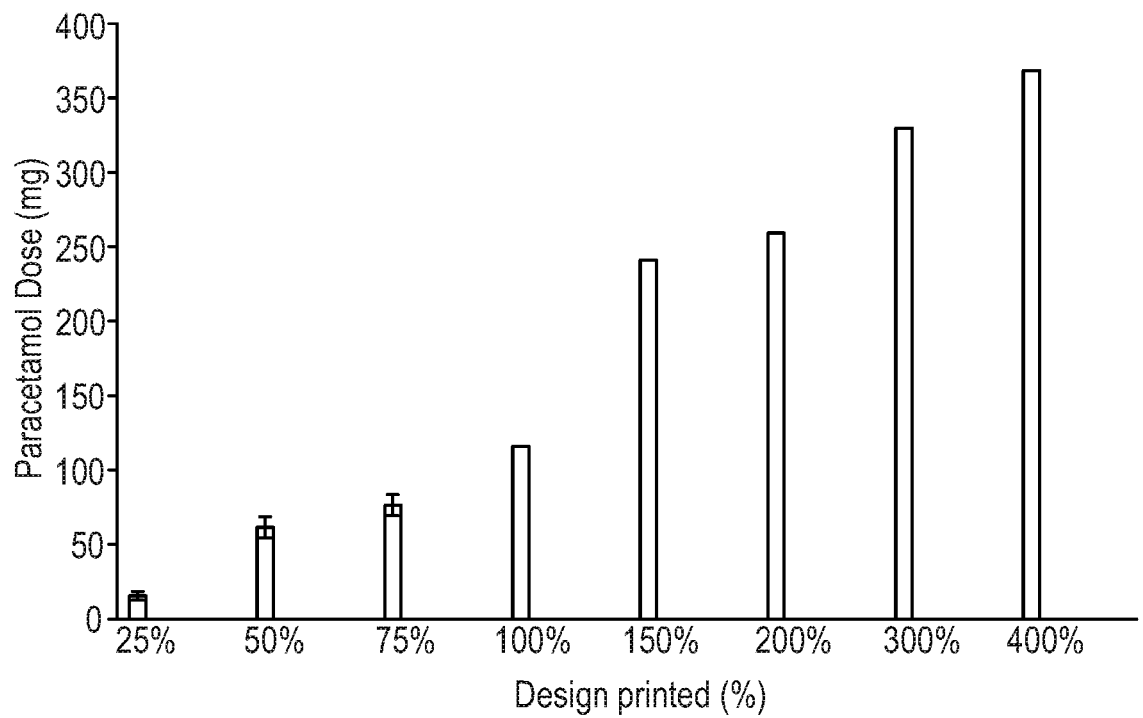
FIG. 17: Graph showing amount of paracetamol dose in an embedded item versus the percentage of the design printed.
Figure 18:
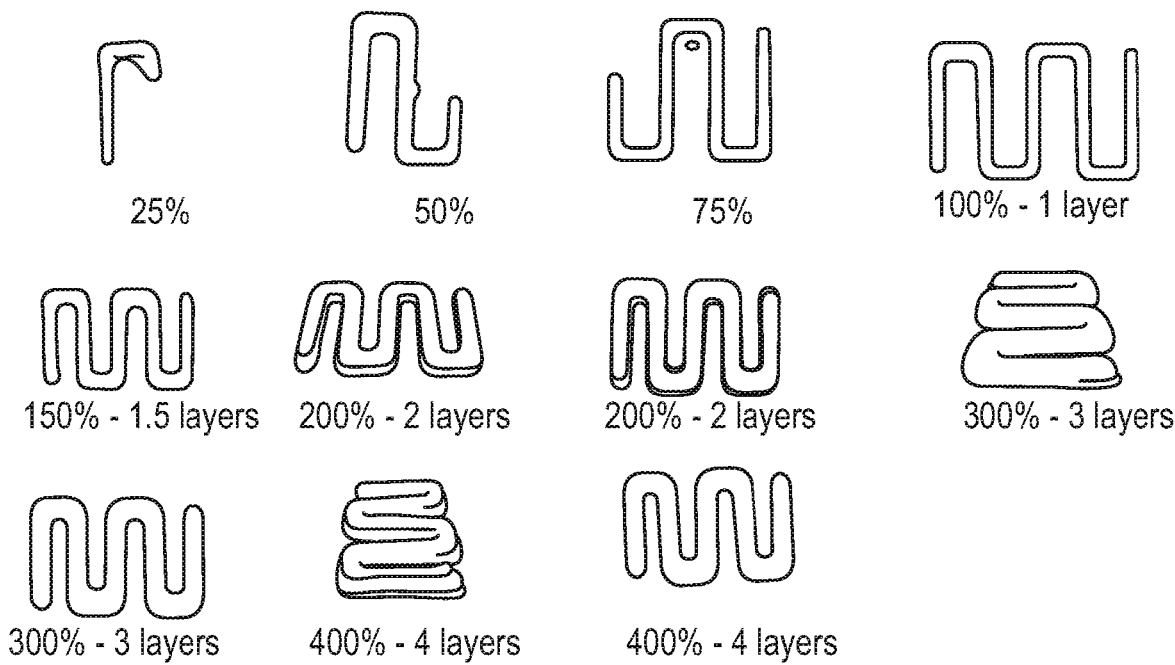
FIG. 18: Photographs showing percentage of pattern printed.
Figure 19:
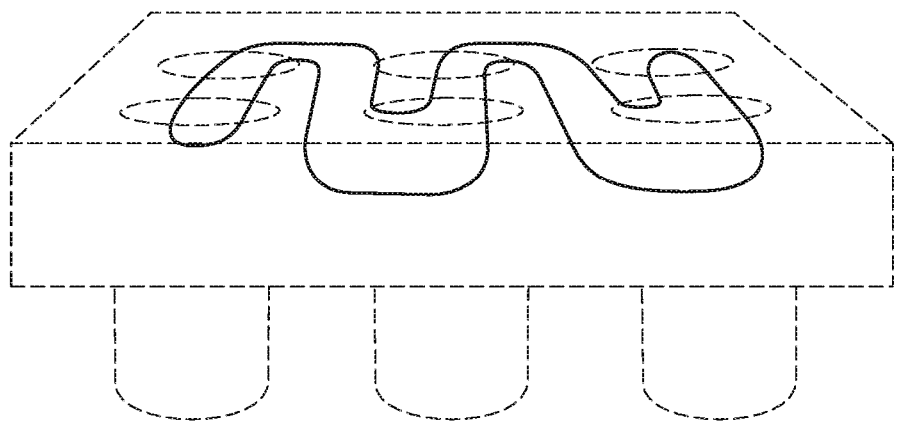
FIG. 19: Photograph showing an embedded item with 300% of pattern printed (embedded) within the solidifiable body substance.

Results and Conclusion:

By changing the printing pattern, it is possible to control the dose of the active ingredient (paracetamol), see FIG. 17, FIG. 18 and FIG. 19 (300% pattern printed).

Varying the Printing Speed

An embedded item was prepared using the methodology described above for the one step embedding printing using the solidifiable body substance as detailed in Table XIV and the embeddable substance as detailed below:

was purchased from JRS (Germany), sorbitol (Merck Parteck SI, Germany). D-mannitol, lactose, HPLC gradient grade acetonitrile were obtained from Fisher Scientific Ltd (Loughborough, UK).

Preparation for the Feed

The model drug (theophylline) and polymer (PVA 20-30K, Parteck [MXP, k75] or PVP 83K) as well as other ingredients were accurately weighed and thoroughly mixed via shear mixing using Krups F20342 grinder (Germany). Sorbitol was selected as a primary plasticiser and structure enhancer and sodium stearyl fumarate (PRUV®) as lubricant. The blend weight ratio was theophylline:polymer: sorbitol:sodium stearyl fumarate 40:35:20:5). Approximately 10 g of each blend, an additional 2 g of deionised water was added to each formulation and mixed for additional 30 seconds.

In order to assess the impact of the filler, sorbitol was replaced with equivalent amount of D-mannitol or lactose. In order to assess the impact of plasticiser concentrations (15%, 20% and 25% w/v) were assessed.

TABLE XIX

| Preparation | Polymer | Plasticizer | Theophylline | Lubricant | Temporary plasticizer (water) | Extrusion temp (° C.) | Plate temp (° C.) |
|---|---|---|---|---|---|---|---|
| PVA-sorbitol 25% | Parteck MXP (30%) | Sorbitol (25%) | 40% | PRUV® (5%) | 2 g | 100 | 50 |
| PVA-sorbitol 20% | Parteck MXP (35%) | Sorbitol (20%) | 40% | PRUV (5%) | 2 g | 100 | 50 |
| PVA-sorbitol 15% | Parteck MXP (40%) | Sorbitol (15%) | 40% | PRUV (5%) | 2 g | 100 | 50 |
| PVA-Lactose 20% | Parteck MXP (35%) | Lactose (20%) | 40% | PRUV (5%) | 2 g | 90 | No heating |
| PVA-D-Mannitol 20% | Parteck MXP (35%) | D-Mannitol (20%) | 40% | PRUV (5%) | 2 g | 90 | 40 |
| PVA 20-30K-Lactose 20% | PVA 20K-30K (35%) | lactose (20%) | 40% | PRUV (5%) | 2 g | 65 | 35 |
| PVA 83K-Lactose 20% | PVA 8-88 (35%) | lactose (20%) | 40% | PRUV (5%) | 2 g | 100 | 60 |
| PVP K28-K31 Lactose 20% | PVP K28-K31 (35%) | Lactose (20%) | 40% | PRUV (5%) | 1 g | 90 | No heating |

40 g paracetamol 60 g (locust gum 2%), i.e., 2% weight of the 60 g is locust gum and the remaining mass balance is water Four different printing speeds were tested; 50.00, 60.00, 65.00 and 70 mm/min.

Figure 20:
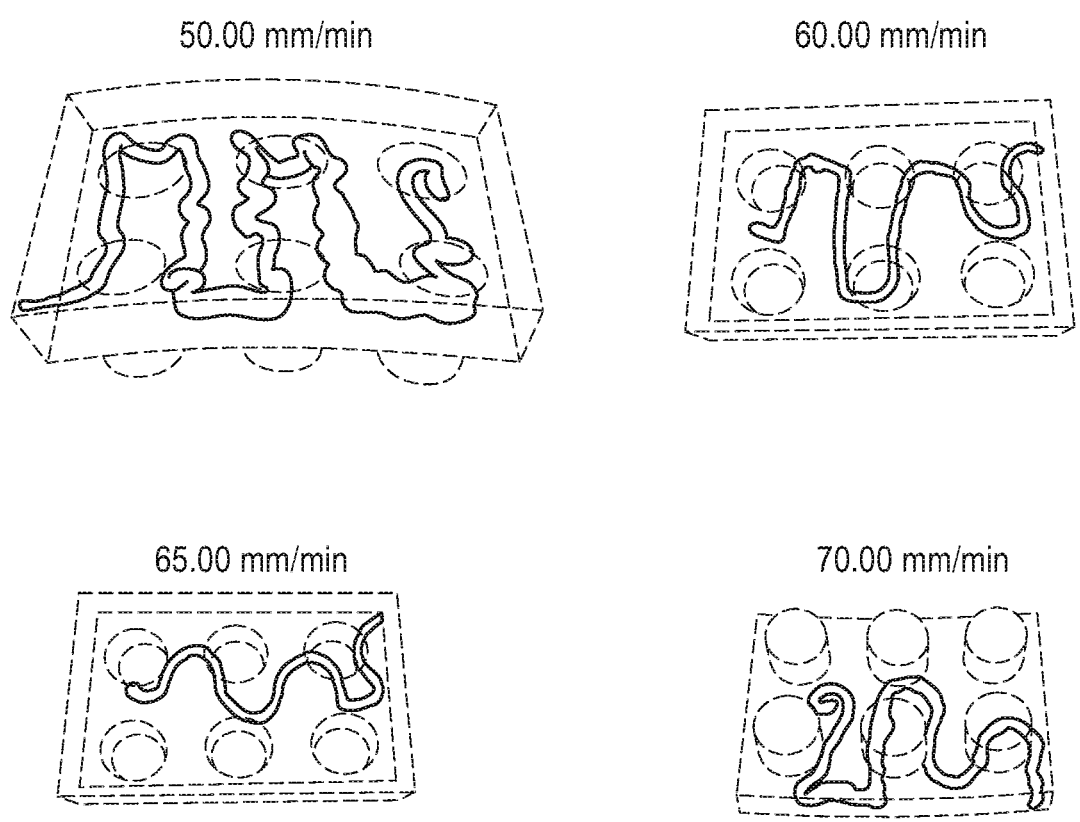
FIG. 20: Photographs showing embedded items produced using printing speeds of 50.00 mm/min, 60.00 mm/min, 65.00 mm/min and 70 mm/min.

Results:

The resulting embedded items are shown in FIG. 20. The slower the speed of printing, the less defined the printing pattern is.

Example 10—Further Examples of Direct Ink Printing with a Temporary Plasticizer

Materials

Theophylline was purchased from Acros Organics (UK). Poly(vinyl alcohol) (Parteck® MXP) was donated by Merck (Darmstadt, Germany). Sodium stearyl fumarate (PRUV)

Tablet Design and TASFEX 3D Printing

Figure 21:
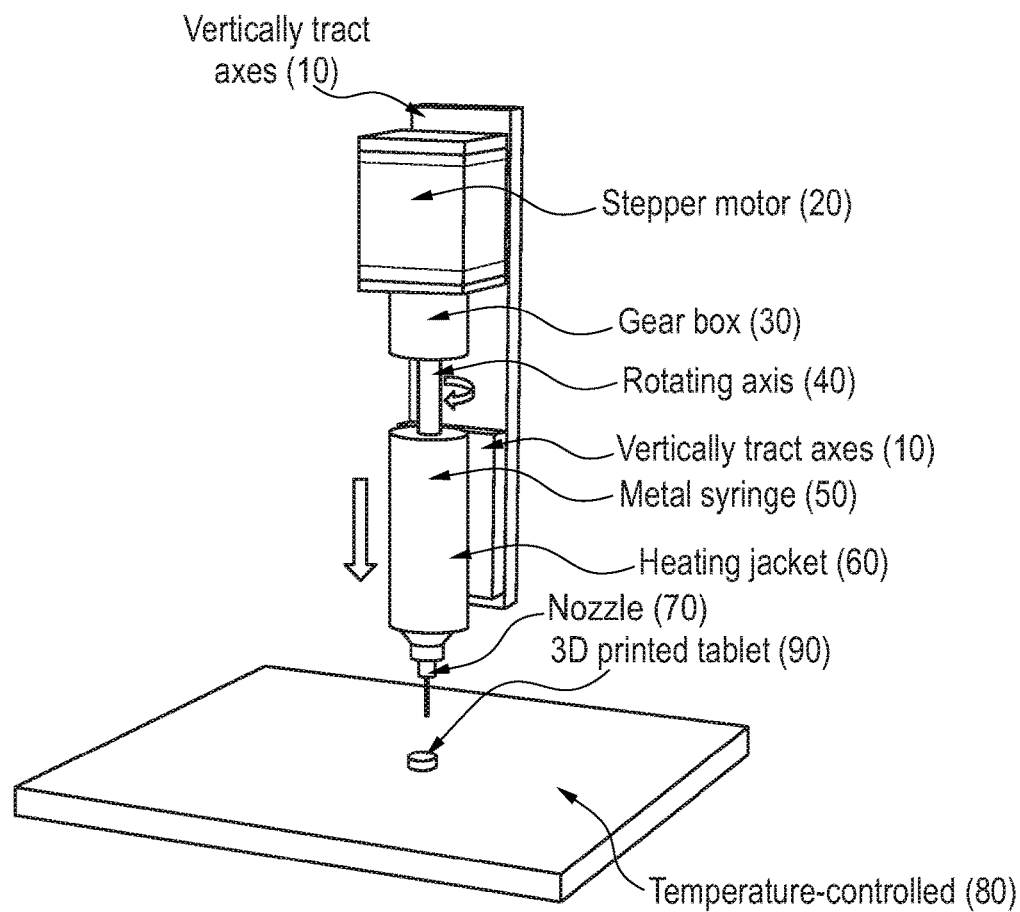
FIG. 21: A diagram of the printing machine utilised for direct ink printing.
Figure 21:
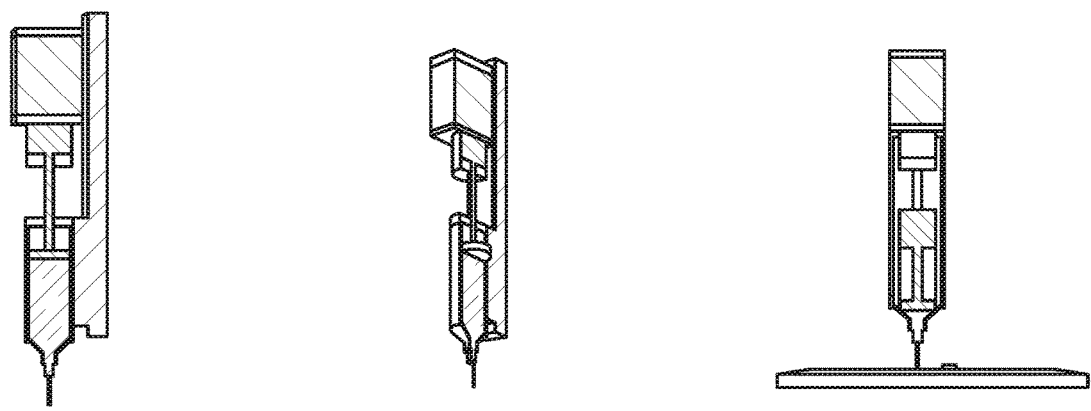

The tablets were designed in a cylindrical shape using Autodesk® 3ds Max Design 2019 (Autodesk, Inc., USA) (FIG. 21). The designs were then imported to the Slic3r version 1.3 software in stereolithographic (STL) format and converted to .gcode files using the settings specified as: Layer thickness 0.3 mm, First layer thickness 0.5 mm, speed perimeters 50%, infill speed 7 mm/sec, travel 15 mm/second first layer of 7 mm/sec. The nozzle diameter was 1.194 mm and filament diameter as 1.194 mm.

A Hyrel System 30M (Hyrel 3D, Atlanta, USA) equipped with a VOL-25 (Volcano) modular head and a 16-gauge stainless steel tip was used to fabricate the tablets for this project. The default glass plate was replaced with an acrylic sheet for better adhesion to the building plate. The settings inserted in the Repetrel software (version 3.083) for the printer head are: Nozzle diameter: 1.194, Layer z: 0.3, pulses/nL 2.3 and a material flow multiplier of 1.2 mm.

FIG. 21 shows the printing machine utilised for direct ink printing. The printing machine has a vertically tract axes (10) mounted to which is a stepper motor (20) connect to a gear box (30) and ultimately a rotating axis (40), which fits as a plunger (which applies pressure to cause extrusion) into a metal syringe (50) surrounded by a heating jacket (60) that operates in conjunction with the plunger (40) to extrude an extrudable composition through a syringe nozzle (70) onto a temperature-controlled platform (80) to produce a 3D-printed tablet (90)

Dissolution, Disintegration, Weight Uniformity

The in vitro dissolution profile of the 3D printed tablets was assessed using an Erweka DT 700 dissolution apparatus (Heusenstamm, Germany) equipped with paddle at a rotation speed of 50 rpm. The test was carried out in 750 mL of 0.1 M HCl (pH 1.2) at 37±0.5° C. for the first 2 hours to mimic the gastric media. After 2 hours, 250 mL of a 0.1 M solution of tribasic sodium phosphate was added for a final pH of 6.8.

The following examples demonstrate the applicability of the invention to various different fillers, plasticiser concentrations, PVA molecular weights and other polymers (e.g. PVP K29-32).

Figure 22:
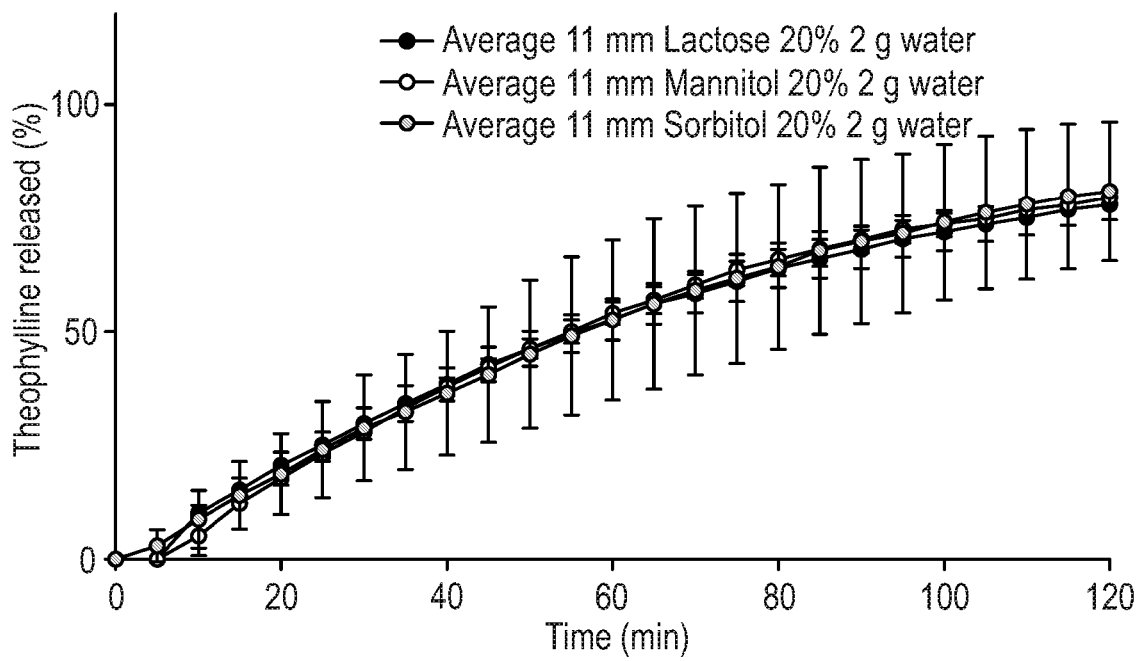
FIG. 22: A time-course drug (theophylline) release profiles using various different fillers (Lactose, Mannitol, and Sorbitol).

FIG. 22 shows time-course drug (theophylline) release profiles using various different fillers (Lactose, Mannitol, and Sorbitol). These results show that the present invention is compatible with various different sugars as fillers.

Figure 23:
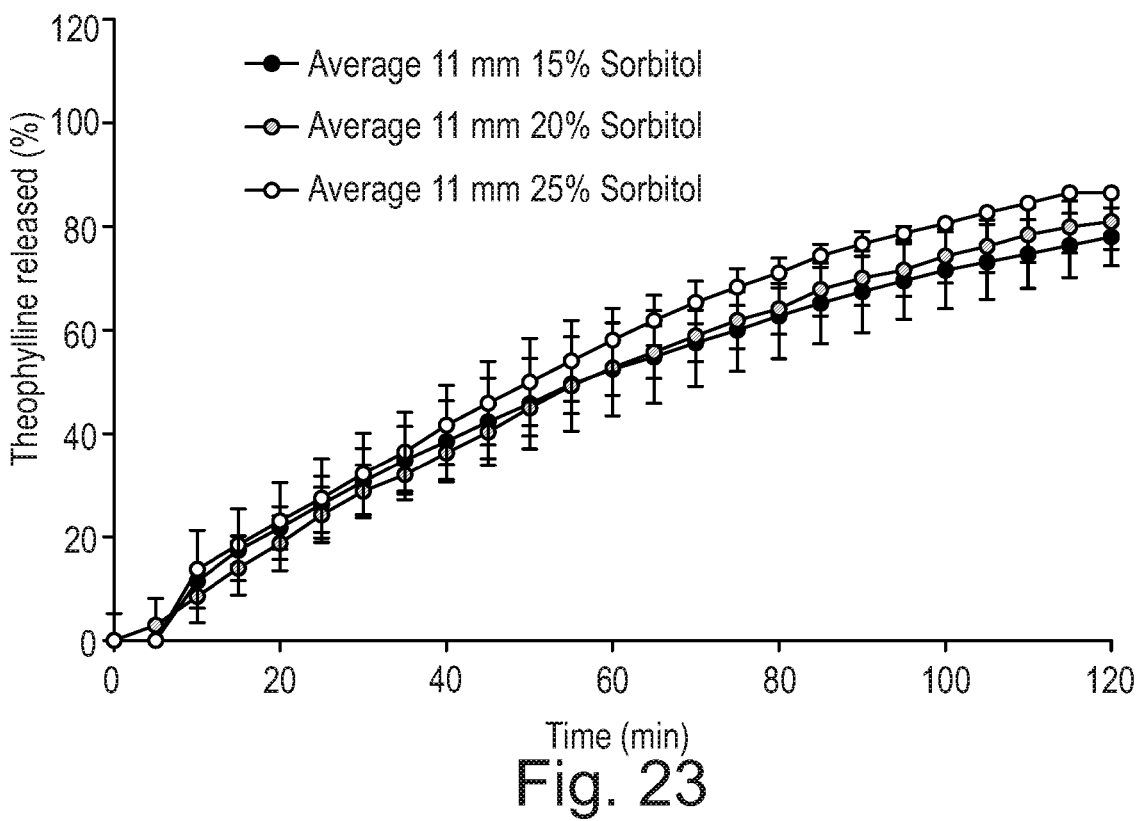
FIG. 23: A time-course drug (theophylline) release profiles using various different concentrations of filler/plasticizer (sorbitol).

FIG. 23 shows time-course drug (theophylline) release profiles using various different concentrations of filler/plasticizer (sorbitol). These results show that the present invention is compatible with various different concentrations of filler and plasticizer.

Figure 24:
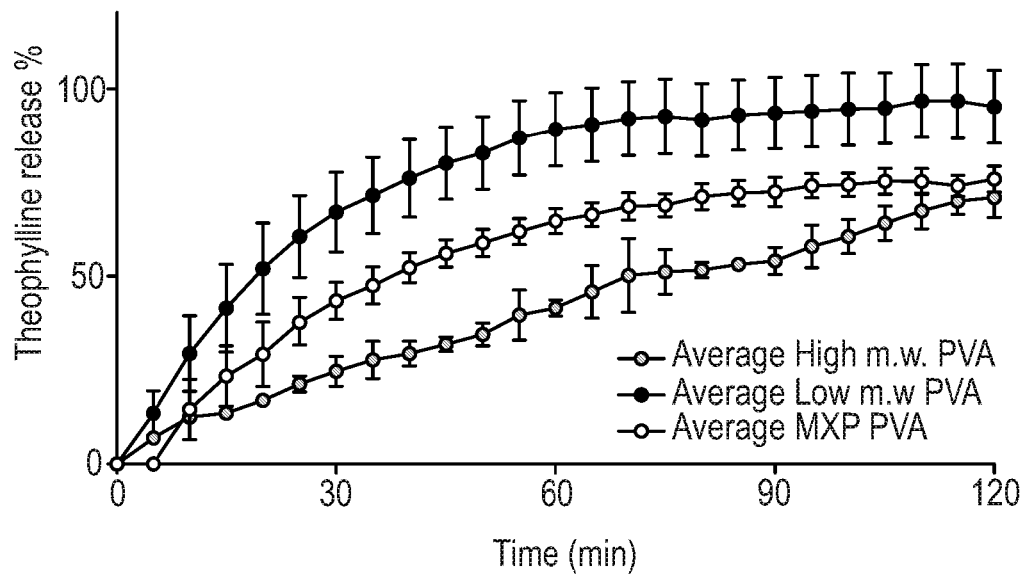
FIG. 24: A time-course drug (theophylline) release profiles using various different grades of PVA polymer.

FIG. 24 shows time-course drug (theophylline) release profiles using various different grades of PVA polymer. These results show that the present invention tolerates various polymer molecular weights and hydrolysis profiles to achieve immediate as well as extended release.

Figure 25:
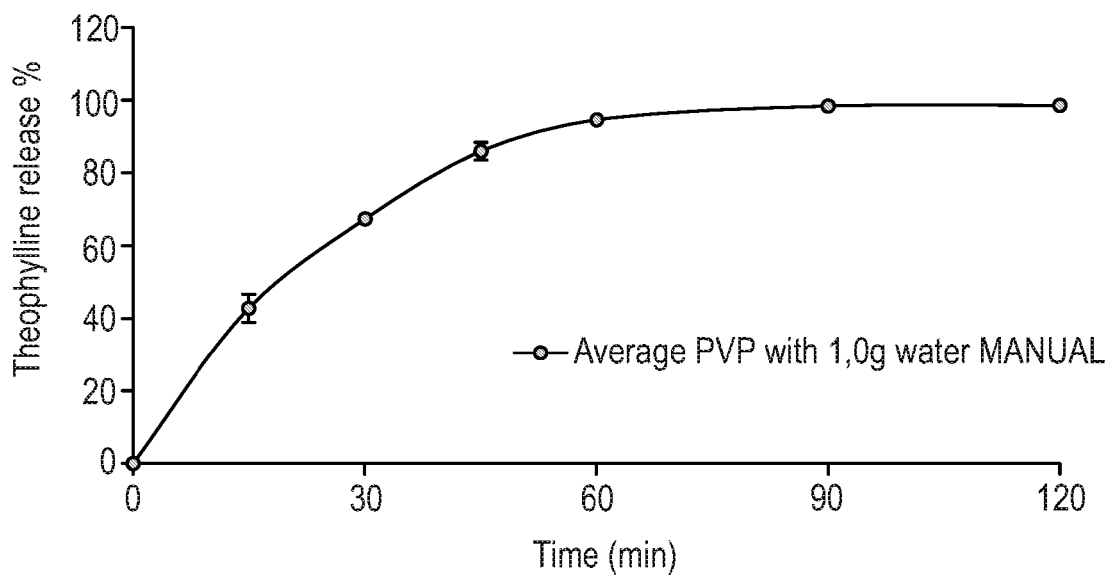
FIG. 25: A time-course drug (theophylline) release profiles using a different type of PVA polymer (PVP K29-32).

FIG. 25 shows time-course drug (theophylline) release profiles using a different type of PVA polymer (PVP K29-32). These results show that the present invention tolerates various different polymers.

Example 11—Direct Printing without Temporary Plasticizer

Preparations 1 to 3 of Example 1 may be prepared as a powder or as minitablets (via compression with a tablet press). Likewise the composition of the minitablets of Example 6 may be prepared as a powder or as minitablets as described in Example 6.

The hot-melt extrusion processes applied to the production of filaments in each of Examples 1 (for Preparations 1 to 3) and Example 6 (for the minitablets) can be equally applied to the direct ink printing processes described in Example 4, by sufficiently elevating the temperature of the syringe to facilitate production of a tablet by direct extrusion. Lower melt viscosity, lower melt temperature, compositions which can, for instance, be extrudable at temperatures between 60 and 100° C. may be developed to mitigate against temperature-induced drug degradation, and such compositions may also include high drug loadings to better protect the drug from degradation.

The same process described in this example may be applied to granulated forms. Alternatively a monolith, e.g. formed as a compressed powder or as a compressed granulated composition, may be used in the above process, optionally provided within a disposable or reusable cartridge, pre-loaded syringe, or other appropriate container that can be easily installed and removed from a direct ink printing machine. Minitablets are, however, particularly convenient in terms of storage, transport, quality assurance, and ease of use (e.g. flow) in the presently described process—e.g. loading to a syringe a melting—though minitablets may also be provided in the aforesaid disposable or reusable cartridge, pre-loaded syringe, or other appropriate container. If desired, a temporary plasticizer (e.g. water) may be added to the same syringe (or the aforesaid cartridge/container) containing the aforesaid powder, minitablets, monolith or granules, for instance to further decrease melting temperatures and thereby facilitate direct printing of tablets or other such oral dosage forms.

Where a temporary plasticizer, such as water, is included, a subsequent drying process may ensue. Such drying may be performed in situ at reduced pressure if the printing area, or at least the plate upon which tablets are printed, is suitably encapsulated within a substantially sealed container that may be evacuated.

The invention claimed is:

1. A method of preparing a customized orally-administrable pharmaceutical, nutraceutical, or food supplement tablet, the method comprising the steps of:
   i. providing a solid extrudable composition comprising an extrudable carrier, and at least one pharmaceutically, nutraceutically, or food supplement active ingredient, wherein said solid extrudable composition is initially provided either as a plurality of tablets or mini-tablets, or as a compressed monolith, on the proviso that the solid extrudable composition is not in the form of a filament;
   ii. producing an extrudable fluid by heating the solid extrudable composition in the presence of water so that the resulting extrudable fluid comprises:
      greater than or equal to 5% by weight water;
   iii. extruding the extrudable fluid to form the customized tablet;
   wherein the extruding step (iii) is performed by a 3D-printer comprising:
   a heated container for containing the solid extrudable composition and the extrudable fluid prior to the extruding step; and
   a nozzle for dispensing the extrudable fluid during the extruding step;
   wherein the heated container is heated at a temperature to maintain the extrudable fluid in a fluid state prior to the extruding step;
   the method further comprises removing at least 50% by weight of the water, via vaporisation, from the customized tablet after the step of extruding;
   wherein removing the water comprises heating and/or holding the customized tablet under reduced pressure.

2. The method of claim 1, wherein the solid extrudable composition is provided within and the extrudable fluid is produced within a heated syringe.

3. The method of claim 1, wherein the solid extrudable composition is provided as the plurality of tablets or mini-tablets.

4. The method of claim 3, wherein each tablet or mini-tablet has a longest dimension of between 0.5 mm and 10 mm.

5. The method of claim 3, wherein each tablet or mini-tablet weighs between 10 and 100 mg.

6. The method of claim 1, wherein the solid extrudable composition is provided as the monolithic extrudable compressed form.

7. The method of claim 1, further comprising a step of incorporating at least one additional excipient and/or at least one additional active ingredient into the customized tablet.

8. The method of claim 3, wherein each tablet or minitablet weighs between 10 and 100 mg and has a longest dimension of between 0.5 mm and 10 mm.

9. The method of claim 1, wherein forming the extrudable fluid comprises heating the mixture to a temperature between 60° C. and 140° C.

10. The method of claim 1, wherein extruding the extrudable fluid is performed at an extrusion temperature between 60° C. and 140° C.

11. The method of claim 1, wherein the extrudable fluid comprises less than or equal to 30% weight water.

* * * * *